US011980667B2

United States Patent
Joshi

(10) Patent No.: US 11,980,667 B2
(45) Date of Patent: May 14, 2024

(54) SHORT TAT OLIGOMERS FOR DRUG DELIVERY

(71) Applicant: The Trustees of Columbia University in the City of New York, New York, NY (US)

(72) Inventor: Shailendra Joshi, Ho Ho Kus, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 498 days.

(21) Appl. No.: 16/708,063

(22) Filed: Dec. 9, 2019

(65) Prior Publication Data

US 2020/0338202 A1 Oct. 29, 2020

Related U.S. Application Data

(63) Continuation of application No. PCT/US2018/036692, filed on Jun. 8, 2018.

(60) Provisional application No. 62/517,472, filed on Jun. 9, 2017.

(51) Int. Cl.
| | |
|---|---|
| *A61K 47/64* | (2017.01) |
| *A61K 31/05* | (2006.01) |
| *A61K 31/08* | (2006.01) |
| *A61K 31/198* | (2006.01) |
| *A61K 31/216* | (2006.01) |
| *A61K 31/7076* | (2006.01) |
| *A61M 25/06* | (2006.01) |
| *A61P 35/00* | (2006.01) |
| *C07K 7/08* | (2006.01) |
| *A61M 25/00* | (2006.01) |
| *A61M 25/10* | (2013.01) |

(52) U.S. Cl.
CPC ............ *A61K 47/645* (2017.08); *A61K 31/05* (2013.01); *A61K 31/08* (2013.01); *A61K 31/198* (2013.01); *A61K 31/216* (2013.01); *A61K 31/7076* (2013.01); *A61M 25/0606* (2013.01); *A61P 35/00* (2018.01); *C07K 7/08* (2013.01); *A61M 2025/0042* (2013.01); *A61M 2025/1052* (2013.01); *A61M 2202/048* (2013.01); *A61M 2210/0693* (2013.01)

(58) Field of Classification Search
CPC .............. C07K 7/06; C07K 7/08; A61P 35/00
See application file for complete search history.

(56) References Cited

U.S. PATENT DOCUMENTS

| | | | |
|---|---|---|---|
| 5,393,737 A | 2/1995 | Mayers et al. | |
| 5,561,121 A | 10/1996 | Ku et al. | |
| 8,829,159 B2 | 9/2014 | Kelly et al. | |
| 2005/0042753 A1* | 2/2005 | Yang ................ | A61K 47/6929 435/325 |
| 2005/0065583 A1 | 3/2005 | Voorhees et al. | |
| 2005/0147993 A1 | 7/2005 | Khan | |
| 2006/0047261 A1 | 3/2006 | Joshi | |
| 2010/0112077 A1 | 5/2010 | Desai et al. | |
| 2010/0256041 A1* | 10/2010 | Bonny ................ | A61K 47/645 514/19.5 |
| 2010/0279918 A1 | 11/2010 | Langel et al. | |
| 2012/0058113 A1 | 3/2012 | Lackey et al. | |
| 2014/0073585 A1 | 3/2014 | Jung et al. | |

FOREIGN PATENT DOCUMENTS

| | | | |
|---|---|---|---|
| WO | 2016054510 A1 | 4/2016 | |
| WO | 2016140624 A1 | 9/2016 | |

OTHER PUBLICATIONS

Foerg, et al., "On the Biomedical Promise of Cell Penetrating Peptides: Limits Versus Prospects", J. Pharm. Sci. 97(1): 144-162 (2007).
International Search Report cited in corresponding application PCT/US2018/036692 dated Oct. 22, 2018.
Joshi, et al., "Targeting brain tumors by intra-arterial delivery of cell-penetrating peptides: a novel approach for primary and metastatic brain malignancy", J. Neuro-Oncology 135(3):497-506 (2017).
Ma, et al., "Molecular Determinants for Cellular Uptake of Tat Protein of Human Immunodeficiency Virus Type 1 in Brain Cells", J. Virology 71(3):2495-2499 (1997).
Nishimura, et al., "Combinatorial Targeting of the Macropinocytotic Pathway in Leukemia and Lymphoma Cells", J. Biol. Chem. 283(17):11752-62 (2008).

* cited by examiner

*Primary Examiner* — Pancham Bakshi
(74) *Attorney, Agent, or Firm* — BakerHostetler

(57) ABSTRACT

Trans-activating transcription (TAT) factor peptide oligomers coupled with functional agents can selectively complex to the anionic surface of cancerous cells. The TAT conjugates can be delivered to the locus of the tumors using intra-arterial injection during transient blood flow arrest.

12 Claims, 64 Drawing Sheets
(46 of 64 Drawing Sheet(s) Filed in Color)
Specification includes a Sequence Listing.

Dose: 0.25 mg TAT dimer With Tumor    Dose: 0.25 mg TAT dimer Without Tumor    Dose: 0.125 mg TAT dimer With Tumor

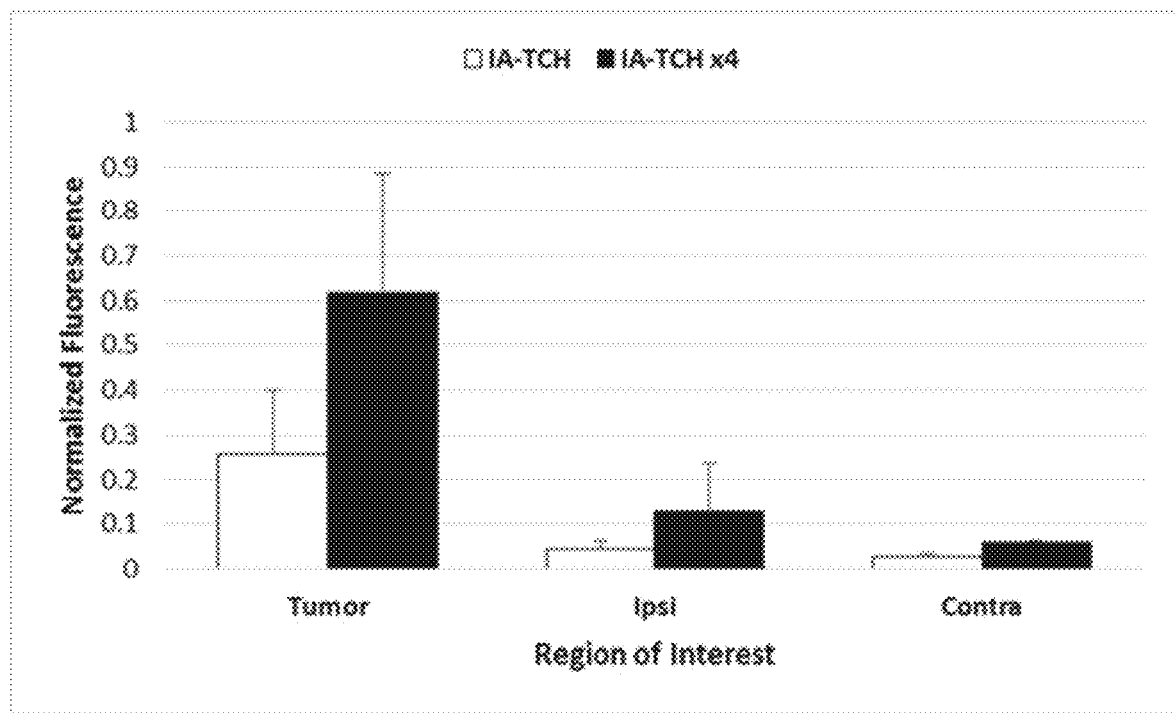

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Lys Lys Arg Arg Gln Arg Arg Arg
1               5

<210> SEQ ID NO 2
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Lys Lys Arg Arg Gln Arg Arg Arg Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Arg Lys Lys Arg Arg Gln Arg Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Arg Lys Lys Arg Arg Gln Arg Arg Arg Cys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Arg Lys Lys Arg Arg Gln Arg Arg Arg Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Arg Lys Lys Arg Arg Gln Arg Arg Arg Gly
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Arg Lys Lys Arg Arg Gln Arg Arg Arg Pro Gln
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Arg Lys Lys Arg Arg Gln Arg Arg Arg Pro Gln
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Arg Lys Lys Arg Arg Gln Arg Arg Arg Pro Pro Gln Gln
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Lys Lys Arg Arg Gln Arg Arg Arg Pro Pro Gln Gln
1               5                   10

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Arg Lys Lys Arg Arg Gln Arg Arg Arg Pro Pro Gln Gln Gly Arg
1               5                   10                  15

Lys Lys Arg Arg Gln Arg Arg Arg Pro Pro Gln Gln
            20                  25

<210> SEQ ID NO 13
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 13

Arg Arg Arg Arg Arg Arg Arg Arg
1               5
```

Short TAT Oligomers for Drug Delivery

CROSS-REFERENCE TO RELATED APPLICATIONS

The present application claims priority to U.S. Provisional Application No. 62/517,472, filed Jun. 9, 2017, the entirety of which is incorporated herein by reference.

STATEMENT OF GOVERNMENT INTEREST

This invention was made with U.S. government support under Grant No. R01 CA 138643 awarded by the National Institutes of Health (NIH). The U.S. Government has certain rights in this invention.

SEQUENCE LISTING

The instant application contains a Sequence Listing which has been submitted electronically in ASCII format and is hereby incorporated by reference in its entirety. Said ASCII copy, created on Jun. 4, 2018, is named 16-50210-WO_SL.txt and is 3,580 bytes in size.

BACKGROUND

The outer surfaces of most cancer cell membranes and their vascular endothelial cells have an overexpression of anionic lipids that is largely due to an excess of phosphatidylserine (PS). The overexpression results in a net negative charge on the cell surface. Furthermore, a wide range of cationic cell-penetrating peptides (CPPs), like the trans-activating transcription factor (TAT) are available that can target the negative charge on the malignant cell membranes. In addition, TAT can cross the blood brain barrier (BBB) and can deliver large drug cargos.

A variety of charged nanoparticles (NP) decorated with CPPs or other cationic molecules, are under development for targeting cancers by intravenous (IV) delivery for imaging and therapeutic purposes. A potential limitation of their IV delivery is the attenuation of their charge by circulating serum proteins, drugs and red blood cells. Cationic charge also predisposes to the phagocytosis of the NPs and increases their renal clearance. These hurdles limit the clinical utility of intravenously delivered cationic NPs.

There is a need for improved chemotherapeutic options that can more selectively target cancerous cells with less toxicity to non-tumor cells and improve uptake and delivery of functional agents.

SUMMARY

The present disclosure provides compositions comprising TAT-conjugated functional agents and methods for their preparation and use, including but not limited to, the use of such compositions for the administration to a subject for the treatment of cancer. The present disclosure further provides methods for intra-arterial injection during transient cerebral hypoperfusion (IA-TCH).

In some embodiments, a peptide conjugate or pharmaceutically acceptable salt thereof is provided. The peptide conjugate or pharmaceutically acceptable salt thereof includes a peptide which, in turn, comprises one or more trans-activating transcription factor (TAT) sequences. The peptide is conjugated to a functional agent which can be an imaging agent, a pharmaceutical agent, a tracer, a peptide, a polymer, a polysaccharide, a saccharide, a nucleic acid or a nanoparticle. In certain aspects the peptide conjugate or pharmaceutically acceptable salt thereof includes melphalan coupled to a peptide having one or more TAT sequences. In some embodiments, a pharmaceutical composition is provided which comprises the peptide conjugate or pharmaceutically acceptable salt thereof.

In some embodiments, a method for treating cancer is provided which includes the steps of anesthetizing a subject, reducing blood flow in said subject and intra-arterially administering a pharmaceutical composition comprising a therapeutically effective amount of a peptide conjugate or pharmaceutically acceptable salt thereof in accordance with the foregoing embodiments. In certain aspects, the peptide conjugate or pharmaceutically acceptable salt thereof includes melphalan coupled to a peptide having one or more TAT sequences.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

FIG. 28C depicts a chart comparing single arrest IA-TCH (white) to 4× arrest IA-TCH (black) by brain region.

DESCRIPTION

Figure 1A:
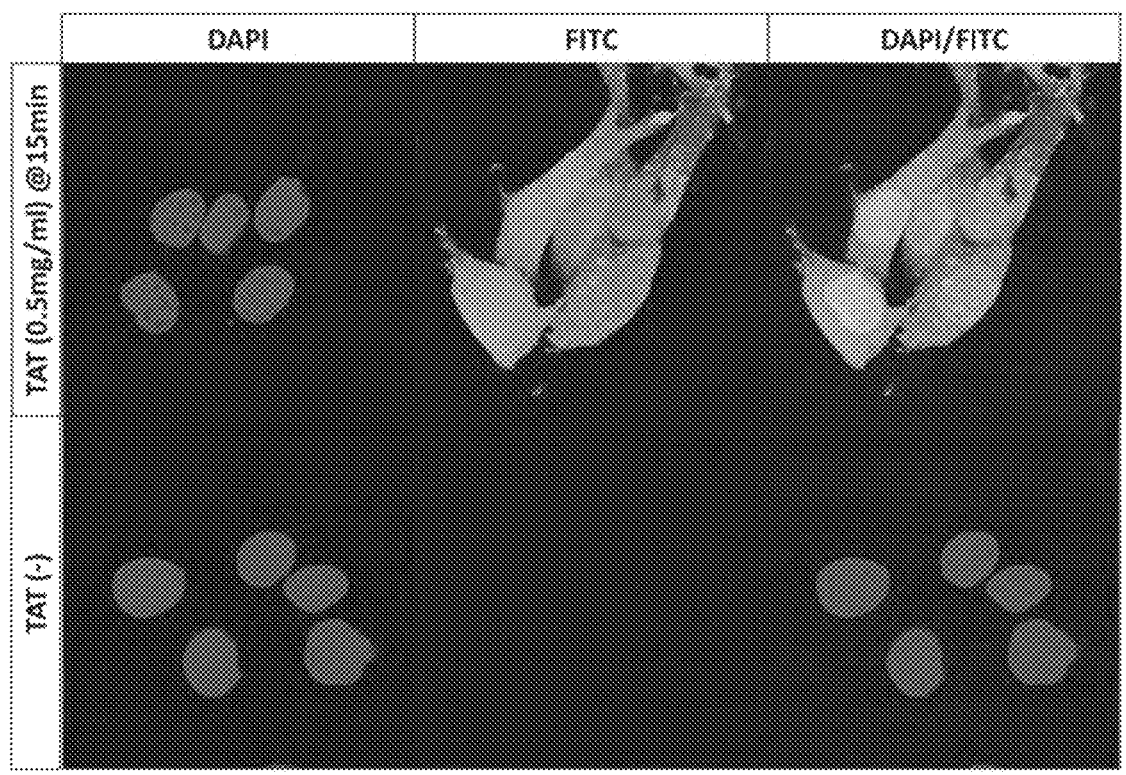
FIG. 1A depicts images collected by confocal microscopy of 9L cells after exposure to fluorescein (FITC)-labeled TAT monomer and DAPI staining.
Figure 1B:
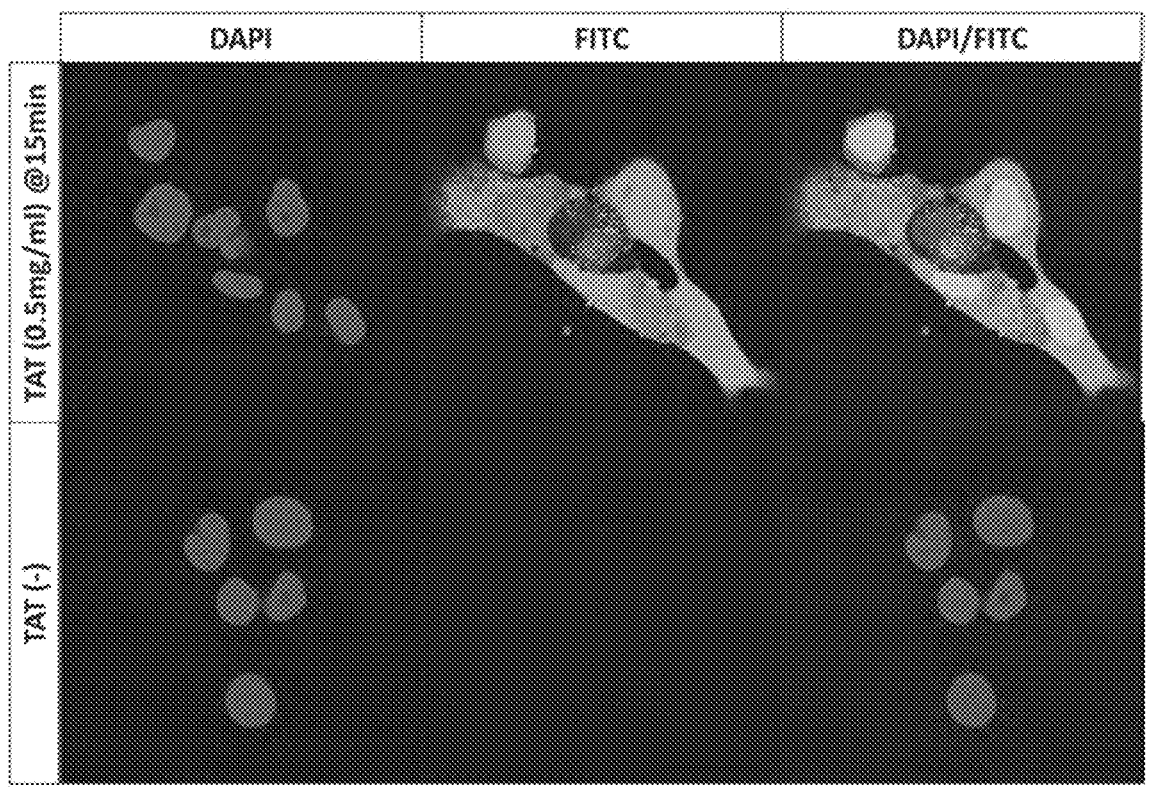
FIG. 1B depicts images collected by confocal microscopy of 4T1 cells after exposure to FITC-labeled TAT monomer and DAPI staining.
Figure 1C:
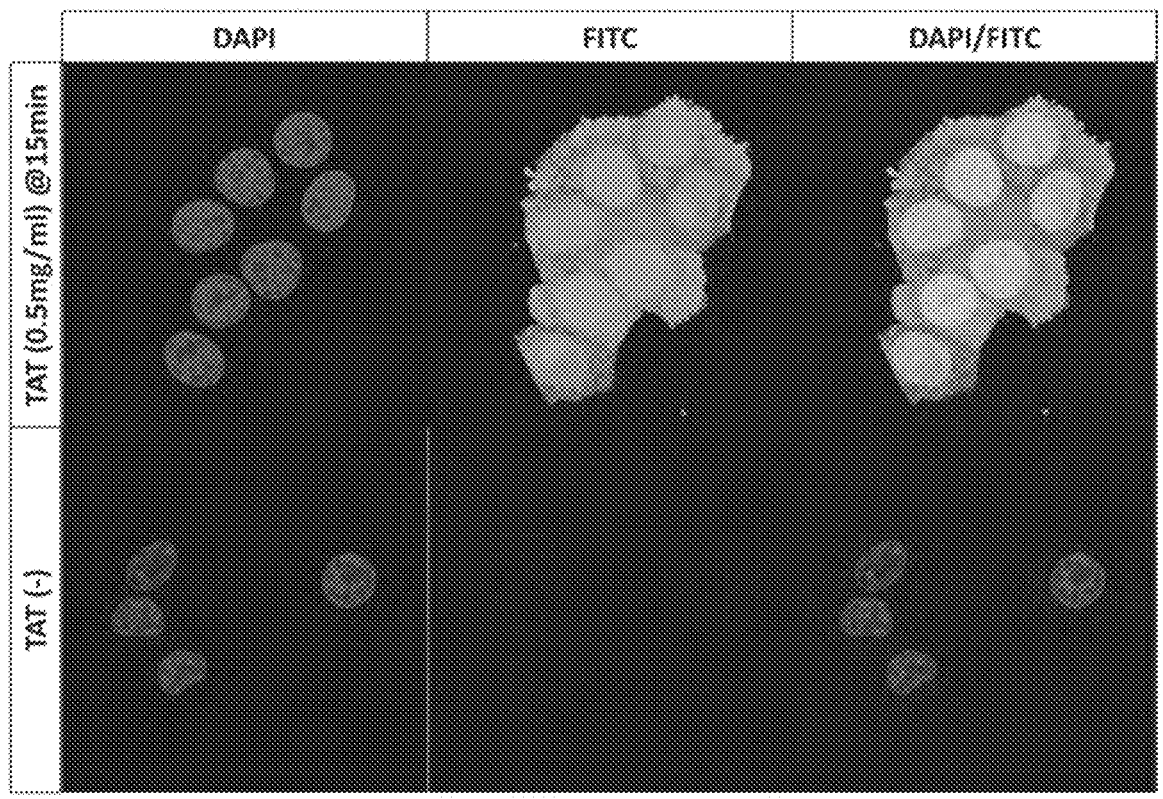
FIG. 1C depicts images collected by confocal microscopy of LLC cells after exposure to FITC-labeled TAT monomer and DAPI staining.
Figure 1D:
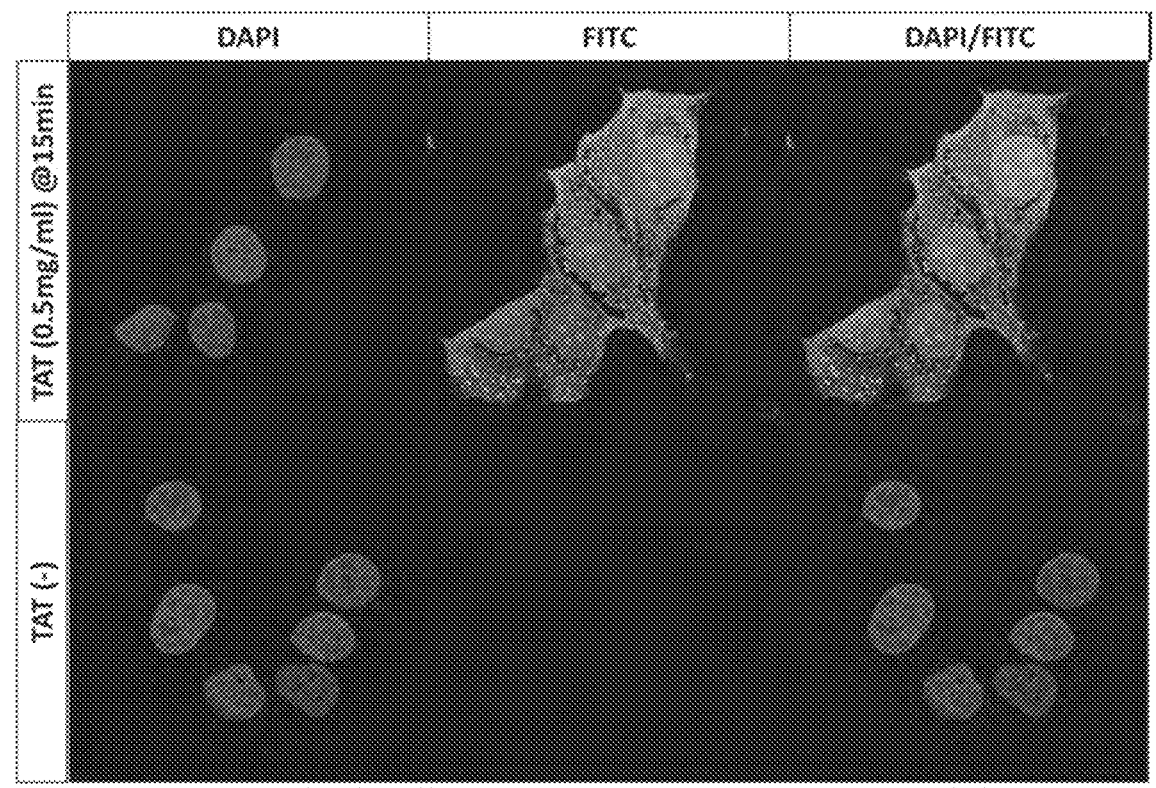
FIG. 1D depicts images collected by confocal microscopy of SKOV-3 cells after exposure to FITC-labeled TAT monomer and DAPI staining.

The present disclosure describes particular embodiments and with reference to certain drawings, but the subject matter is not limited thereto. The drawings described are only schematic and are non-limiting. In the drawings, the size of some of the elements may be exaggerated or distorted and not drawn on scale for illustrative purposes. Where the elements of the disclosure are designated as "a" or "an" in first appearance and designated as "the" or "said" for second or subsequent appearances, "the" or "said" refers back to the first appearance, unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Certain terminology is used in the following description for convenience only and is not limiting. Certain words used herein designate directions in the drawings to which reference is made. Unless specifically set forth herein, the terms "a," "an" and "the" are not limited to one element, but instead should be read as meaning "at least one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

The terms "oligomer" and "short polymer" are used herein to designate peptide chains having molecular weight less than 10,000 daltons. The term "TAT oligomer conjugate" refers to a conjugate of a peptide sequence having at least one conserved region comprising the sequence RKKRRQRRR (SEQ ID NO: 1) coupled or conjugated to at least one functional agent. Such functional agents can include, but are not limited to, an imaging agent, pharmaceutical agent, tracer, peptide, polymer, polysaccharide, nucleic acid or nanoparticle.

Unless otherwise defined, all technical and scientific terms used herein have the same meaning as commonly understood by one of ordinary skill in the art.

Most cancer cells overexpress anionic lipids on the cell membrane, such as phosphatidylserine (PS) and, thus, carry a relatively greater surface charge than non-cancerous cells. The negative surface charge can be used as a target for guiding drugs and tracers using positively charged carriers.

Peptide sequences can be designed that carry a positive charge. Some peptides, such as cell penetrating peptides (CPPs) (e.g. trans-activating transcription factor (TAT)) can even penetrate the cell membrane to deliver tracers and therapeutic compounds. Coupled with the unique propensity of TAT and TAT oligomers to cross the blood-brain barrier (BBB) as well as their capacity to facilitate the delivery of large drug cargos, such TAT and TAT oligomers can provide effective carriers for agents that target brain tumor cells. However, when these compounds are injected in the bloodstream, they may bind non-specifically to other anionic entities besides the target cancer cells, such as red blood cells, circulating proteins and anionic drugs which can reduce the effectiveness of such peptides.

To overcome this problem, intra-arterial injection of CPP-linked drugs during transient flow arrest (IA-FA) can be used. High resting cerebral and brain tumor blood flow can present a challenge for IA drug delivery in the treatment of brain tumors. The IA-FA delivery method involves injections of small, carefully controlled boluses of drugs or other biologically-active agents into arteries directly supplying the target site, such as a tumor, particularly under conditions of reduced flow. IA-FA has been shown to be feasible by using balloon occluding micro-catheters and adenosine induced cardiac pauses in human subjects. IA-FA permits delivery of drugs and tracers to a target site while minimizing, even avoiding, contact with blood and blood components. Thus, the IA-FA presents superior results to conventional IV delivery and could significantly improve tumor selective deposition of cationically charged therapeutic agents such as TAT-coupled agents.

TAT peptides have a conserved 9 amino acid sequence that is considered essential to their function. In single-letter coding, the sequence is RKKRRQRRR (SEQ ID NO: 1). This sequence can be modified by addition of various additional amino acids on either or both the N-terminal and C-terminal ends of the conserved sequence, including G, C, P, Q, and combination thereof to form peptides of 9-14 (or more) amino acids. Example sequences include but are not limited to RKKRRQRRR (SEQ ID NO: 1), GRKKRRQRRR (SEQ ID NO: 2), GRKKRRQRRRG (SEQ ID NO: 3), CRKKRRQRRR (SEQ ID NO: 4), CRKKRRQRRRC (SEQ ID NO: 5), GRKKRRQRRRC (SEQ ID NO: 6), CRKKRRQRRRG (SEQ ID NO: 7), GRKKRRQRRRPQ (SEQ ID NO: 8), CRKKRRQRRRPQ (SEQ ID NO: 9), CRKKRRQRRRPPQQ (SEQ ID NO: 10) and GRKKRRQRRRPPQQ (SEQ ID NO: 11).

TAT oligomers, including peptides comprising TAT sequences, can include monomers and multimers. In some embodiments, such peptides can include one or more TAT sequences. In some embodiments, a TAT peptide can include two TAT sequences, three TAT sequences, four TAT sequences, five TAT sequences, or more.

TAT oligomers, including but not limited to TAT monomers, TAT dimers, TAT trimers, TAT quadrimers or TAT pentamers can be coupled or conjugated to functional agents, including an imaging agent, pharmaceutical agent, tracer, peptide, polymer, polysaccharide, saccharide, nucleic acid or nanoparticle, and any combinations thereof. Coupling techniques are well-known in the art and generally comprise activating a moiety on the functional agent and/or the TAT oligomer and treating the activated moiety with a suitable reactant moiety on the other partner in the conjugate. Alternatively, a conjugate can be prepared from a single amino acid group coupled with a functional agent that can be incorporated into the peptide sequence by standard peptide synthesis procedures. For example, solid state peptide synthesis techniques can be used to attach the conjugated amino acid group to a terminal end of the TAT oligomer. The functional agents can be coupled to the TAT oligomers at the C-terminal end, the N-terminal end or between TAT sequences. Further, TAT oligomer conjugates can include a linker sequence between the functional agent and the peptide portion which includes the TAT sequences. Such linkers can include, but are not limited to, amino acids, peptides and covalent linkages. In some embodiments, the linker can include a lysine residue. Other non-limiting examples of linkers include maleimide sulfur carbon bonds, hydrogen bonds, and SMP (BMPS). In certain aspects, TAT oligomers can be conjugated to more than one functional agent. By way of example, but not limitation, a TAT oligomer can be conjugated at both its N-terminal end and C-terminal end with or without linkers between the functional agents and the TAT oligomer. In some embodiments, a TAT oligomer comprises a pharmaceutical agent and a tracer. In some embodiments, a TAT oligomer can comprise two tracers as functional agents. For example, a TAT oligomer can include, in addition to one or more TAT sequences, two fluorescent functional agents such as fluorescein.

Functional agents which can be coupled to TAT oligomers, including TAT monomer, include but are not limited to conventional drugs such as alkylating agents, alkyl sulfonates, ethylene imines, nitrosoureas, triazenes, vinca alkyloids, anthracyclins, antimetabolites, aromatase inhibitors, topoisomerase inhibitors, taxanes, and platinum drugs. Functional agents can also include, but are not limited to, agents that act as receptor tyrosine kinase (RTK) inhibitors, such as erlotinib and desmethyl erlotinib that act on the epidermal growth factor receptor (EGFR). Functional agents can also include but are not limited to gefitinib, osimertinib, sunitinib, dasatinib, lapatinib, sorafenib, nilotininb, bosutinib, neratinib, vatalanib, WZ4002, XL999, PF-04948568, nimotuzumab, anti-VEGFR agents such as motesanib, pazopanib, cediranib, semaxinib, anti-HER agents such as lapatinib, afatinib, ant-Ras agents such as tipifamib, laonafarnib, cediranib, XL281; anti-MEK agents such as selumetinib; Pan-Class 1 PI3K inhibitors such as pictilisib, idelalisib, buparlisib, BAY80-6946, pilarilisib; PX866, ZSTK474, CH5132799, GSK2636771, AZD8186, SAR260301, taselisib, alpelisib, serabelisib, BAY1082439, duvelisib, AMG319; dactolisib, GDC-0980 (RG7422), gedatolisib, PF-04691502, GSK-2126458, SAR245409, cilengitide, GDC-0941, vistusertib, AKT agents such as perifosine, vismodegib, sonidegib, BMS-833923, glasdegib, taladegib; and everolimus, ridaforolimus, sirolimus, temsirolimus, OSI-027, AZD2014, MLN0128, torkinib. Gamma-sectrase complex inhibitors such as MK0752, PF-03084014, BMS-906024; HDAC inhibitors such as panobinostat; resveratrol, R04929097, MED10639, OMP-21M18, OMP-52M51 OMP-59R5 and celecoxib. Other specific examples of agents to conjugate to TAT oligomers include but are not limited to bevacizumab, cetuximab, panitumumab, trastuzumab, pertuzumab, AMG479, IMC-A12, AMG102, UCN01, XL99, AZDo530, lapatinib, tipifamib, lonafarnib, vatalanib, AMG706, pazopanib, cediranib, sorafenib, XL281, everolimus, AZD6244, depsipeptide, vorinostat, PG-04948568, gefitinib, erlotinib, nimotuzumab, imatinib, sunitinib, dasatinib, cilengitide, GDC-0941, vismodegib, and celecoxib. Exemplary, non-limiting examples of conventional drugs are shown in Table 1 and can also include pharmaceutically acceptable salts thereof.

TABLE 1

Non-limiting Examples of Conventional Drugs for Conjugation to TAT Oligomers
Alkylating Agents

| Nitrogen mustard analogues (MOA) | Chemical Structure | Formula Molecular weight |
|---|---|---|
| Mechlorethamine | 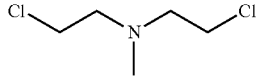 | $C_5H_{11}Cl_2N$ 156.05 |
| Estramustine phosphate | 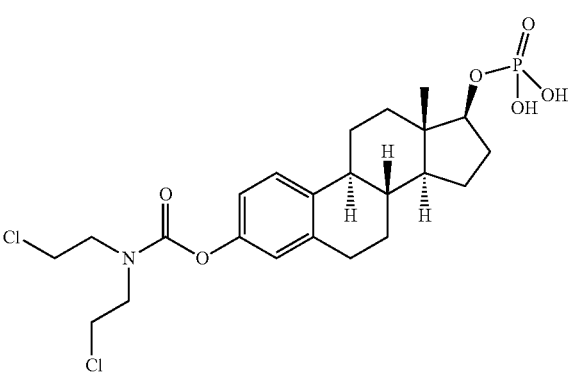 | $C_{23}H_{32}Cl_2NO_6P$ 520.384 |

TABLE 1-continued
| | | |
|---|---|---|
| Uramustin | 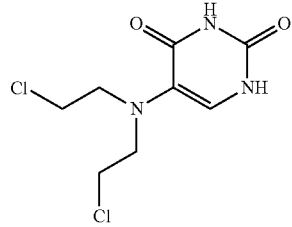 [SMILES: O=c1[nH]cc(N(CCCl)CCCl)c(=O)[nH]1] | $C_8H_{11}Cl_2N_3O_2$<br>252.097 |
| Cyclophosphamide | 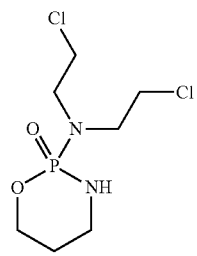 [SMILES: O=P1(N(CCCl)CCCl)NCCCO1] | $C_7H_{15}Cl_2N_2O_2P$<br>261.086 |
| Chlorambucil | 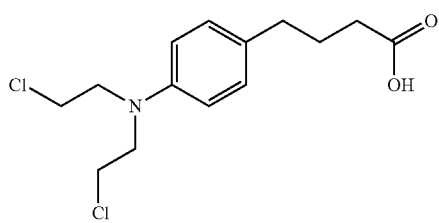 [SMILES: O=C(O)CCCc1ccc(N(CCCl)CCCl)cc1] | $C_{14}H_{19}Cl_2NO_2$<br>304.212 |
| Melphalan | 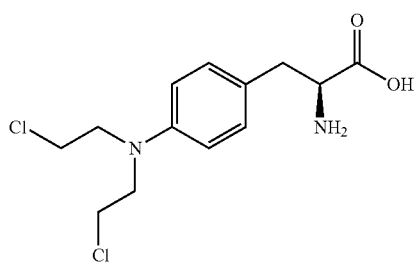 [SMILES: N[C@@H](Cc1ccc(N(CCCl)CCCl)cc1)C(=O)O] | $C_{13}H_{18}Cl_2N_2O_2$<br>305.2 |
| Ifosfamide | 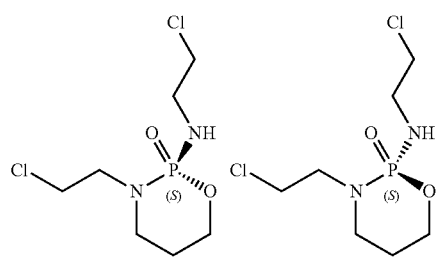 | $C_7H_{15}Cl_2N_2O_2P$<br>261.1 |
| Trofosfamide | 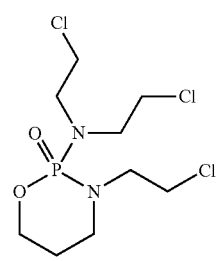 [SMILES: O=P1(N(CCCl)CCCl)OCCCN1CCCl] | $C_9H_{18}Cl_3N_2O_2P$<br>323.58 |

TABLE 1-continued

| Estramustine | | $C_{23}H_{31}Cl_2NO_3$<br>440.405 |

Alkyl Sulfonates

| Alkyl Sulfonate | Chemical Structure | Formula<br>Molecular weight |
|---|---|---|
| Busulfan | 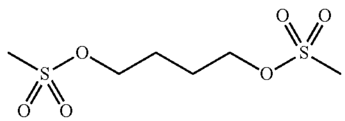 | $C_6H_{14}O_6S_2$<br>246.304 |
| Treosulfan | 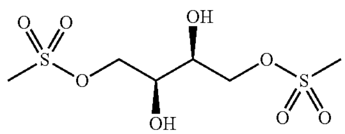 | $C_6H_{14}O_8S_2$<br>278.3 |
| Mannosulfan | 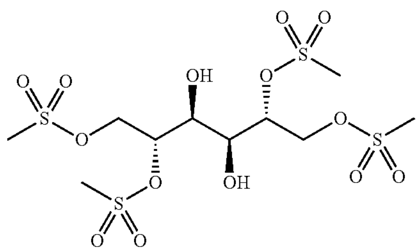 | $C_{10}H_{22}O_{14}S_4$<br>494.53 |

Ethylene Imines

| Ethylene Imine | Chemical Structure | Formula<br>Molecular weight |
|---|---|---|
| Thiotepa | 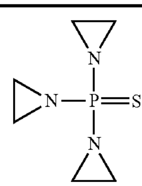 | $C_6H_{12}N_3PS$<br>189.23 |
| Altretamine | 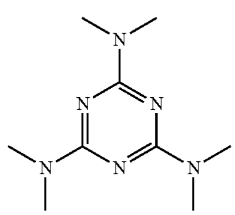 | $C_9H_{18}N_6$<br>210.28 |
| Triaziquone | 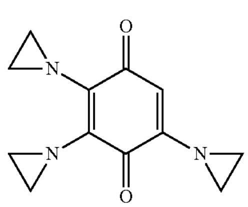 [SMILES: O=C1C=C(N2CC2)C(=O)C(N2CC2)=C1N1CC1] | $C_{12}H_{13}N_3O_2$<br>231.25 |

TABLE 1-continued
| Carboquone | 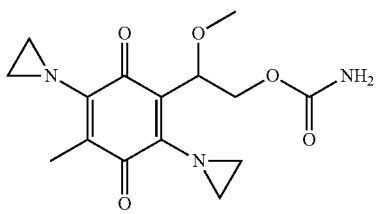 [SMILES: COC(COC(N)=O)C1=C(N2CC2)C(=O)C(C)=C(N2CC2)C1=O] | $C_{15}H_{19}N_3O_5$ 321.33 |
Nitrosoureas
| Nitrosourea | Chemical Structure | Formula Molecular weight |
|---|---|---|
| Carmustine | 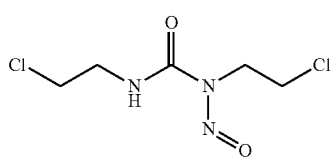 [SMILES: O=NN(CCCl)C(=O)NCCCl] | $C_5H_9Cl_2N_3O_2$ 214.05 |
| Lomustine | 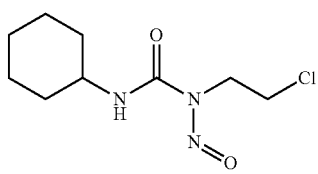 [SMILES: O=NN(CCCl)C(=O)NC1CCCCC1] | $C_9H_{16}ClN_3O_2$ 233.695 |
| Semustine | 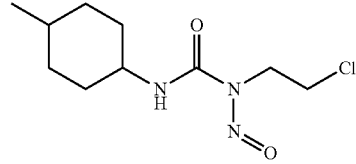 [SMILES: CC1CCC(NC(=O)N(CCCl)N=O)CC1] | $C_{10}H_{18}ClN_3O_2$ 247.72 |
| Streptozocin | 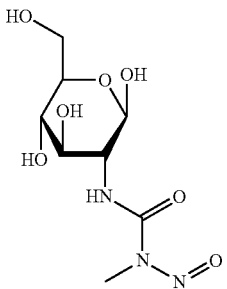 | $C_8H_{15}N_3O_7$ 265.221 |
| Fotemustine | 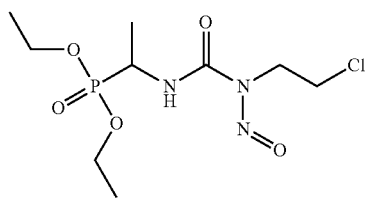 [SMILES: CCOP(=O)(OCC)C(C)NC(=O)N(CCCl)N=O] | $C_9H_{19}ClN_3O_5P$ 315.691 |
| Nimustine | 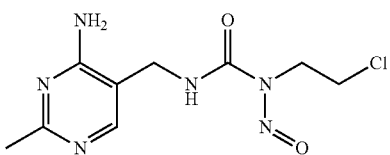 [SMILES: Cc1ncc(CNC(=O)N(CCCl)N=O)c(N)n1] | $C_9H_{13}ClN_6O_2$ 272.69 |

TABLE 1-continued
| Ranimustine | 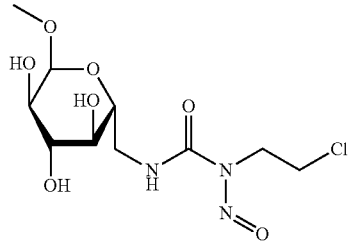 | $C_{10}H_{18}ClN_3O_7$ 327.71 |
Triazenes (Non-classical)
| Triazene | Chemical Structure | Formula Molecular weight |
|---|---|---|
| Dacarbazine | 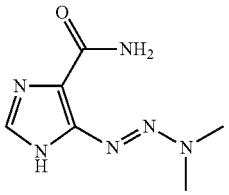 | $C_6H_{10}N_6O$ 182.18 |
| Temozolomide | 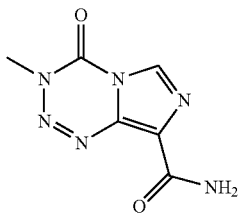 | $C_6H_6N_6O_2$ 194.151 |
Vinca Alkyloids
| Vinca Alkyloid | Chemical Structure | Formula Molecular weight |
|---|---|---|
| Vinblastine | 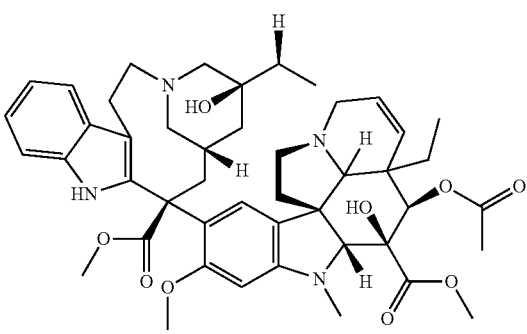 | $C_{46}H_{58}N_4O_9$ 810.975 |
| Vinorelbine | 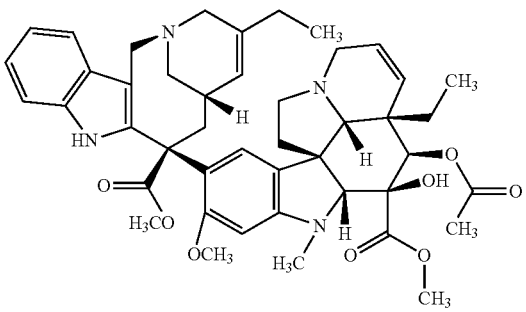 | $C_{45}H_{54}N_4O_8$ 778.932 |

TABLE 1-continued
| | | |
|---|---|---|
| Vincristine | 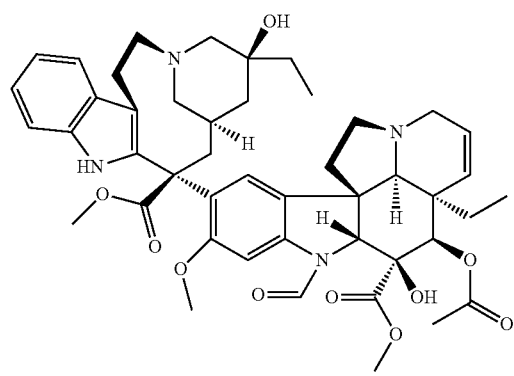 | $C_{46}H_{56}N_4O_{10}$<br>824.958 |
| Vindesine | 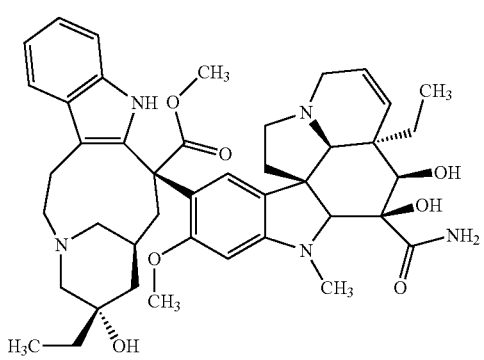 [SMILES: CC[C@]1(O)C[C@H]2CN(CCc3c([nH]c4ccccc34)[C@@](C(=O)OC)(c3cc4c(cc3OC)N(C)C3[C@]45CCN4CC=C[C@@](CC)([C@@H](O)[C@]3(O)C(N)=O)[C@H]45)C2)C1] | $C_{43}H_{55}N_5O_7$<br>753.926 |
Anthracyclins
| Anthracyclin | Chemical Structure | Formula<br>Molecular weight |
|---|---|---|
| Daunorubicin | 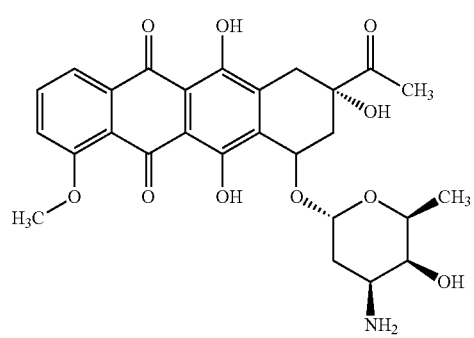 [SMILES: COc1cccc2c1C(=O)c1c(O)c3c(c(O)c1C2=O)C[C@@](O)(C(C)=O)CC3O[C@H]1C[C@H](N)[C@H](O)[C@H](C)O1] | $C_{27}H_{29}NO_{10}$<br>527.52 |
| Doxorubicin | 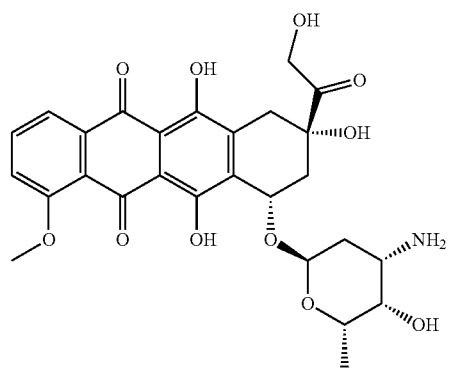 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] | $C_{27}H_{29}NO_{11}$<br>543.52 |

TABLE 1-continued
| | | |
|---|---|---|
| Epirubicin | 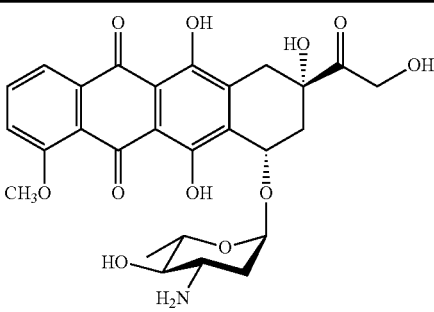 | $C_{27}H_{29}NO_{11}$<br>543.519 |
| Idarubicin | 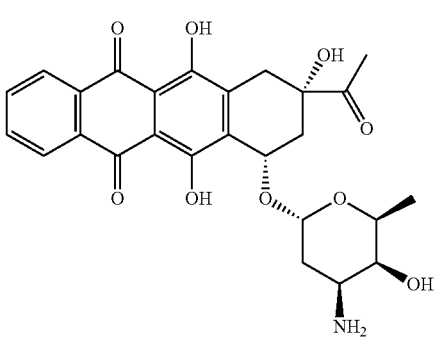 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O] | $C_{26}H_{27}NO_9$<br>497.494 |
| Valrubicin | 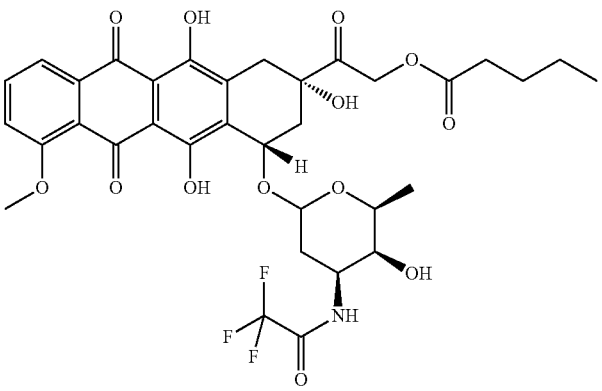 [SMILES: CCCCC(=O)OCC(=O)[C@]1(O)Cc2c(O)c3c(c(O)c2[C@@H](OC2C[C@H](NC(=O)C(F)(F)F)[C@H](O)[C@H](C)O2)C1)C(=O)c1c(OC)cccc1C3=O] | $C_{34}H_{36}F_3NO_{13}$<br>723.644 |
| Antimetabolites | | |
|---|---|---|
| A. Pyrimidine Compound | Chemical Structure | Formula<br>Molecular weight |
| 5-fluorouracil (5-FU) | 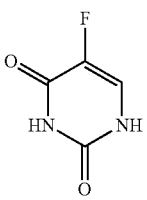 | $C_4H_3FN_2O_2$<br>130.077 |
| Arabinosylcytosine | 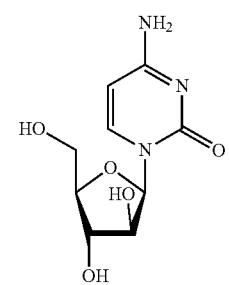 | $C_9H_{13}N_3O_5$<br>243.217 |

TABLE 1-continued

| | | Formula Molecular weight |
|---|---|---|
| Capecitabine | (structure) | $C_{15}H_{22}FN_3O_6$ 359.35 |
| Gemcitabine | (structure) | $C_9H_{11}F_2N_3O_4$ 263.198 |
| Decitabine | (structure) | $C_8H_{12}N_4O_4$ 228.206 |

| B. Purine Compound | Chemical Structure | Formula Molecular weight |
|---|---|---|
| Fludarabine | (structure) | $C_{10}H_{13}FN_5O_7P$ 365.212 |
| 6-Mercaptopurine | (structure) | $C_5H_4N_4S$ 152.177 |

TABLE 1-continued

| C. Folate Antagonist Class | Chemical Structure | Formula Molecular weight |
|---|---|---|
| Methotrexate | 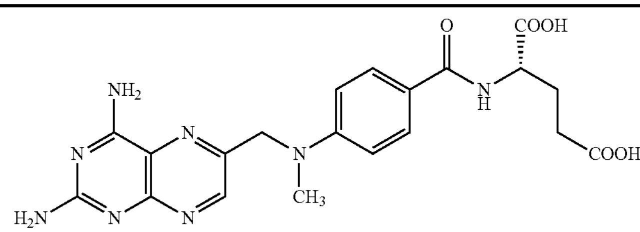 | $C_{20}H_{22}N_8O_5$ 454.44 |

| Aromatase Inhibitors | | |
|---|---|---|
| Aromatase Inhibitor | Chemical Structure | Formula Molecular weight |
| Anastrozole | | $C_{17}H_{19}N_5$ 293.366 |
| Exemestane | | $C_{20}H_{24}O_2$ 296.403 |
| Letrozole | | $C_{17}H_{11}N_5$ 285.303 |
| Tamoxifen | | $C_{26}H_{29}NO$ 371.515 |
| Formestane | | $C_{19}H_{26}O_3$ 302.408 |

TABLE 1-continued
| Topoisomerase Inhibitors | | |
|---|---|---|
| A. Topoisomerase I Inhibitor | Chemical Structure | Formula<br>Molecular weight |
| Camptothecin | 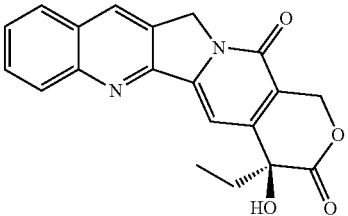 [SMILES: CC[C@@]1(O)C(=O)OCc2c1cc1n(c2=O)Cc2cc3ccccc3nc2-1] | $C_{20}H_{16}N_2O_4$<br>348.352 |
| Topotecan | 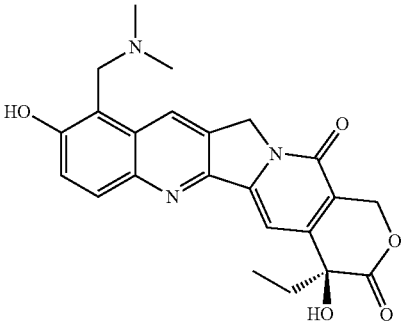 [SMILES: CC[C@@]1(O)C(=O)OCc2c1cc1n(c2=O)Cc2cc3c(CN(C)C)c(O)ccc3nc2-1] | $C_{23}H_{23}N_3O_5 \cdot HCl$<br>457.9 |
| Irinotecan | 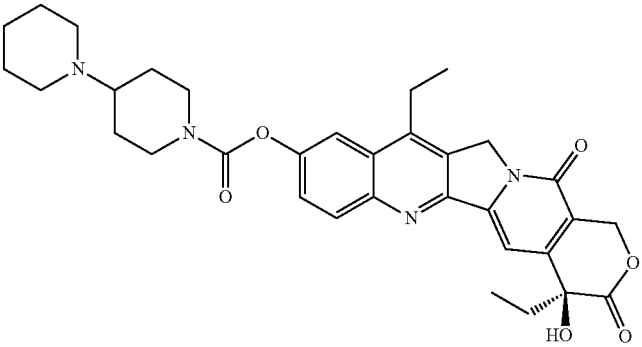 [SMILES: CCc1c2c(nc3ccc(OC(=O)N4CCC(N5CCCCC5)CC4)cc13)-c1cc3c(c(=O)n1C2)COC(=O)[C@]3(O)CC] | $C_{33}H_{38}N_4O_6$<br>623.139 |
| Rubitecan | 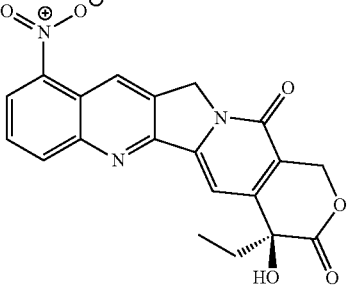 | $C_{20}H_{15}N_3O_6$<br>393.349 |

TABLE 1-continued
| | | |
|---|---|---|
| Lurtotecan | 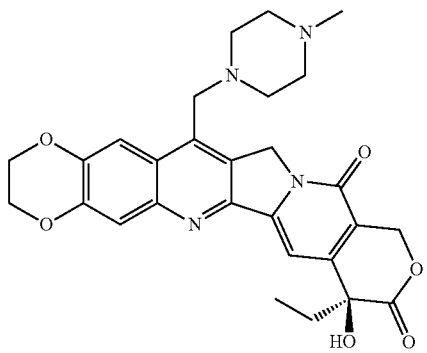 [SMILES: CC[C@@]1(O)C(=O)OCc2c1cc1n(c2=O)Cc2c-1nc1cc3c(cc1c2CN1CCN(C)CC1)OCCO3] | $C_{28}H_{30}N_4O_6$<br>518.561 |
| Exatecan | 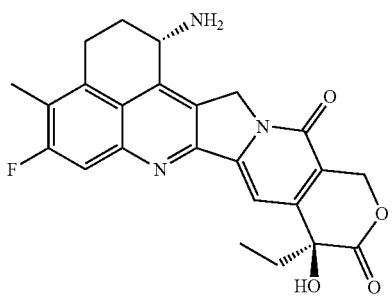 [SMILES: CC[C@@]1(O)C(=O)OCc2c1cc1n(c2=O)Cc2c-1nc1cc(F)c(C)c3c1c2[C@@H](N)CC3] | $C_{24}H_{22}FN_3O_4$<br>435.447583 |
| Belotecan | 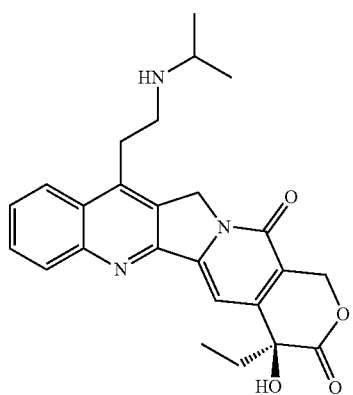 [SMILES: CC[C@@]1(O)C(=O)OCc2c1cc1n(c2=O)Cc2c-1nc1ccccc1c2CCNC(C)C] | $C_{25}H_{27}N_3O_4$<br>433.50 |
| B. Topoisomerase II Inhibitor | Chemical Structure | Formula<br>Molecular weight |
|---|---|---|
| Doxorubicin | see a above | see above |
| Etoposides | 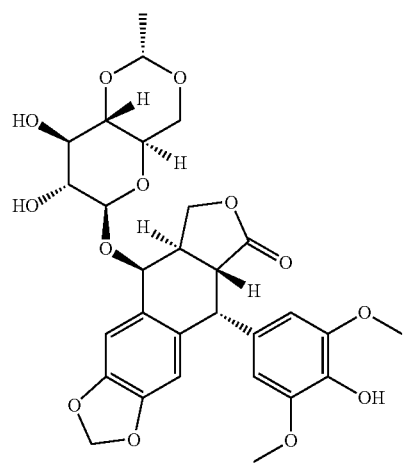 | $C_{29}H_{32}O_{13}$<br>588.557 |

TABLE 1-continued
| Mitoxantrone | 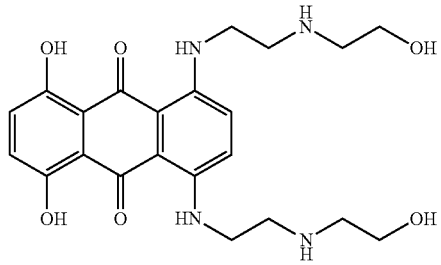 [SMILES: O=C1c2c(O)ccc(O)c2C(=O)c2c(NCCNCCO)ccc(NCCNCCO)c21] | $C_{22}H_{28}N_4O_6$<br>444.481 |
Taxanes
| Taxane | Chemical Structure | Formula<br>Molecular weight |
|---|---|---|
| Paclitaxel | 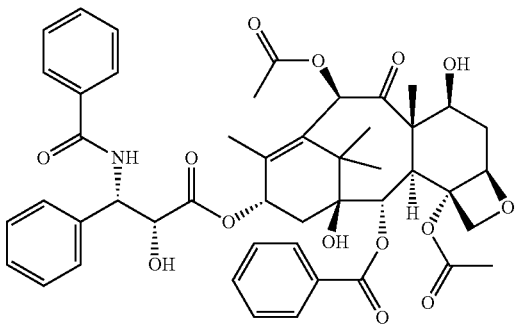 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O] | $C_{47}H_{51}NO_{14}$<br>853.906 |
| Docitaxel | 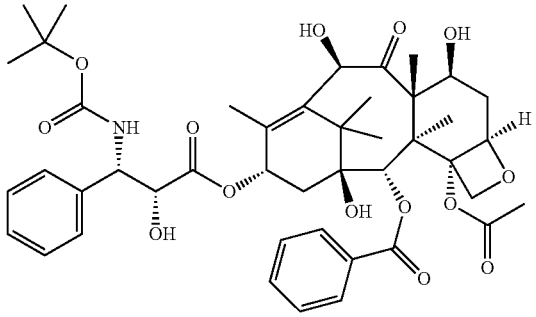 | $C_{43}H_{53}NO_{14}$<br>807.879 |
Platinum Drugs
| Platinum Drug | Chemical Structure | Formula<br>Molecular weight |
|---|---|---|
| Cis-platin | 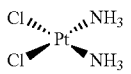 | $[Pt(NH_3)_2Cl_2]$<br>300.01 |
| Carboplatin | 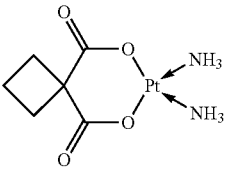 | $C_6H_{12}N_2O_4Pt$<br>371.249 |
| Oxaliplatin | 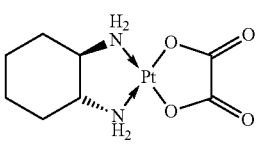 | $C_8H_{14}N_2O_4Pt$<br>397.2858 |

Functional agents can include, but are not limited to, genomic drugs such as those listed in Table 2 and pharmaceutically acceptable salts thereof, as well as phosphates thereof.

TABLE 2

Exemplary Non-Limiting Examples of Genomic Drugs for Conjugation to TAT Oligomers
BRAC1 and BRAC2

| Compound | Chemical Structure | Formula Molecular weight |
|---|---|---|
| AZD1775 (MK-1775) | 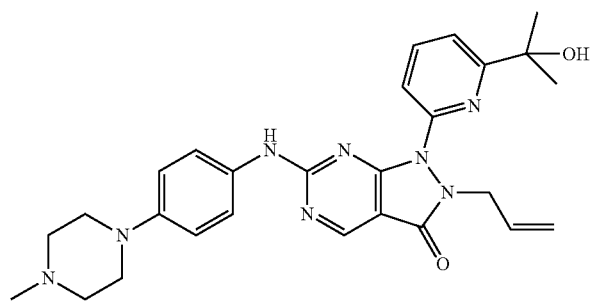 [SMILES: C=CCn1c(=O)c2cnc(Nc3ccc(N4CCN(C)CC4)cc3)nc2n1-c1cccc(C(C)(C)O)n1] | $C_{27}H_{32}N_8O_2$ 500.6 |

Receptor Tyrosine Kinase

| Compound | Chemical Structure | Formula Molecular weight |
|---|---|---|
| Imatinib (GLEEVEC) (also imatinib mesylate) | 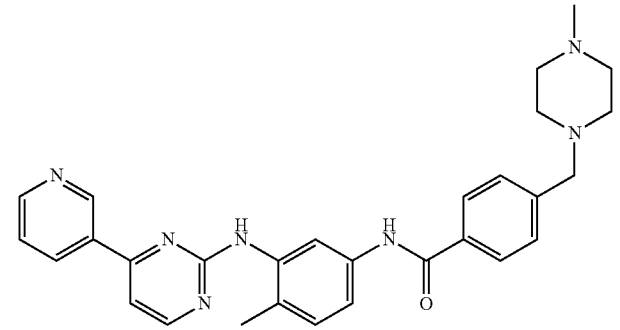 [SMILES: Cc1ccc(NC(=O)c2ccc(CN3CCN(C)CC3)cc2)cc1Nc1nccc(-c2cccnc2)n1] | $C_{29}H_{31}N_7O$ 493.603 |
| Gefitinib (also gefitinib hydrochloride) | 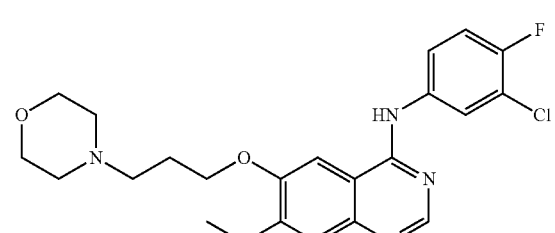 | $C_{22}H_{24}ClFN_4O_3$ 446.902 |
| WZ4002 | 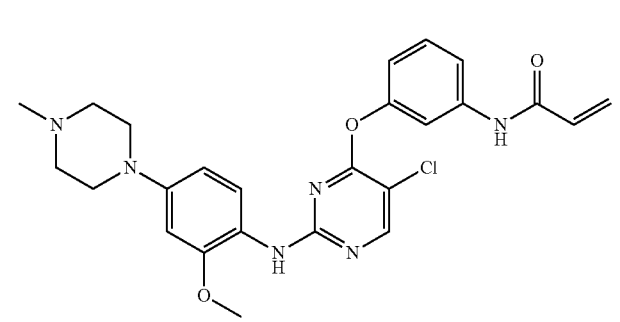 [SMILES: C=CC(=O)Nc1cccc(Oc2nc(Nc3ccc(N4CCN(C)CC4)cc3OC)ncc2Cl)c1] | $C_{25}H_{27}ClN_6O_3$ 495.0 |

TABLE 2-continued
| | | |
|---|---|---|
| AZD9291 (osimertinib) | 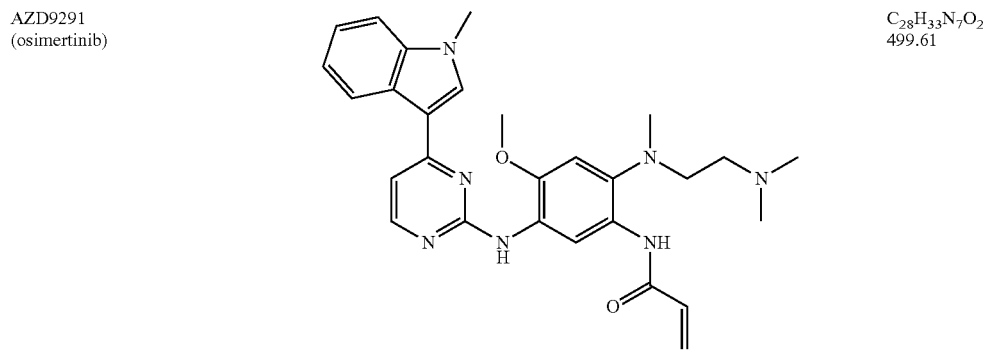 | C₂₈H₃₃N₇O₂ 499.61 |
| Toceranib (also toceranib phosphate) | 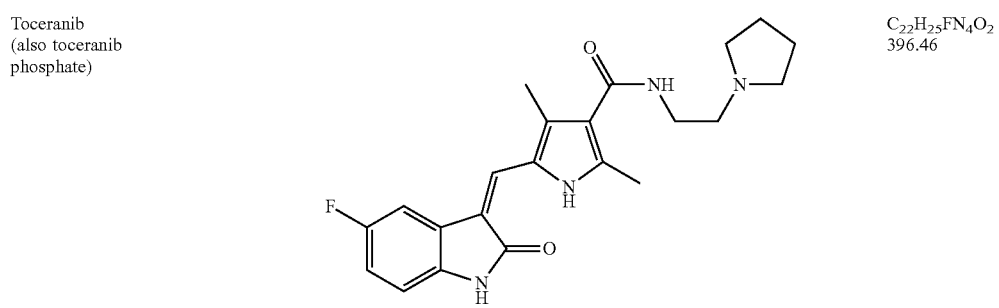 | C₂₂H₂₅FN₄O₂ 396.46 |
| Erlotinib (also elotinib mesylate) | 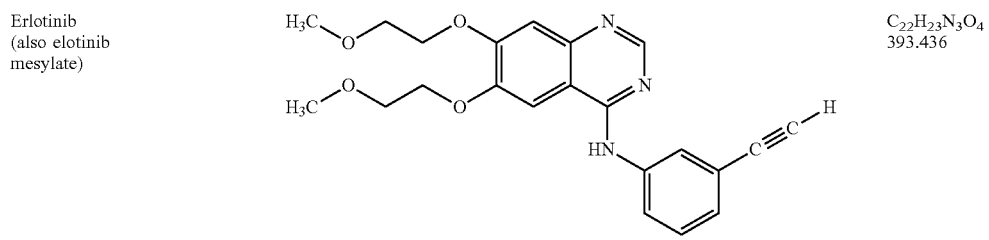 | C₂₂H₂₃N₃O₄ 393.436 |
| Lapatinib | 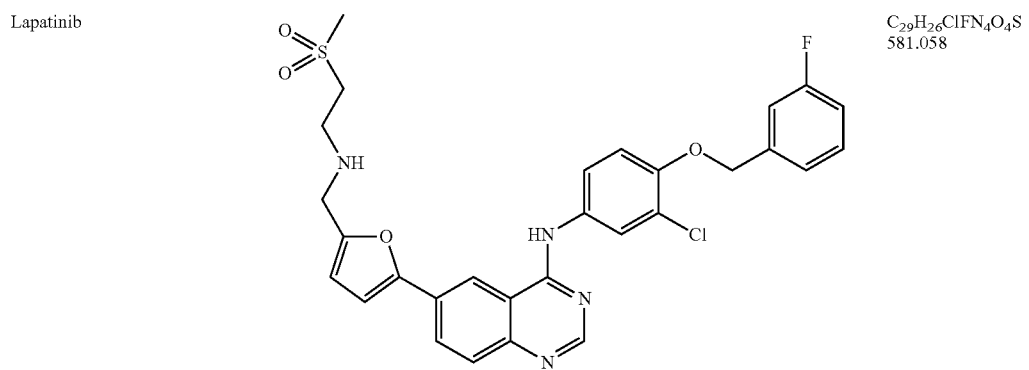 | C₂₉H₂₆ClFN₄O₄S 581.058 |
| Sunitinib | 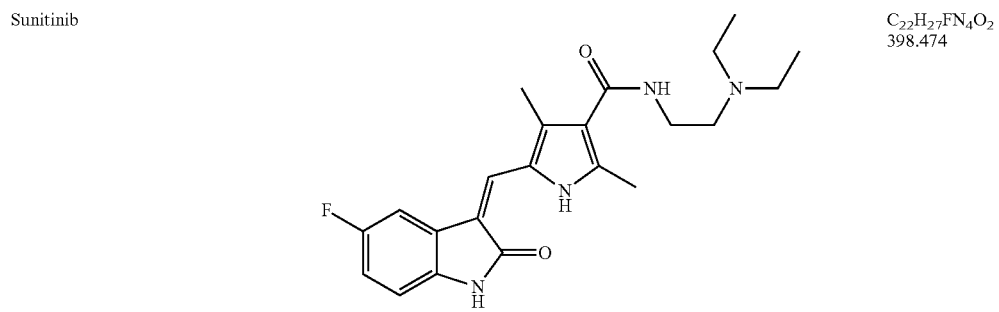 | C₂₂H₂₇FN₄O₂ 398.474 |

TABLE 2-continued
| | | |
|---|---|---|
| AST003 (Sunitinib prodrug) | | |
| N-desethyl sunitinib | 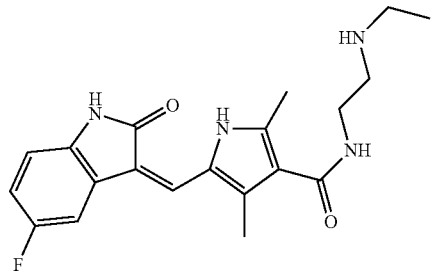 [SMILES: CCNCCNC(=O)c1c(C)[nH]c(/C=C2\C(=O)Nc3ccc(F)cc32)c1C] | $C_{20}H_{23}FN_4O_2$<br>370.42 |
| Sorafenib | 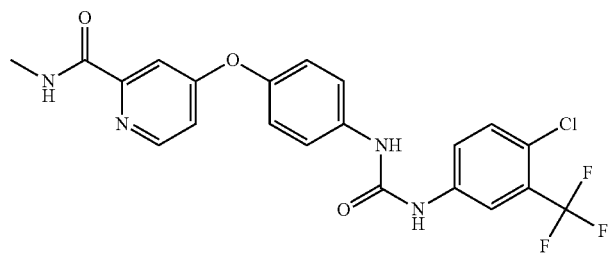 [SMILES: CNC(=O)c1cc(Oc2ccc(NC(=O)Nc3ccc(Cl)c(C(F)(F)F)c3)cc2)ccn1] | $C_{21}H_{16}ClF_3N_4O_3$<br>464.825 |
| Nilotinib | 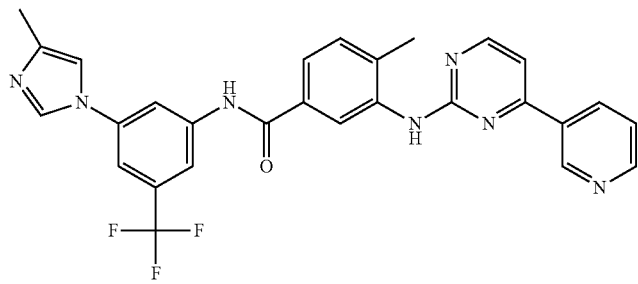 [SMILES: Cc1cn(-c2cc(NC(=O)c3ccc(C)c(Nc4nccc(-c5cccnc5)n4)c3)cc(C(F)(F)F)c2)cn1] | $C_{28}H_{22}F_3N_7O$<br>529.5245 |
| Bosutinib | 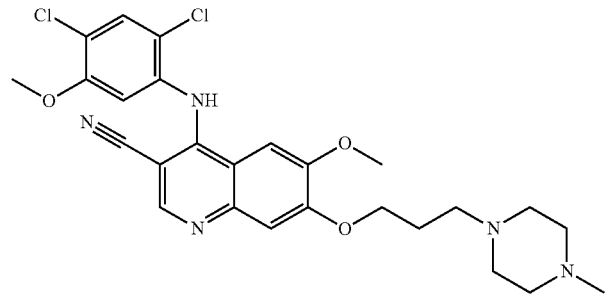 | $C_{26}H_{29}Cl_2N_5O_3$<br>530.446 |
| Neratinib | 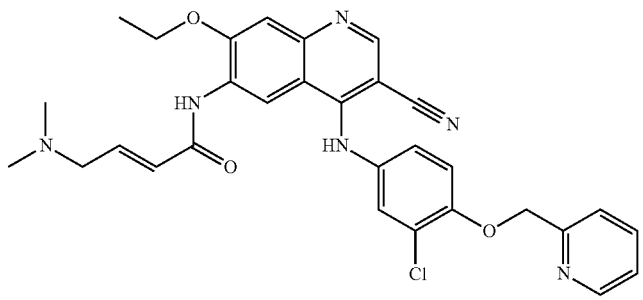 [SMILES: CCOc1cc2ncc(C#N)c(Nc3ccc(OCc4ccccn4)c(Cl)c3)c2cc1NC(=O)/C=C/CN(C)C] | $C_{30}H_{29}ClN_6O_3$<br>557.04 |

TABLE 2-continued

| Vatalanib | 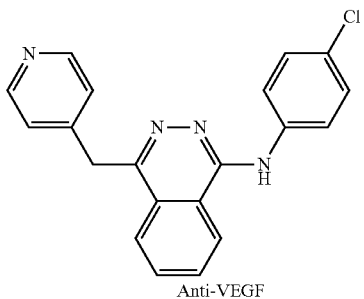 | $C_{20}H_{15}ClN_4$ 346.813 |

Anti-VEGF

| Compound | Chemical Structure | Formula Molecular weight |
|---|---|---|
| Bevacizumab | Monoclonal Antibody | $C_{6638}H_{10160}N_{1720}O_{2108}S_{44}$ 150 kg/mol |
| Aflibercept | Monoclonal Antibody | $C_{4318}H_{6788}N_{1164}O_{1304}S_{32}$ 96 kg/mol |

Anti-VEGFR

| Compound | Chemical Structure | Formula Molecular weight |
|---|---|---|
| Vatalanib | see above | see above |
| Motesanib | 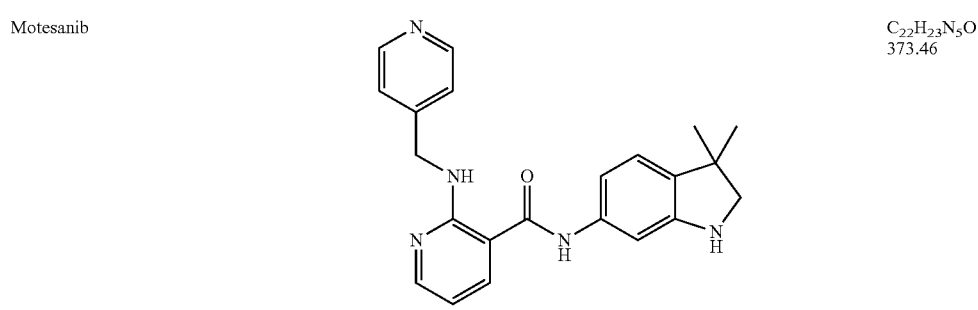 | $C_{22}H_{23}N_5O$ 373.46 |
| Pazopanib | 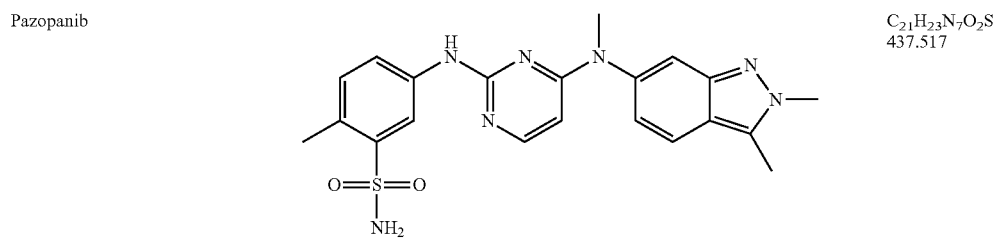 | $C_{21}H_{23}N_7O_2S$ 437.517 |
| Cediranib | 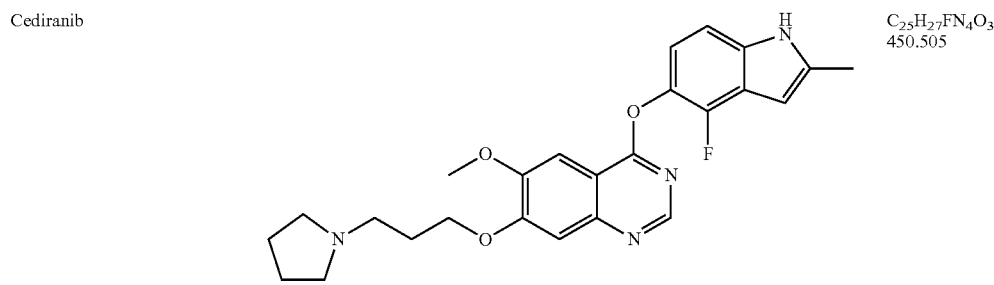 | $C_{25}H_{27}FN_4O_3$ 450.505 |
| Semaxinib | 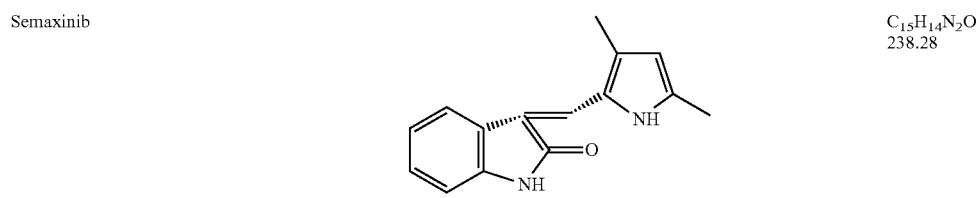 | $C_{15}H_{14}N_2O$ 238.28 |

TABLE 2-continued

| Vatalanib 2HCl | 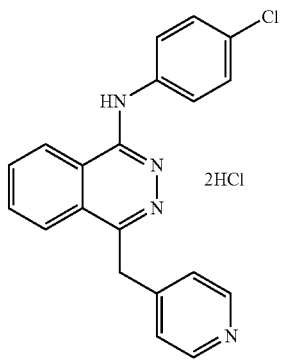 [SMILES: Clc1ccc(Nc2nnc(Cc3ccncc3)c3ccccc23)cc1] | $C_{20}H_{17}Cl_3N_4$<br>419.7 |
|---|---|---|
| Sorafenib:Nexavar | 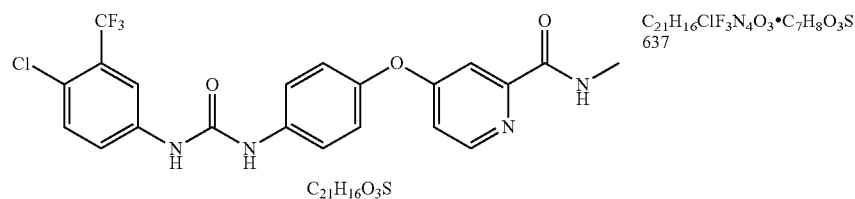 | $C_{21}H_{16}ClF_3N_4O_3 \cdot C_7H_8O_3S$<br>637 |

| HGF (Hepatocyte Growth Factor) | | |
|---|---|---|
| Compound | Chemical Structure | Formula<br>Molecular weight |
| Rilotumumab | Monoclonal Antibody | $C_{6464}H_{9932}N_{1708}O_{2010}S_{46}$<br>145.2 kg/mol |

| Human Epidermal Growth Factor | | |
|---|---|---|
| Compound | Chemical Structure | Formula<br>Molecular weight |
| HER mAb | Monoclonal Antibody | |
| Panitumumab | Monoclonal Antibody | $C_{6398}H_{9878}N_{1694}O_{2016}S_{48}$<br>144 kg/mol |
| Trastuzumab | Monoclonal Antibody | $C_{6470}H_{10012}N_{1726}O_{2013}S_{42}$<br>145 kg/mol |
| Pertuzumab | Monoclonal Antibody | |

| Anti-HER | | |
|---|---|---|
| Compound | Chemical Structure | Formula<br>Molecular weight |
| Lapatinib | see above | see above |
| Afatinib | 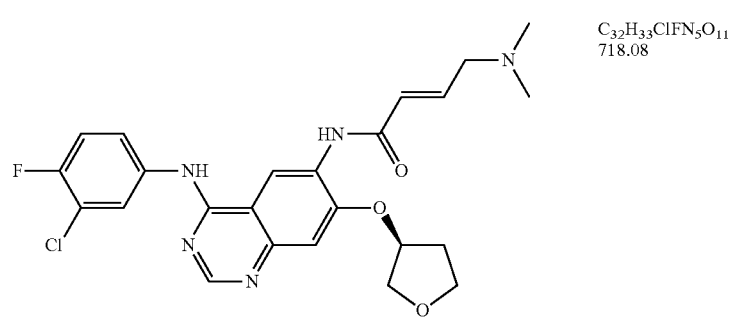 | $C_{32}H_{33}ClFN_5O_{11}$<br>718.08 |

TABLE 2-continued
Anti-Ras
| Compound | Chemical Structure | Formula<br>Molecular weight |
|---|---|---|
| Tipifarnib | 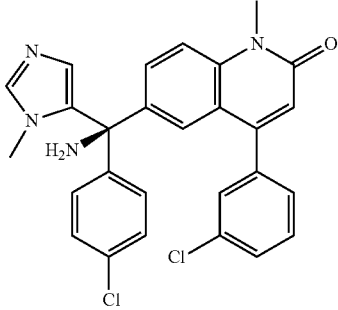 [SMILES: Cn1cncc1[C@@](N)(c1ccc(Cl)cc1)c1ccc2c(c1)c(-c1cccc(Cl)c1)cc(=O)n2C] | $C_{27}H_{22}Cl_2N_4O$<br>489.4 |
| Lonafarnib | 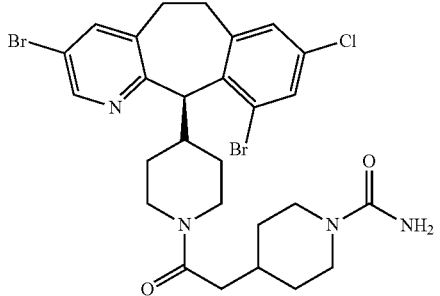 [SMILES: NC(=O)N1CCC(CC(=O)N2CCC([C@H]3c4ncc(Br)cc4CCc4cc(Cl)cc(Br)c43)CC2)CC1] | $C_{27}H_{31}Br_2ClN_4O_2$<br>638.82164 |
Anti-Raf
| Compound | Chemical Structure | Formula<br>Molecular weight |
|---|---|---|
| Sorafenib | see above | see above |
| XL281 | 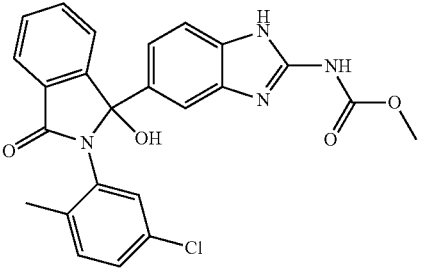 [SMILES: COC(=O)Nc1nc2cc(C3(O)c4ccccc4C(=O)N3c3cc(Cl)ccc3C)ccc2[nH]1] | $C_{24}H_{19}ClN_4O_4$<br>462.89 |
Anti-MEK
| Compound | Chemical Structure | Formula<br>Molecular weight |
|---|---|---|
| Selumetinib | 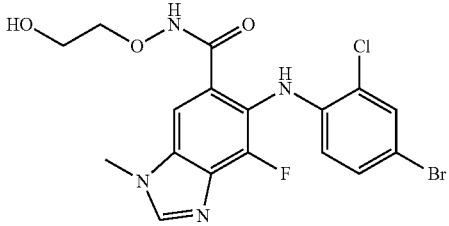 [SMILES: Cn1cnc2c(F)c(Nc3ccc(Br)cc3Cl)c(C(=O)NOCCO)cc21] | $C_{17}H_{15}BrClFN_4O_3$<br>457.68 g/mol |

TABLE 2-continued
Anti-SRC
| Compound | Chemical Structure | Formula Molecular weight |
|---|---|---|
| XL999 | Not available | Not available |
| AZD0530 | 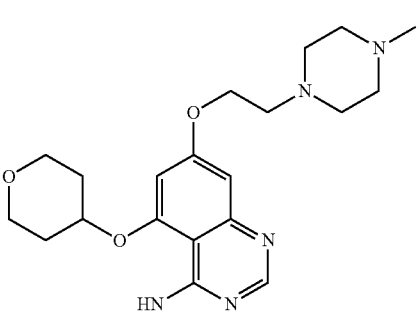 | $C_{27}H_{32}ClN_5O_5$ 542.025 |
PI3K (Pan-class 1 PI3K Inhibitors)
| A. Pan-class 1 PI3K Inhibitor | Chemical Structure | Formula Molecular weight |
|---|---|---|
| GDC-0941 | 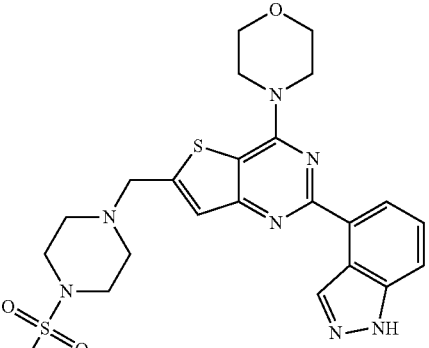 | $C_{23}H_{27}N_7O_3S_2$ 513.64 |
| Idelalisib | 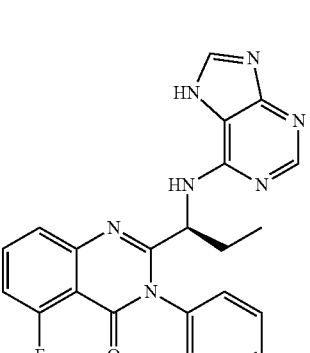 | $C_{22}H_{18}FN_7O$ 415.4 |

TABLE 2-continued
| Buparlisib | 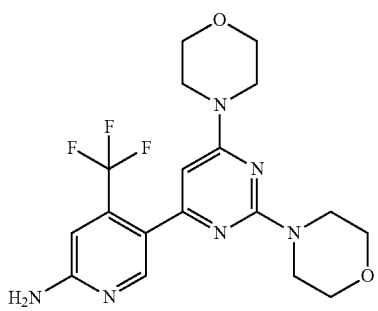 [SMILES: Nc1cc(C(F)(F)F)c(-c2cc(N3CCOCC3)nc(N3CCOCC3)n2)cn1] | $C_{18}H_{21}F_3N_6O_2$<br>410.4 |
| Copanlisib | 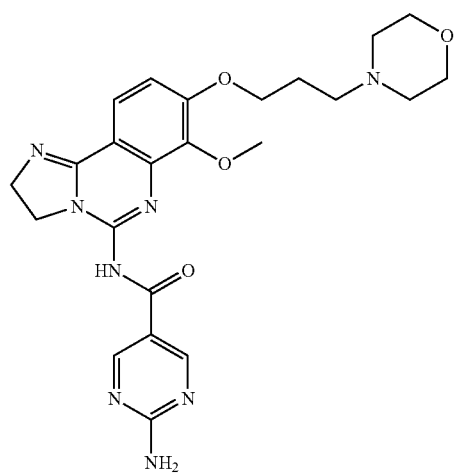 [SMILES: COc1c(OCCCN2CCOCC2)ccc2c1N=C(NC(=O)c1cnc(N)nc1)N1CCN=C21] | $C_{23}H_{28}N_8O_4$<br>480.2 |
| Pilaralisib | 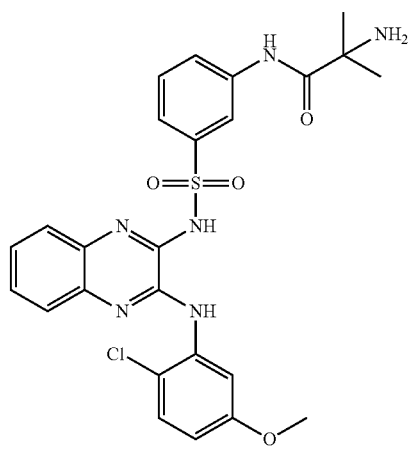 [SMILES: COc1ccc(Cl)c(Nc2nc3ccccc3nc2NS(=O)(=O)c2cccc(NC(=O)C(C)(C)N)c2)c1] | $C_{25}H_{25}ClN_6O_4S$<br>541.02 |
| PX866 | 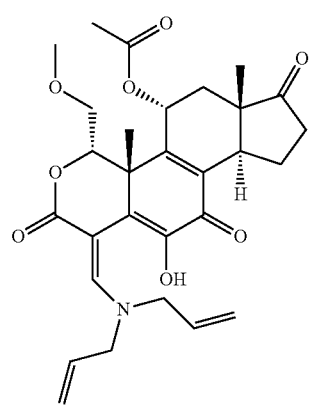 [SMILES: C=CCN(/C=C1/C(=O)O[C@H](COC)[C@@]2(C)C1=C(O)C(=O)C1=C2[C@H](OC(C)=O)C[C@]2(C)C(=O)CC[C@@H]12)CC=C] | $C_{29}H_{35}NO_8$<br>525.2 |

TABLE 2-continued
| | | |
|---|---|---|
| ZSTK474 | 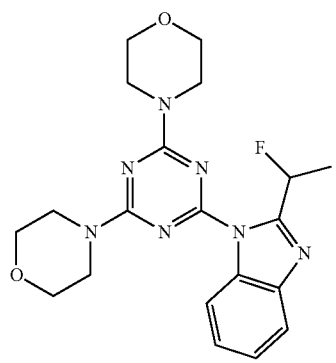 [SMILES: CC(F)c1nc2ccccc2n1-c1nc(N2CCOCC2)nc(N2CCOCC2)n1] | $C_{19}H_{21}F_2N_7O_2$<br>417.4 |
| CH5132799 | 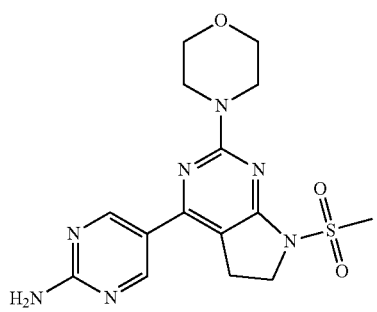 [SMILES: CS(=O)(=O)N1CCc2c(-c3cnc(N)nc3)nc(N3CCOCC3)nc21] | $C_{15}H_{19}N_7O_3S$<br>377.42 |
| B. Isoform specific PI3K Inhibitor | Chemical Structure | Formula<br>Molecular weight |
| Taselisib | 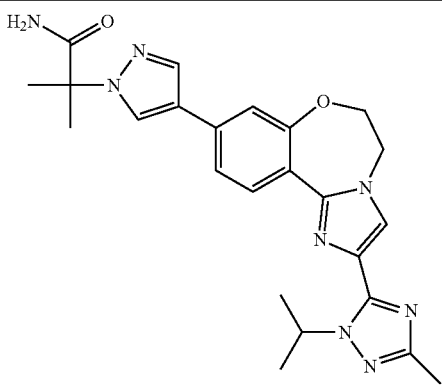 | $C_{24}H_{28}N_8O_2$<br>460.53 |
| Alpelisib | 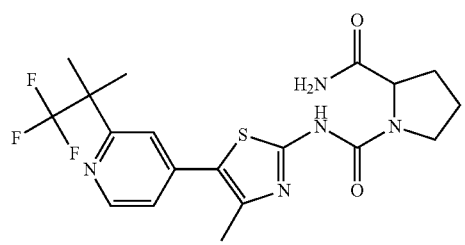 [SMILES: Cc1nc(NC(=O)N2CCCC2C(N)=O)sc1-c1ccnc(C(C)(C)C(F)(F)F)c1] | $C_{19}H_{22}F_3N_5O_2S$<br>441.5 |
| Serabelisib | 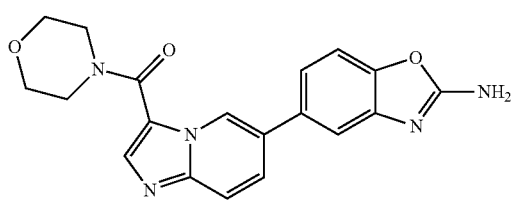 [SMILES: Nc1nc2cc(-c3ccc4ncc(C(=O)N5CCOCC5)n4c3)ccc2o1] | $C_{19}H_{17}N_5O_3$<br>363.13 |

TABLE 2-continued
| | | |
|---|---|---|
| BAY1082439 | 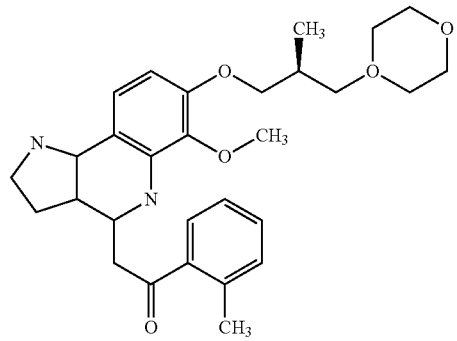 | |
| CH5132799 | 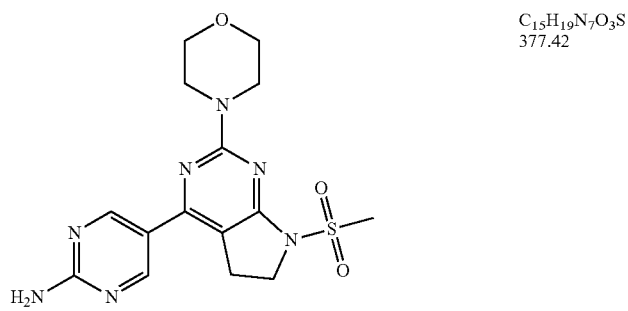 | $C_{15}H_{19}N_7O_3S$<br>377.42 |
| GSK2636771 | 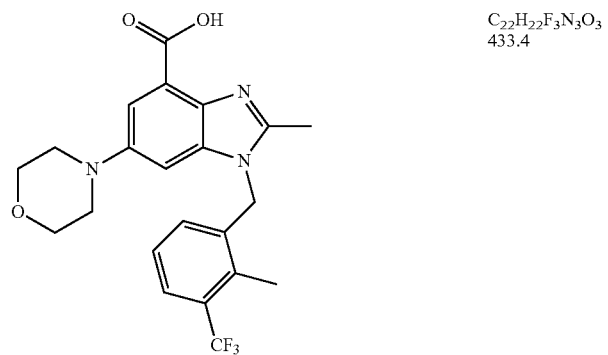 | $C_{22}H_{22}F_3N_3O_3$<br>433.4 |
| AZD8186 | 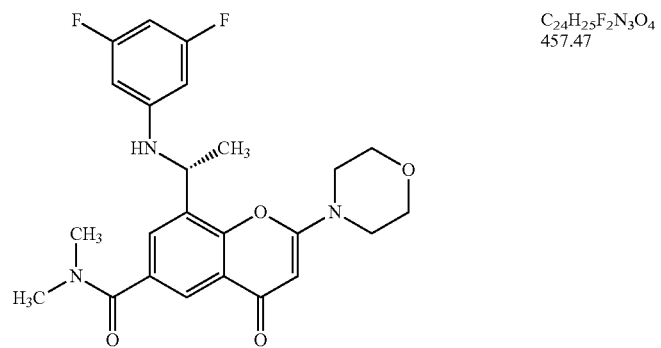 | $C_{24}H_{25}F_2N_3O_4$<br>457.47 |
| SAR260301 | 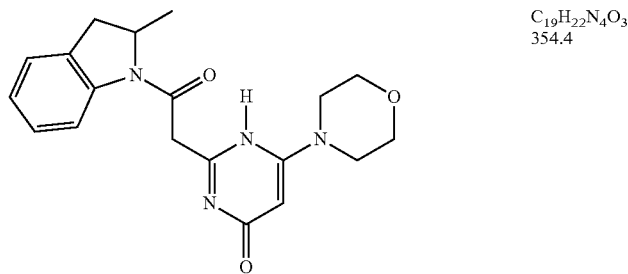 | $C_{19}H_{22}N_4O_3$<br>354.4 |

TABLE 2-continued

| | Chemical Structure | Formula Molecular weight |
|---|---|---|
| Idelalisib | See above | See above |
| Duvelisib | 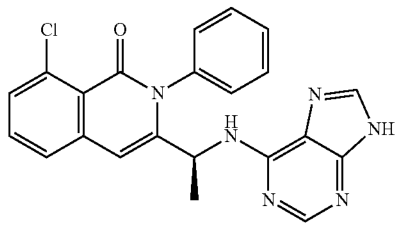 [SMILES: C[C@H](Nc1ncnc2[nH]cnc12)c1cc2cccc(Cl)c2c(=O)n1-c1ccccc1] | $C_{22}H_{17}ClN_6O$ <br> 416.86 |
| AMG319 | 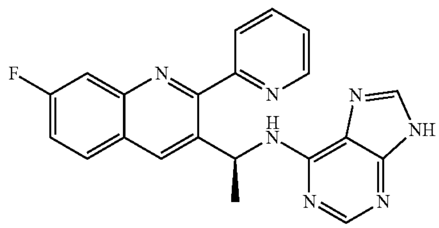 [SMILES: C[C@H](Nc1ncnc2[nH]cnc12)c1cc2ccc(F)cc2nc1-c1ccccn1] | $C_{21}H_{16}FN_7$ <br> 385.4 |

| C. Dual-specificity PI3K/mTOR Inhibitor | Chemical Structure | Formula Molecular weight |
|---|---|---|
| Dactolisib | 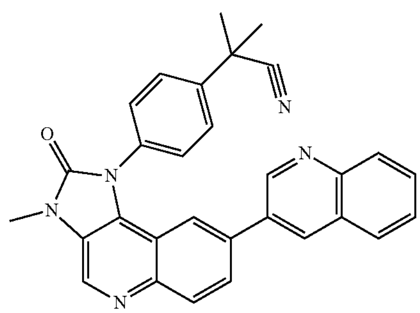 [SMILES: Cn1c(=O)n(-c2ccc(C(C)(C)C#N)cc2)c2c3cc(-c4cnc5ccccc5c4)ccc3ncc21] | $C_{30}H_{23}N_5O$ <br> 469.6 |
| GDC-0980 | 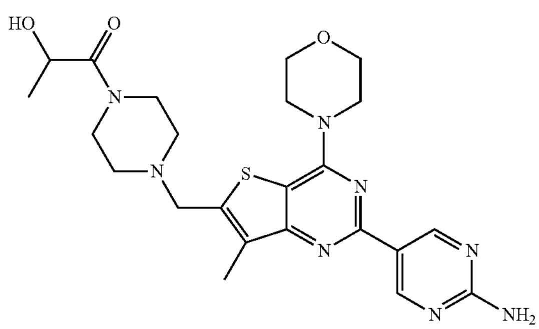 [SMILES: Cc1c(CN2CCN(C(=O)C(C)O)CC2)sc2c(N3CCOCC3)nc(-c3cnc(N)nc3)nc12] | $C_{23}H_{30}N_8O_3S$ <br> 498.6 |
| Gedatolisib | 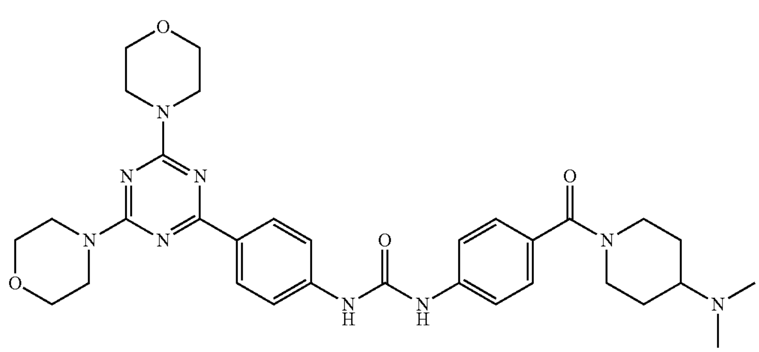 [SMILES: CN(C)C1CCN(C(=O)c2ccc(NC(=O)Nc3ccc(-c4nc(N5CCOCC5)nc(N5CCOCC5)n4)cc3)cc2)CC1] | |

TABLE 2-continued
PF-04691502
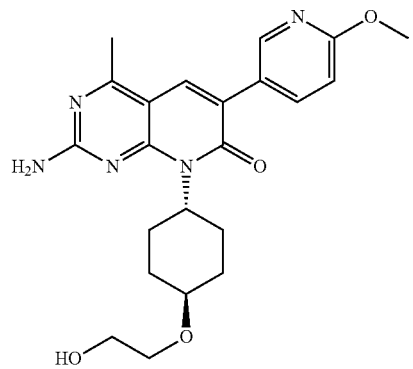 [SMILES: COc1ccc(-c2cc3c(C)nc(N)nc3n([C@H]3CC[C@H](OCCO)CC3)c2=O)cn1]
C$_{22}$H$_{27}$N$_5$O$_4$
425.5
GSK-2126458
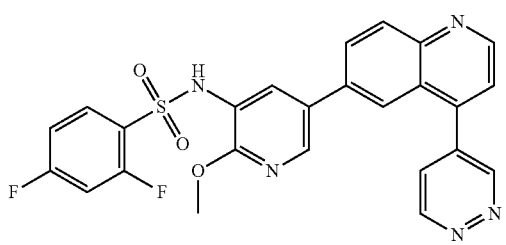 [SMILES: COc1ncc(-c2ccc3nccc(-c4ccnnc4)c3c2)cc1NS(=O)(=O)c1ccc(F)cc1F]
C$_{25}$H$_{17}$F$_2$N$_5$O$_3$S
505.5
SAR245409
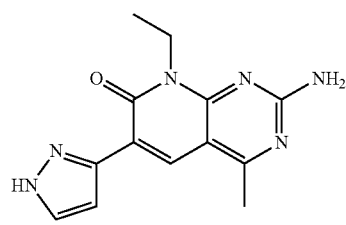 [SMILES: CCn1c(=O)c(-c2cc[nH]n2)cc2c(C)nc(N)nc21]
C$_{13}$H$_{14}$N$_6$O
270.29
| Anti-mTOR | | |
|---|---|---|
| Compound | Chemical Structure | Formula Molecular weight |
| Temsirolimus | 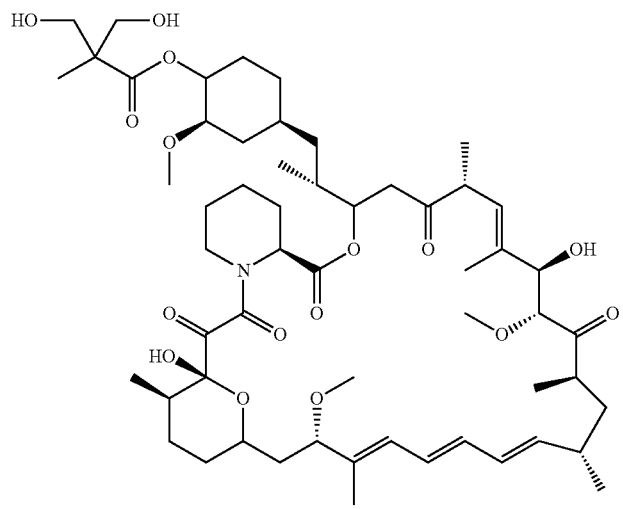 [SMILES: CO[C@H]1CC2CC[C@@H](C)[C@@](O)(O2)C(=O)C(=O)N2CCCC[C@H]2C(=O)OC([C@H](C)C[C@@H]2CCC(OC(=O)C(C)(CO)CO)[C@H](OC)C2)CC(=O)[C@H](C)/C=C(\C)[C@@H](O)[C@@H](OC)C(=O)[C@H](C)C[C@H](C)/C=C/C=C/C=C/1C] | C$_{56}$H$_{87}$NO$_{16}$ 1030.28 |

TABLE 2-continued
| | | |
|---|---|---|
| Everolimus | 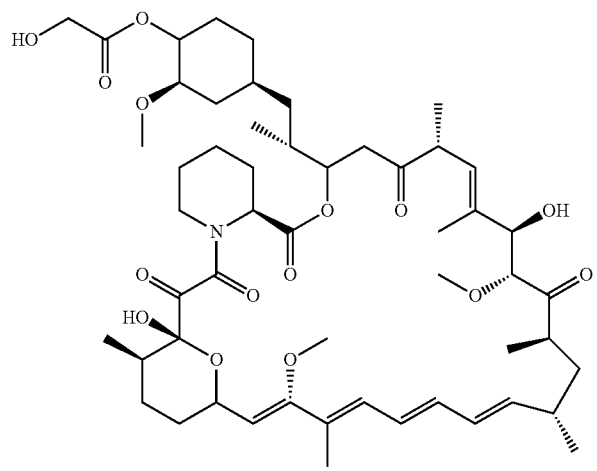 | C₅₃H₈₃NO₁₄<br>958.224 |
| Nap-rapamycin | Nanoparticle albumin bound rapamycin | C₅₁H₇₉NO₁₃<br>914.18 |
| Ridaforolimus | 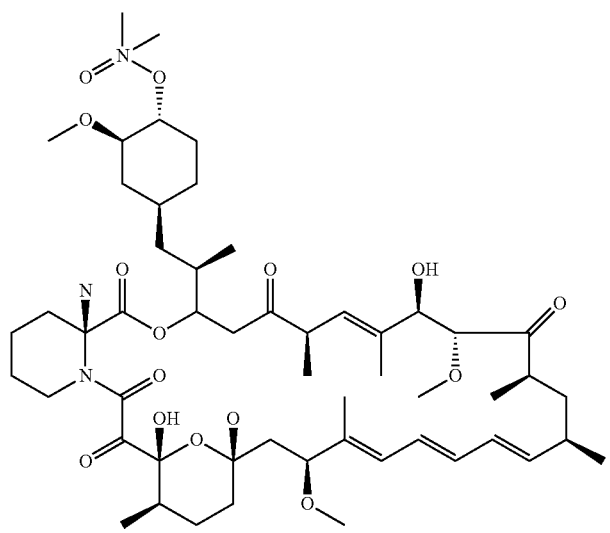 [SMILES: CO[C@H]1C[C@]2(O)CC[C@@H](C)[C@@](O)(O2)C(=O)C(=O)N2CCCC[C@]2(N)C(=O)OC([C@H](C)C[C@@H]2CC[C@@H](O[N+](C)(C)[O-])[C@H](OC)C2)CC(=O)[C@H](C)/C=C(\C)[C@@H](O)[C@@H](OC)C(=O)[C@H](C)C[C@@H](C)/C=C/C=C/C=C/1C] | C₅₃H₈₄NO₁₃P<br>974.23 |
| Sirolimus | 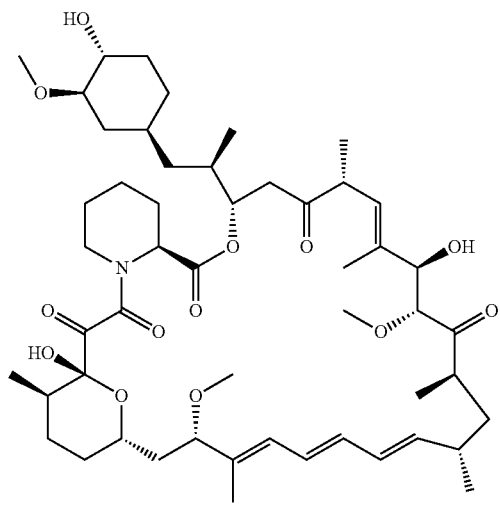 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] | C₅₁H₇₉NO₁₃<br>914.18 |

TABLE 2-continued
OSI-027 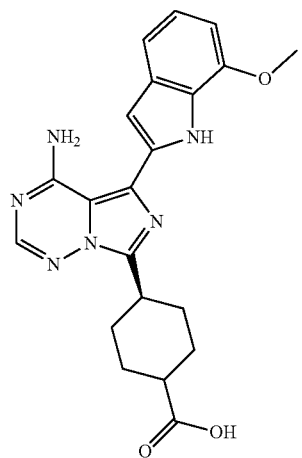 C$_{21}$H$_{22}$N$_6$O$_3$
406.44
Vistusertib 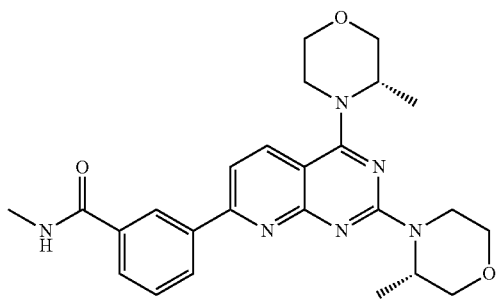 [SMILES: CNC(=O)c1cccc(-c2ccc3c(N4CCOC[C@@H]4C)nc(N4CCOC[C@@H]4C)nc3n2)c1] C$_{25}$H$_{30}$N$_6$O$_3$
462.54
MLN0128 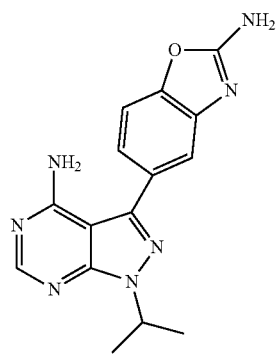 [SMILES: CC(C)n1nc(-c2ccc3oc(N)nc3c2)c2c(N)ncnc21] C$_{15}$H$_{15}$N$_7$O
309.33
Torkinib 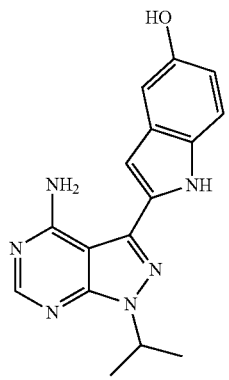 [SMILES: CC(C)n1nc(-c2cc3cc(O)ccc3[nH]2)c2c(N)ncnc21] C$_{16}$H$_{16}$N$_6$O
308.34

TABLE 2-continued

RTK Pathway: EGFR

| Compound | Chemical Structure | Formula Molecular weight |
|---|---|---|
| PF-04948568 | Peptide cancer vaccine | |
| Gefitinib (also gefitinib hydrochloride) | See above | See above |
| Nimotuzumab | Monoclonal Antibody | $C_{6566}H_{10082}N_{1746}O_{2056}S_{40}$ 147,659 |
| OSI-420 | 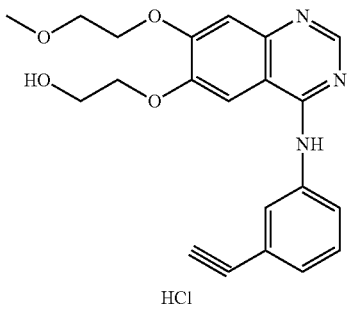 [SMILES: C#Cc1cccc(Nc2ncnc3cc(OCCOC)c(OCCO)cc23)c1 ; Cl] HCl | |

PDGFR (VGFR with secondary PDGFR activity)

| Compound | Chemical Structure | Formula Molecular weight |
|---|---|---|
| Sunitinib | 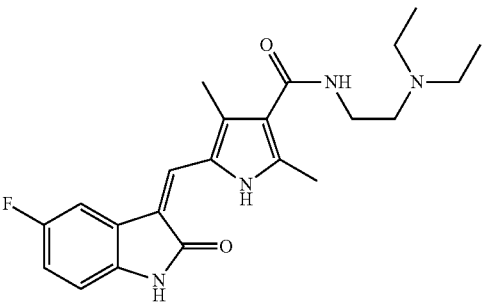 [SMILES: CCN(CC)CCNC(=O)c1c(C)[nH]c(/C=C2\C(=O)Nc3ccc(F)cc32)c1C] | $C_{22}H_{27}FN_4O_2$ 398.474 |
| Dasatinib | 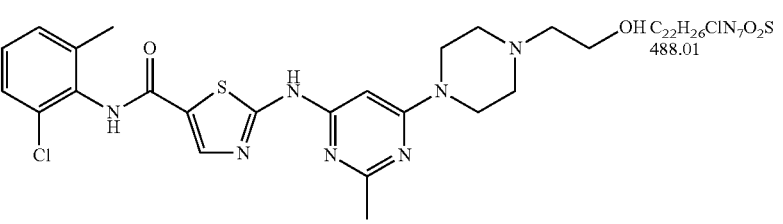 | $C_{22}H_{26}ClN_7O_2S$ 488.01 |

TABLE 2-continued
Integrin
| Compound | Chemical Structure | Formula Molecular weight |
|---|---|---|
| Cilengitide | 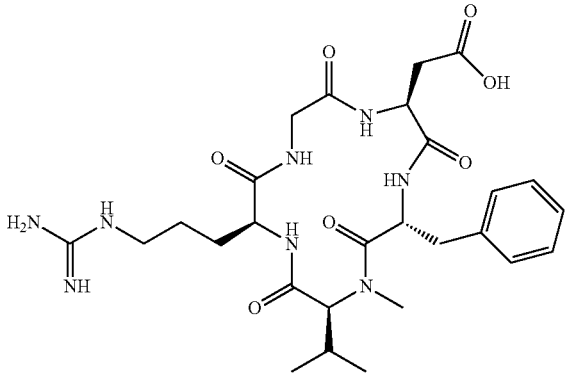 [SMILES: CC(C)[C@H]1C(=O)N[C@@H](CCCNC(=N)N)C(=O)NCC(=O)N[C@@H](CC(=O)O)C(=O)N[C@H](Cc2ccccc2)C(=O)N1C] | $C_{27}H_{40}N_8O_7$ 588.656 |
AKT
| Compound | Chemical Structure | Formula Molecular weight |
|---|---|---|
| Perifosine | 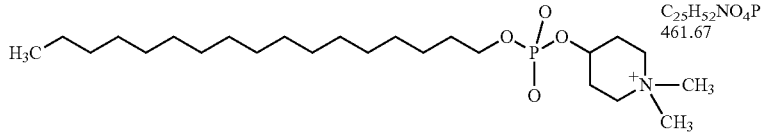 | $C_{25}H_{52}NO_4P$ 461.67 |
HH Pathway
| Compound | Chemical Structure | Formula Molecular weight |
|---|---|---|
| Vismodegib | 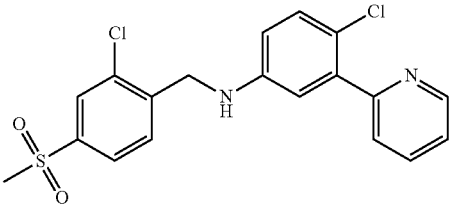 [SMILES: CS(=O)(=O)c1ccc(CNc2ccc(Cl)c(-c3ccccn3)c2)c(Cl)c1] | $C_{19}H_{14}Cl_2N_2O_3S$ 421.30 |
| Sonidegib | 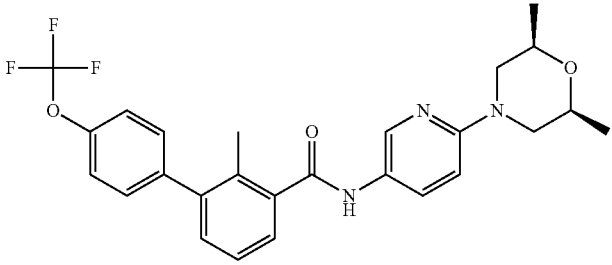 [SMILES: Cc1c(C(=O)Nc2ccc(N3C[C@@H](C)O[C@@H](C)C3)nc2)cccc1-c1ccc(OC(F)(F)F)cc1] | $C_{26}H_{26}F_3N_3O_3$ 485.498 |

TABLE 2-continued
| | | |
|---|---|---|
| BMS-833923 | 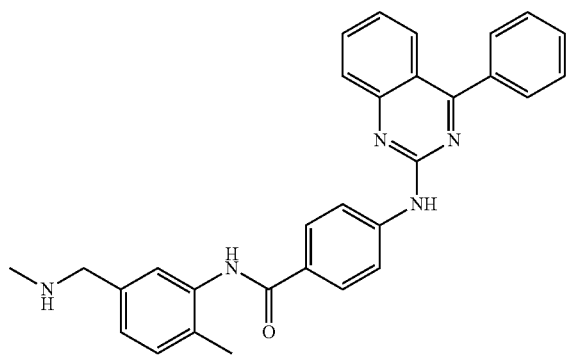 [SMILES: CNCc1ccc(C)c(NC(=O)c2ccc(Nc3nc(-c4ccccc4)c4ccccc4n3)cc2)c1] | $C_{30}H_{27}N_5O$<br>473.57 |
| Glasdegib | 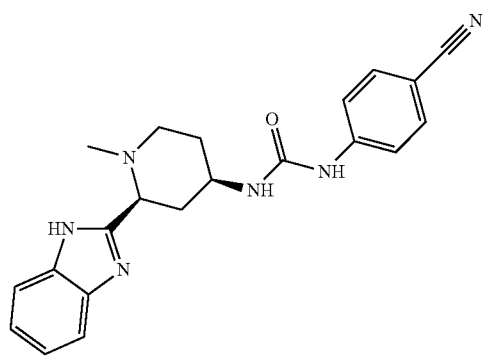 [SMILES: CN1CC[C@@H](NC(=O)Nc2ccc(C#N)cc2)C[C@H]1c1nc2ccccc2[nH]1] | C21H22N6O<br>374.44 |
| Taladegib | 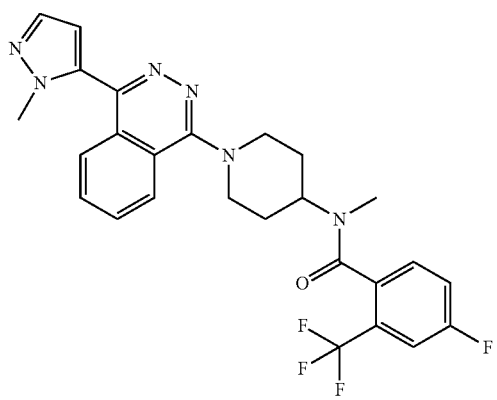 [SMILES: CN(C(=O)c1ccc(F)cc1C(F)(F)F)C1CCN(c2nnc(-c3ccnn3C)c3ccccc23)CC1] | $C_{26}H_{24}F_4N_6O$<br>512.5 |
Notch Pathway
| Compound | Chemical Structure | Formula<br>Molecular weight |
|---|---|---|
| MK0752 | 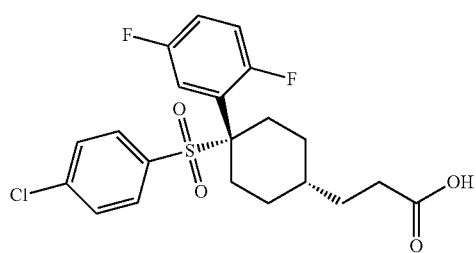 [SMILES: O=C(O)CC[C@H]1CC[C@@](c2cc(F)ccc2F)(S(=O)(=O)c2ccc(Cl)cc2)CC1] | $C_{21}H_{21}ClF_2O_4S$<br>442.9 |

TABLE 2-continued
| | | |
|---|---|---|
| PF-03084014 | 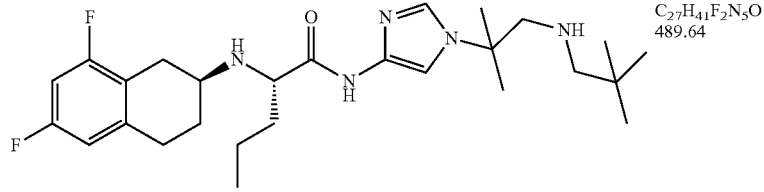 | C₂₇H₄₁F₂N₅O 489.64 |
| BMS-906024 | 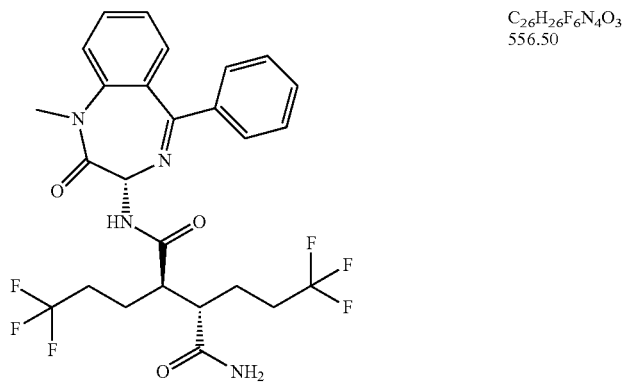 | C₂₆H₂₆F₆N₄O₃ 556.50 |
| Panobinostat | 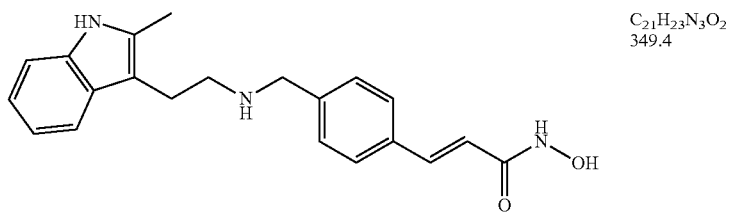 | C₂₁H₂₃N₃O₂ 349.4 |
| MED10639 | Monoclonal Antibody | |
| OMP-21M18 | Monoclonal Antibody | |
| OMP-52M51 | Monoclonal Antibody | |
| OMP-59R5 | Monoclonal Antibody | |
| Resveratrol | 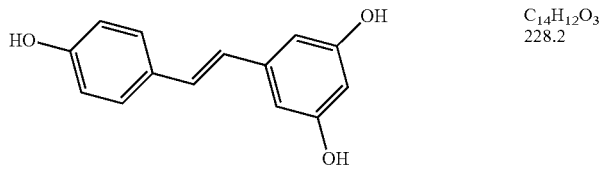 | C₁₄H₁₂O₃ 228.2 |
| RO4929097 | 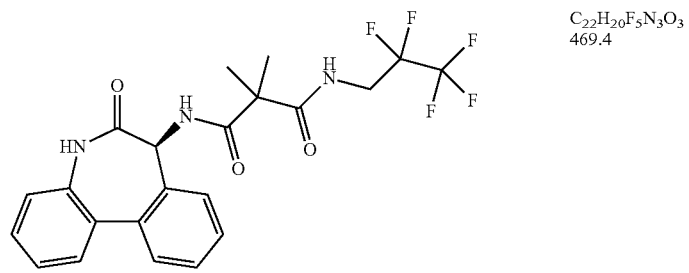 | C₂₂H₂₀F₅N₃O₃ 469.4 |

TABLE 2-continued

WNT Pathway

| Compound | Chemical Structure | Formula Molecular weight |
|---|---|---|
| Celecoxib | 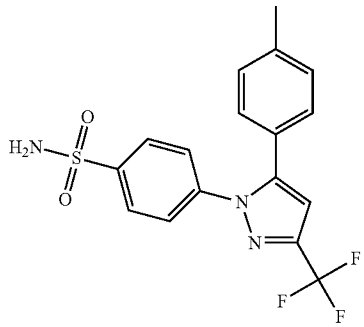 [SMILES: Cc1ccc(-c2cc(C(F)(F)F)nn2-c2ccc(S(N)(=O)=O)cc2)cc1] | $C_{17}H_{14}F_3N_3O_2S$ 381.373 |

In some embodiments, pharmaceutical compositions are provided which can include the peptide conjugates disclosed herein. These pharmaceutical compositions may include pharmaceutically acceptable excipients and additives. The peptide conjugates disclosed herein may also be in the form of pharmaceutically acceptable salts. The functional agent and/or at least a portion of the peptide may be in the form of a pharmaceutically acceptable salt.

In some embodiments, methods are provided for the treatment of cancer in a subject in need thereof which include the steps of administering an anesthetic to a subject to anesthetize the subject, reducing blood flow in the subject to result in transient blood flow arrest, and administering intra-arterially at a locus in the body of the subject a composition comprising a therapeutically effective amount of a peptide conjugate or pharmaceutically acceptable salt thereof of the present disclosure. A "therapeutically effective amount" is an amount that is sufficient to produce a desired therapeutic effect. Such an amount can be determined by one of ordinary skill in the art and can depend on the volume of a tumor. For example, an administered therapeutically effective amount, by way of example but not limitation, can be 1 mg/mL of tumor volume. In some embodiments, compositions of the present disclosure can include pharmaceutically acceptable excipients which are well known in the art. Pharmaceutically acceptable salts are also well known in the art. In some embodiments, the cumulative administration of multiple doses, for example during multiple arrest IA-TCH, may result in the administration of a "therapeutically effective amount" of a composition or peptide conjugate or pharmaceutically acceptable salt thereof of the present disclosure. The anesthetic can be any anesthetic known in the art that is appropriate for the subject to be treated. Exemplary anesthetics include but are not limited to isoflurane and propofol. In some embodiments, the anesthetic is administered at a dose sufficient to produce EEG silence in a subject. In some embodiments, the locus in the body of the subject is the brain. In some embodiments the cancer is a brain cancer. Other cancers that can be treated include those with a net negative charge on the surface of cell membranes including, but not limited to, solid cancers and blood cancers such as, by way of example but not limitation, leukemia. In some embodiments, the cancer is a glioma. In some embodiments, the method can further include a step of, prior to administering the pharmaceutical composition, lowering the body temperature of said subject. Such temperature lowering may be specific to a locus in the subject's body or general through the subject's body. The steps of reducing blood flow and intra-arterial injection can be repeated sequentially to result in multiple arrests and intra-arterial injection of lower doses of the peptide conjugate or pharmaceutically acceptable salt thereof. Methods for reducing blood flow in a subject can include, but are not limited to, inflation of a balloon occluding microcatheter in a blood vessel of a subject, administering adenosine to said subject, administering esmolol or a beta blocker to a subject, and administering a short acting drug that severely decreases blood pressure such as sodium nitroprusside. Adenosine can be administered to a subject at a dose between 10 and 90 mg including any value between. Doses of adenosine, esmolol, a beta blocker and any short acting drug that severely decreases blood pressure can readily be determined by one of ordinary skill in the art.

In some embodiments, a TAT oligomer conjugate can be administered to a subject via intravenous injection.

EXAMPLES

In the following Examples, Fluorescein-labeled TAT monomers and dimers were synthesized by standard solid state synthesis methods and have the following sequences and properties. All conjugates of TAT monomer and TAT dimers are N-terminal direct peptide linkages between the conjugate, e.g. melphalan, FITC or Cy5 and the TAT monomer or dimer.

TABLE 3

Sequence and Physiochemical Properties of TAT Monomers

| | |
|---|---|
| Single Letter Code Sequence: | 5-FAM-GRKKRRQRRR PPQQ-COOH (SEQ ID NO: 11) |
| Three Letter Code Sequence | 5-FAM-Gly-Arg-Lys-Lys-Arg-Arg-Gln-Arg-Arg-Arg-Pro-Pro-Gln-Gln-COOH (SEQ ID NO: 11) |
| Number of Residues: | 14 |
| Molecular Weight: | 2205.44 g/mol |
| Extinction coefficient: | 0 $M^{-1}cm^{-1}$ |

TABLE 3-continued

Sequence and Physiochemical Properties of TAT Monomers

| | |
|---|---|
| Iso-electric point: | pH 12.81 |
| Net charge at pH 7: | 7 |
| Estimated solubility: | Good water solubility |

TABLE 4

Sequence and Physiochemical Properties of TAT Dimers

| | |
|---|---|
| Single Letter Code Sequence: | 5-FAM-GRKKRRQRRR PPQQGRKKRR QRRRPPQQ-COOH (SEQ ID NO: 12) |
| Three Letter Code Sequence | 5-FAM-Gly-Arg-Lys-Lys-Arg-Arg-Gln-Arg-Arg-Arg-Pro-Pro-Gln-Gln-Gly-Arg-Lys-Lys-Arg-Arg-Gln-Arg-Arg-Arg-Pro-Pro-Gln-Gln-COOH (SEQ ID NO: 12) |
| Number of Residues: | 28 |
| Molecular Weight: | 4034.58 g/mol |
| Extinction coefficient: | 0 $M^{-1}cm^{-1}$ |
| Iso-electric point: | pH 13.15 |
| Net charge at pH 7: | 15 |
| Estimated solubility: | Good water solubility |

Cell lines used in the Examples include: luciferase expressing 9L, murine breast cancer 4T1, murine lung cancer LLC and ovarian cancer SKOV-3. The 9L cell line is an intrinsic glioma model while the 4T1 and LLC cell lines represent tumors that frequently metastasize to the brain. The SKOV-3 cell line is resistant to conventional chemotherapy due, in part, to an overexpression of p-GAP transporters.

9L, 4T1 and LLC cell lines were cultured in DMEM medium with 10% fetal bovine serum (FBS). SKOV-3 cells were cultured in McCoy's 5A medium with 10% FBS. C6 cells were cultured in F-12K medium with 15% horse serum and 2.5% FBS. MPPG3 cells were cultured in DMEM medium with 0.5% FBS, 1% N2, 10 ng/mL PDGF-AA, and 10 ng/mL FGF. Y79 cells were cultured in RPMI-1640 medium and 10% FBS. All cell lines were supplemented with penicillin (100 units/mL), and streptomycin (100 µg/mL) and incubated at 37° C. in air containing 5% $CO_2$.

Example 1: Cell Culture Experiments

Cell line uptake of fluorescein-labeled TAT monomer. 9L, 4T1, LLC and SKOV-3 cells were harvested and plated on 8-chamber glass slides at a density of $1 \times 10^4$ cells/chamber and incubated at 37° C. for 24 hours in culture medium. Prior to fluorescein-labeled TAT monomer exposure, cells were washed once with PBS. Exposure was performed by adding 50 µL of 0.5 mg/mL of fluorescein-labeled TAT monomer to each chamber and incubating for 5, 10 or 15 minutes including negative controls with PBS. Samples were also prepared and with or without heparin at 2.5 or 7.5 units/mL and fluorescein-labeled TAT dimer at 0.125 mg/mL. The exposure to fluorescein-labeled TAT monomer was stopped by removing the supernatant and washing three times with PBS and fixing with 4% PFA. Post-fixation nuclear staining was done using DAPI and imaging was performed using a Nikon A1 confocal microscope with DAPI and Alexa 488 channels.

Flow Cytometry Time Course of fluorescein-labeled TAT monomer uptake. Quantification of fluorescein-labeled TAT monomer uptake in 9L, C6, MPPG3, LLC, 4T1, MDA, Y79, SKOV-3 and I-HUVEC cell lines was performed by flow cytometry. Cells were grown to confluence in T75 cell culture flasks. Cells were harvested with Trypsin EDTA (0.25%) and washed once in PBS by centrifuging at 200 g for 5 minutes followed by removal of the supernatant. Cell pellets were resuspended in 100 µL of 0.5 mg/mL fluorescein-labeled TAT monomer and 1 µL of PI (100 µg/mL) for 5, 10, and 15 minutes. The exposure to fluorescein-labeled TAT monomer was stopped by adding 15 mL of PBS, centrifuging at 200 g for 5 minutes and removing the supernatant. Thereafter, the cells were fixed with 4% PFA for 10 minutes and washed once more with 15 mL of PBS. After centrifuging at 200 g for 5 minutes and removing the supernatant, the cells were then resuspended in 500 µL of FACS buffer and analyzed with a BD FACSCanto II flow cytometer. The mean fluorescence intensity and standard deviations of each sample were measured using the FITC channel in triplicates excluding dead cells (high PE channel fluorescence).

As shown in FIGS. 1A-1D, 9L, 4T1, LLC and SKOV-3 were able to take up the fluorescein-labeled TAT. The left panel of each image shows DAPI staining of fluorescein-labeled TAT monomer-treated cells (top) and negative control cells (bottom). The middle panel of each image shows FITC imaging of the same cells. The right panel shows an overlay of the DAPI staining and FITC imaging.

Figure 2:
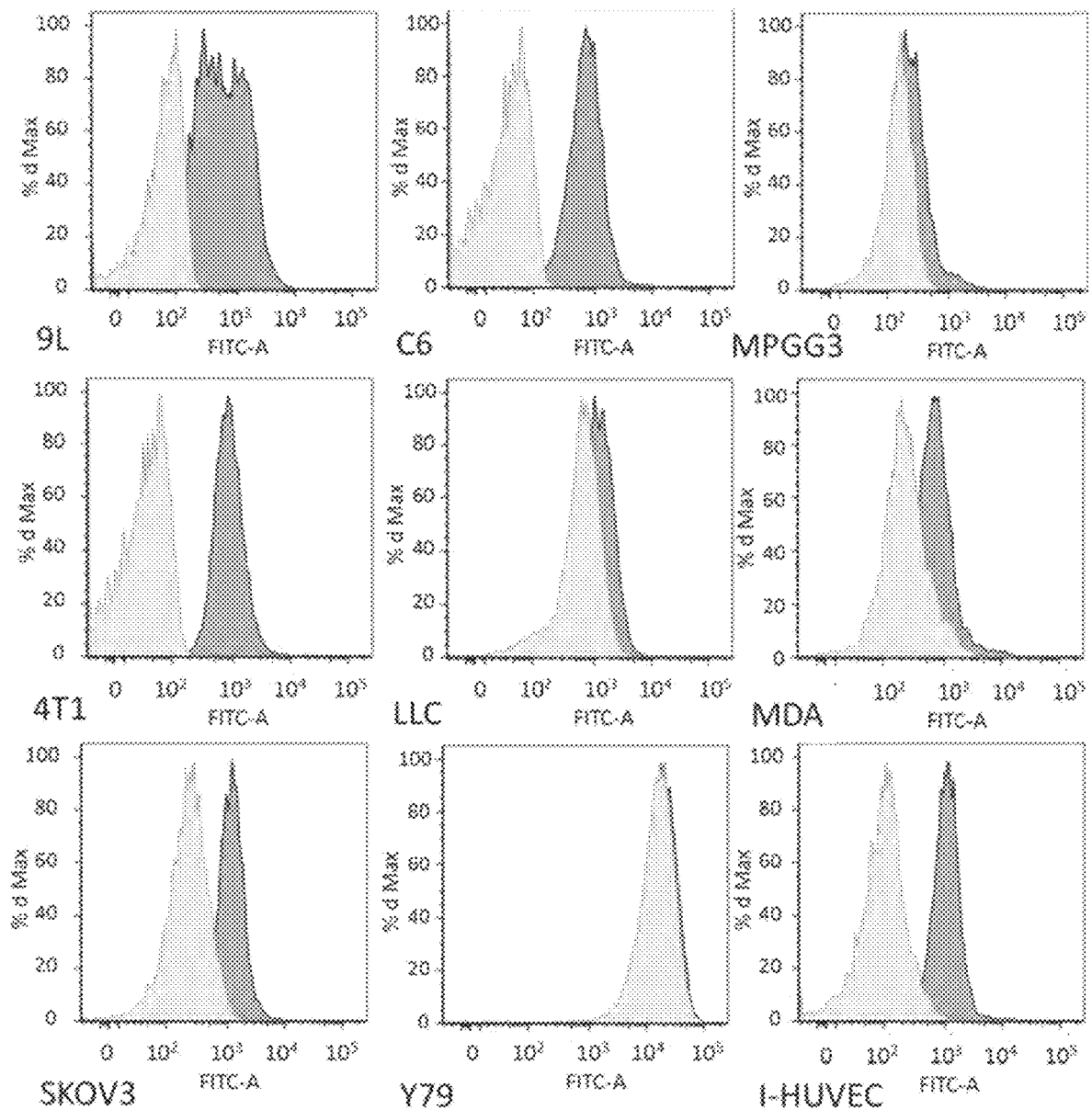
FIG. 2 depicts fluorescence distributions for 9L, C6, MPGG3, 4T1, LLC, MDA, SKOV-3, Y79 and I-HUVEC cells exposed to FITC-labeled TAT monomer (dark gray peaks) and unexposed to FITC-labeled TAT monomer (light gray peaks).
Figure 3:
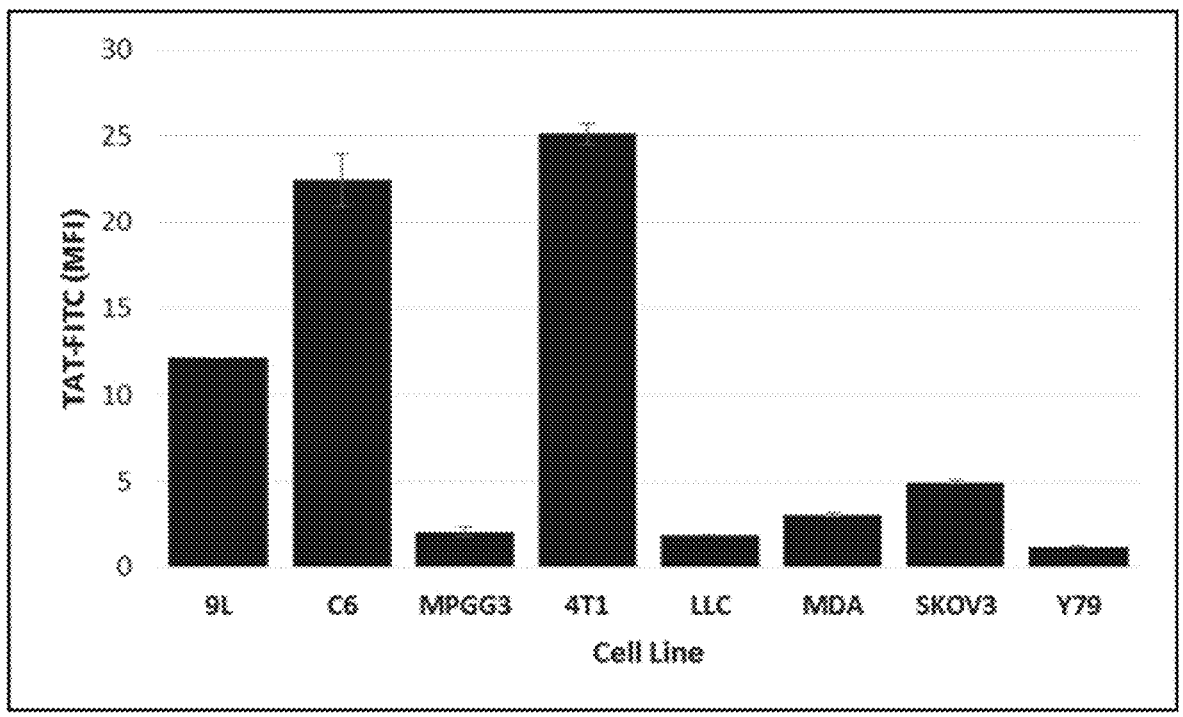
FIG. 3 depicts a quantitative measurement of mean fluorescence intensity (MFI) of 9L, C6, MPGG3, 4T1, LLC, MDA, SKOV-3 and Y79 cell lines exposed to FITC-labeled TAT monomer.

As shown in FIG. 2, which depicts fluorescence distributions for the various cell lines, fluorescein-labeled TAT monomer was taken up by each cell line as indicated by the dark gray peaks which indicate fluorescein-labeled TAT monomer fluorescence versus the light gray peaks which are for untreated cell lines. FIG. 3 shows the quantitative measurement of fluorescence intensity for each cell line.

Figure 4A:
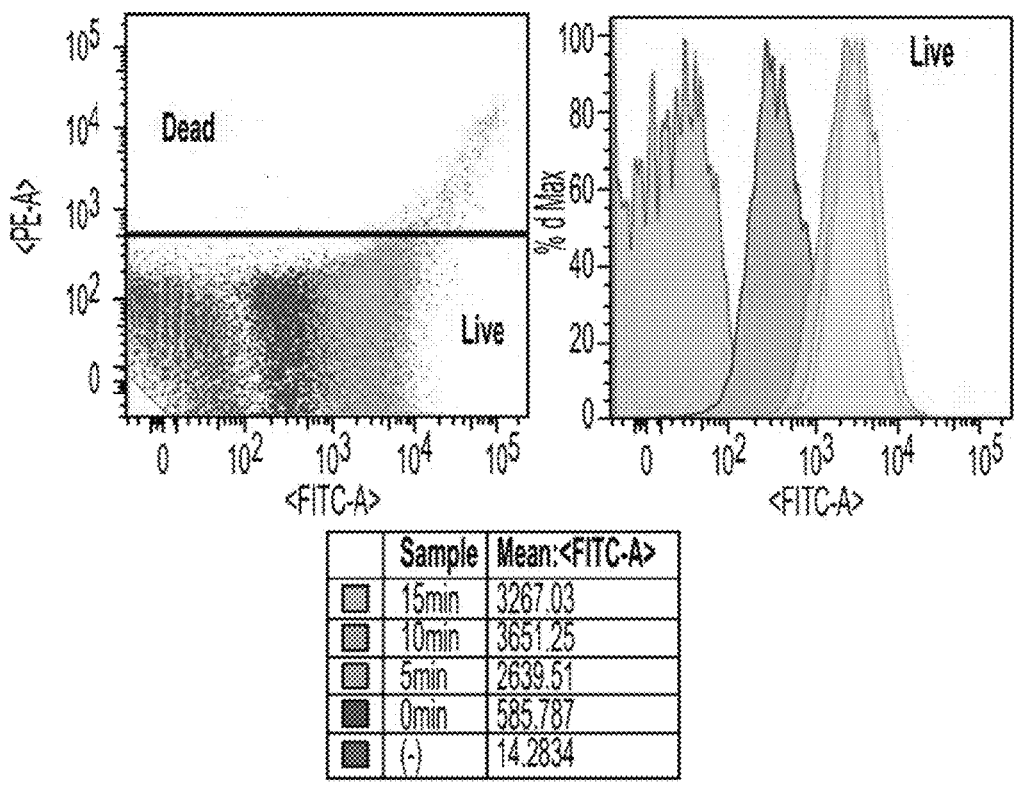
FIG. 4A depicts the uptake and retention over time of FITC-labeled TAT monomer by the 9L cell line over time as measured by flow cytometry, including fluorescence distribution.
Figure 4B:
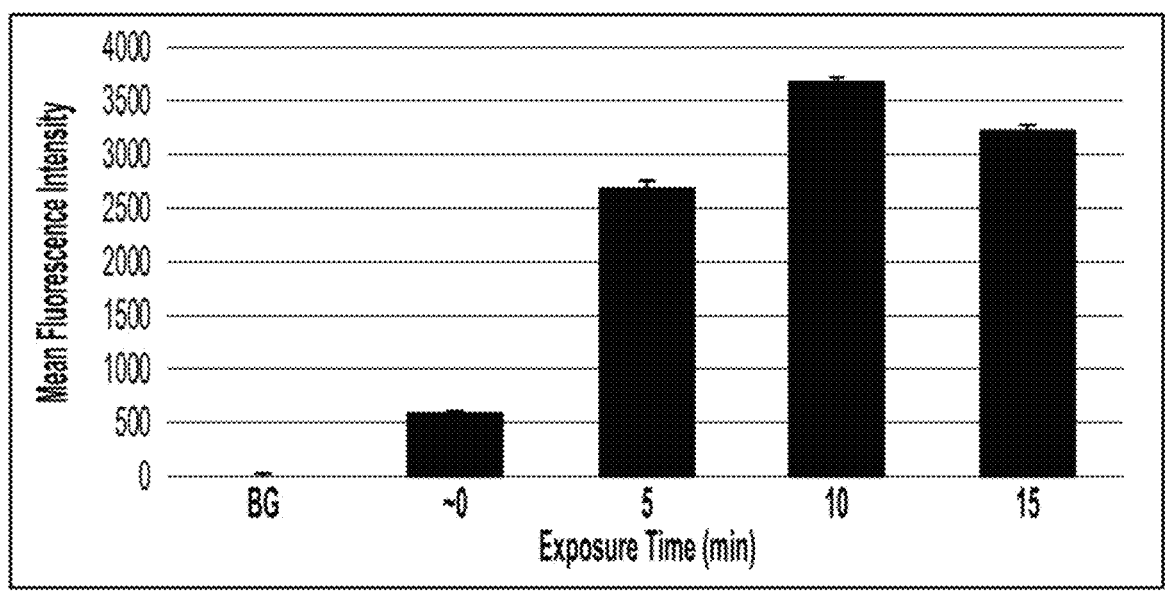
FIG. 4B shows the mean fluorescence intensity by flow cytometry over time for 9L cells exposed to FITC-labeled TAT monomer.
Figure 4C:
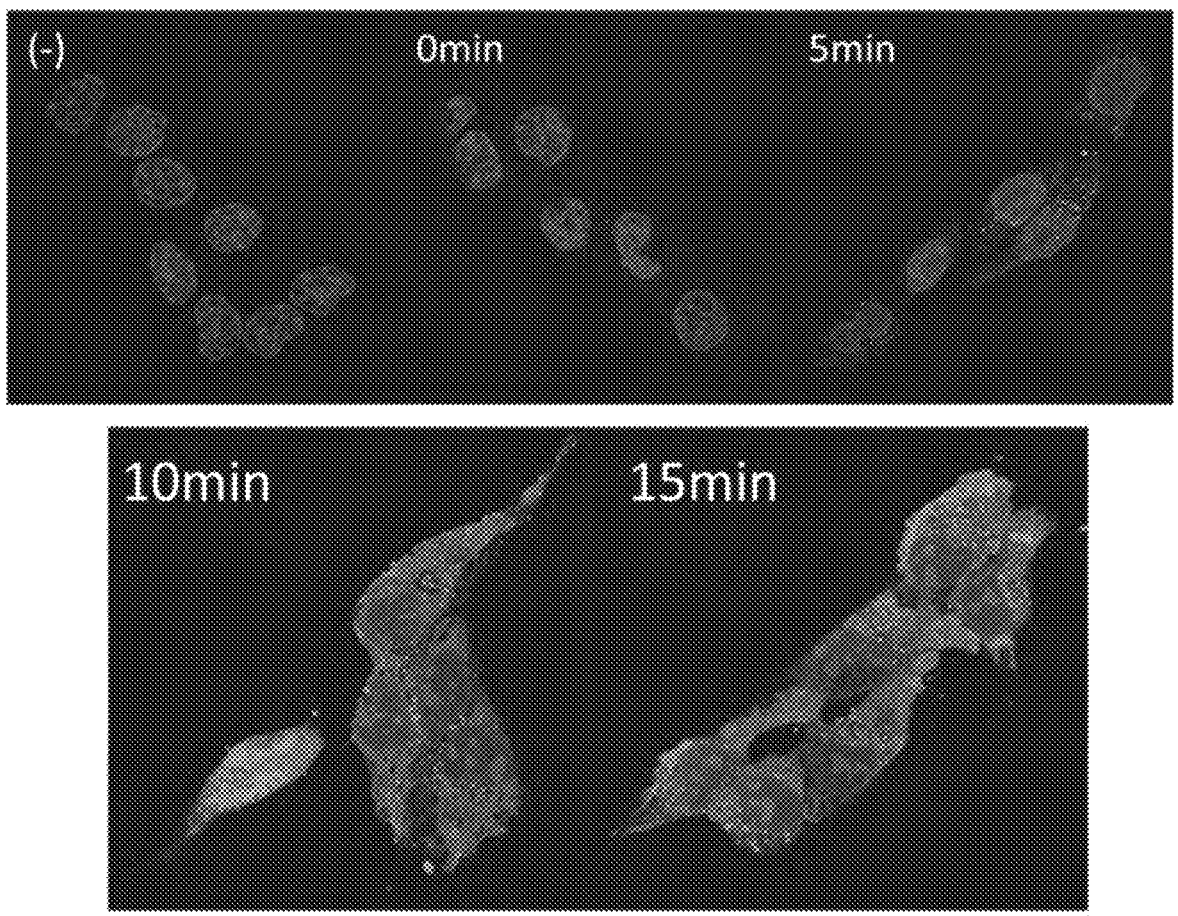
FIG. 4C depicts confocal microscopy images of 9L cells over time after exposure to FITC-labeled TAT monomer.

As shown in FIGS. 4A-4C, uptake and retention of the fluorescein-labeled TAT monomer was monitored by flow cytometry (FIG. 4A), spectrophotometry (FIG. 4B) and confocal microscopy (FIG. 4C), showing an increase in uptake with time of exposure and retention of the fluorescein-labeled TAT monomer.

Cell line uptake of fluorescein-labeled TAT dimer. 9L cells were harvested and plated on 8-chamber glass slides at a density of $1 \times 10^4$ cells/chamber and incubated at 37° C. for 24 hours in culture medium. Prior to fluorescein-labeled TAT dimer exposure, cells were washed once with PBS. Exposure was performed by adding 50 µL of 0.005, 0.05 or 0.5 mg/mL of fluorescein-labeled TAT dimer to each chamber and incubating for 5, 10 or 15 minutes including negative controls with PBS. Samples were also prepared with or without heparin at 2.5 or 7.5 units/mL and fluorescein-labeled TAT dimer at 0.125 mg/mL. The exposure to fluorescein-labeled TAT dimer was stopped by removing the supernatant and washing three times with PBS and fixing with 4% PFA. Post-fixation nuclear staining was done using DAPI and imaging was performed using a Nikon A1 confocal microscope with DAPI and Alexa 488 channels. The same method was performed using a C6 gliosarcoma cell line, 4T1 breast cancer cell line, LLC lung cancer cell line, and MDA breast cancer cell line. A similar procedure was performed with the 9L, C6, MPPG3, LLC, 4T1, MDA, Y79 and SKOV-3 cell lines using fluorescein-labeled TAT monomer at a concentration of 0.5 mg/mL with a 10 minute incubation. Data and images from this method are shown in FIGS. 5A-5C, 7C-7D and 8C-8D.

Spectrophotometry Time Course of fluorescein-labeled TAT Dimer Uptake. Quantification of fluorescein-labeled TAT dimer uptake in 9L, C6, 4T1, LLC, and MDA cell lines was performed by spectrophotometry. Cells were harvested with Trypsin EDTA (0.25%) and seeded on black wall clear bottom 96 well plates at densities of $1 \times 10^4$ to $1 \times 10^5$ cells/well and incubated at 37° C. for 24 hours in culture medium. Prior to fluorescein-labeled TAT dimer exposure, cells were washed once with PBS. Exposure was performed in triplicate by adding 100 μL of 0.005, 0.05, or 0.5 mg/mL of fluorescein-labeled TAT dimer to each well and incubating for 5, 10 or 15 minutes including negative controls with PBS. Exposure was stopped by removing the supernatant and washing 3× with PBS. Fluorescence was measured by spectrophotometer immediately after washes with excitation/emission filters set at 495/520 nm, respectively. In addition to the uptake of TAT dimer experiment was performed at a concentration of 0.125 mg/mL for 15 minutes with and without heparin at varying concentration (2.5-7.5 units/mL). Data and images from this method are shown in FIGS. 6, 7A-7B, 8A-8B, 9A-9B and 10A-10B.

Figure 5A:
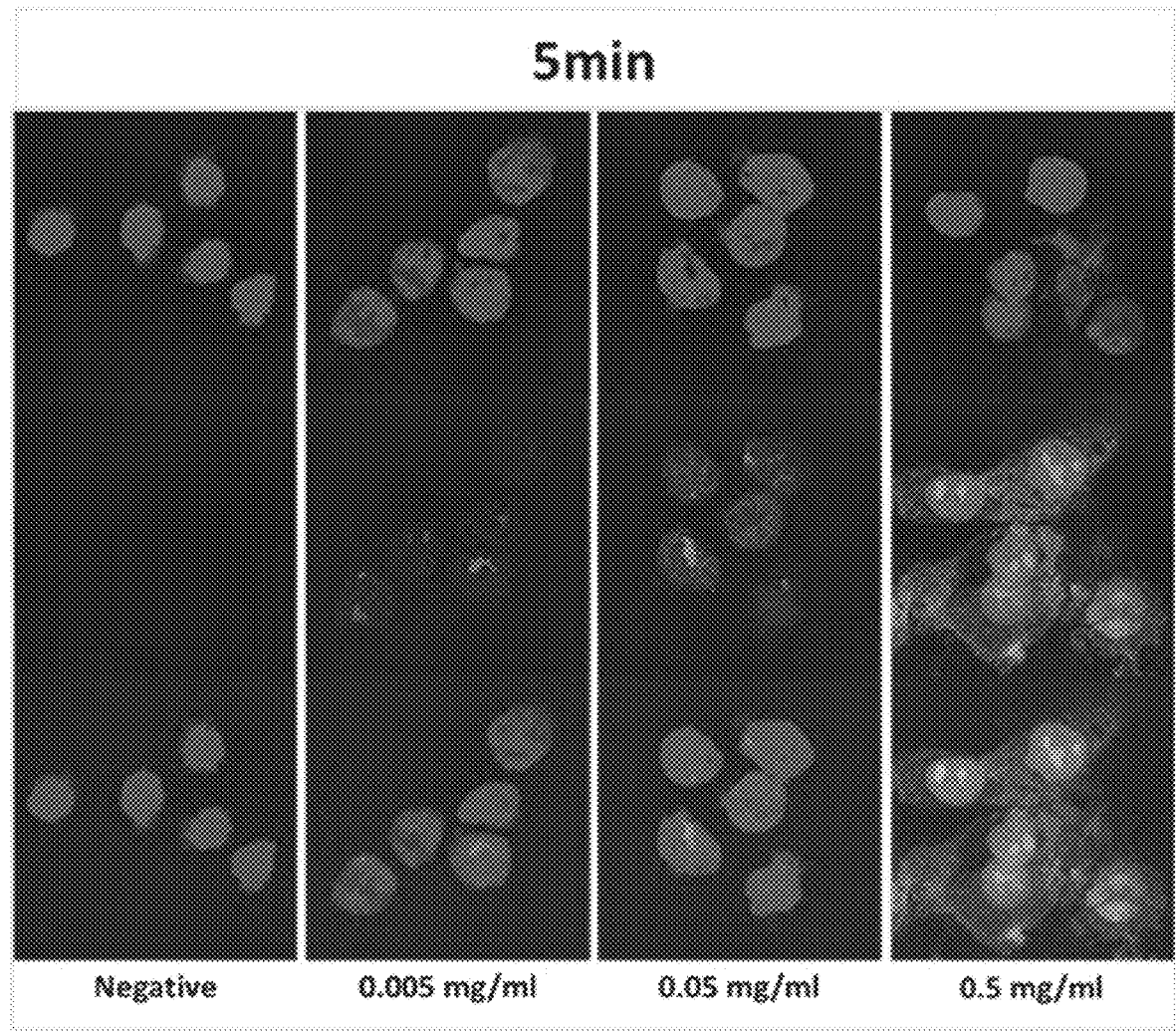
FIG. 5A depicts images obtained by confocal microscopy of 9L cells with or without varying levels of exposure to FITC-labeled TAT dimer after 5 minutes.
Figure 5B:
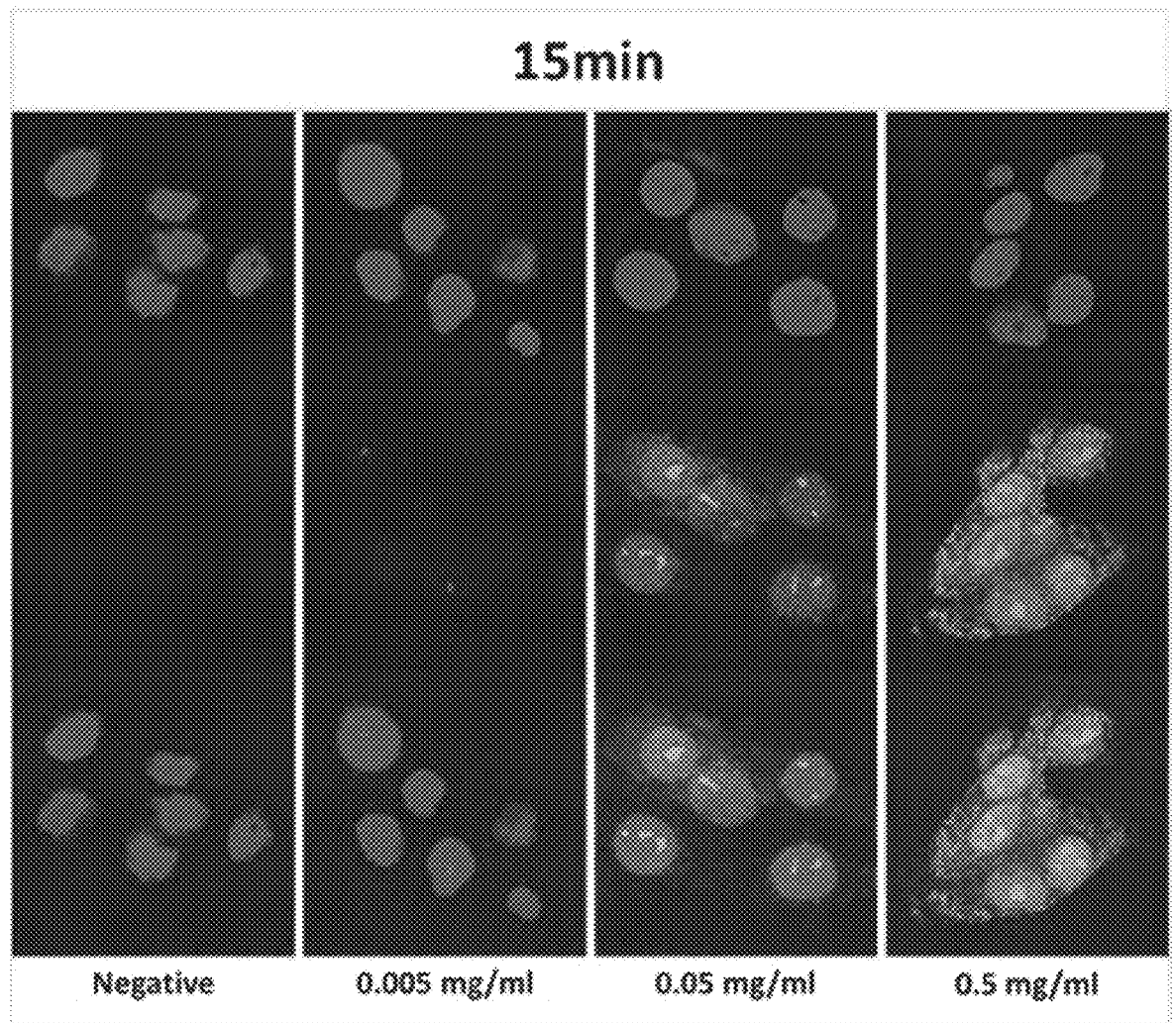
FIG. 5B depicts images obtained by confocal microscopy of 9L cells with or without varying levels of exposure to FITC-labeled TAT dimer after 15 minutes.

As shown in FIGS. 5A and 5B, which depict confocal microscopy images of the 9L cells at 5 minutes and 15 minutes post-exposure to the fluorescein-labeled TAT dimer, respectively, uptake of the fluorescein-labeled TAT dimer was concentration dependent. The top row of each figure shows fluorescence of the cell nuclei (blue), while the middle row of each figure shows fluorescence of the fluorescein-labeled TAT dimer (green) and the bottom row of each figure shows an overlaid image of the fluorescence images above it overlaid, showing the fluorescein-labeled TAT dimer complexed on the surface of the cells.

Figure 5C:
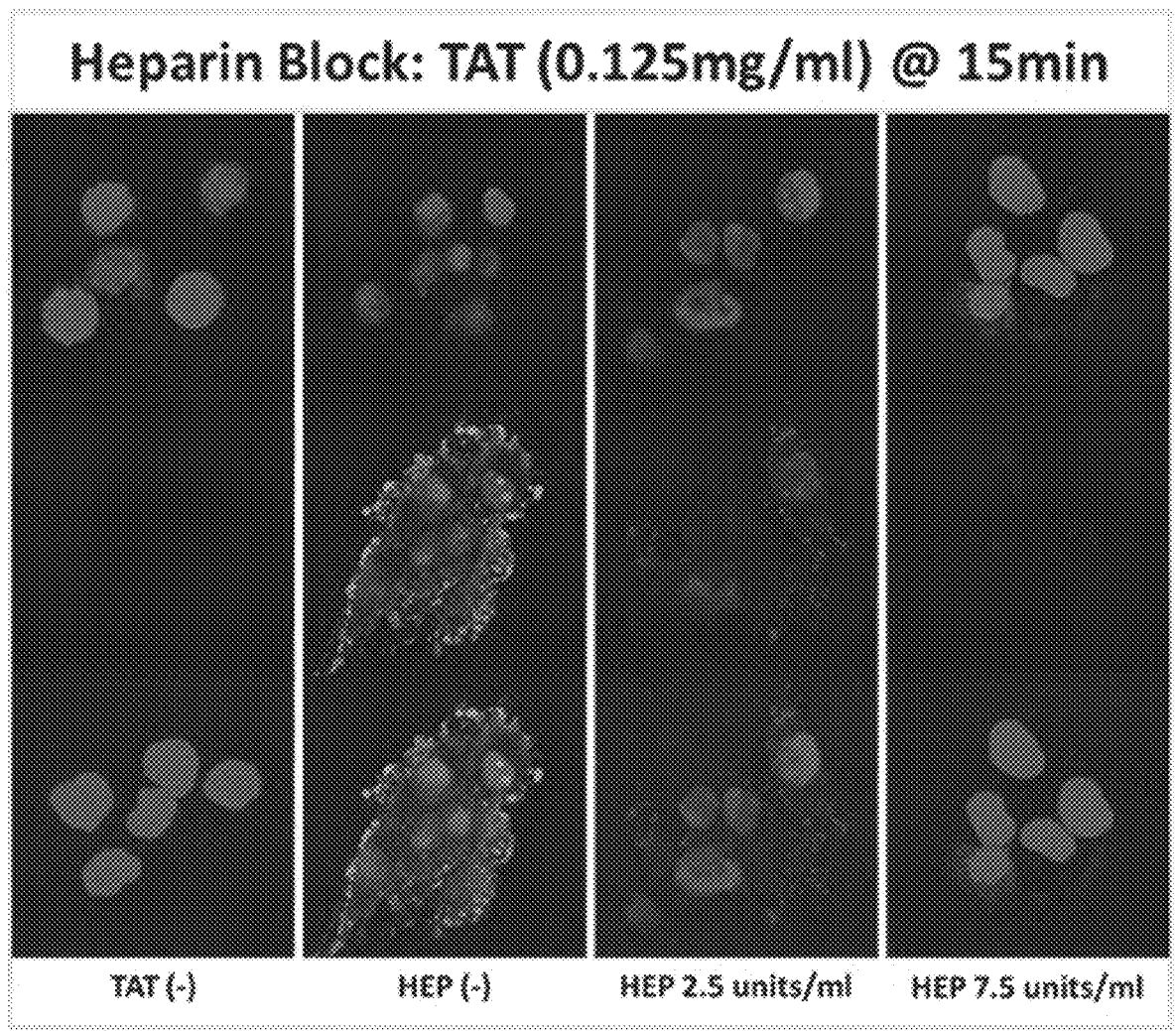
FIG. 5C depicts images obtained by confocal microscopy of 9L cells with or without varying levels heparin during exposure to FITC-labeled TAT dimer after 15 minutes.
Figure 6:
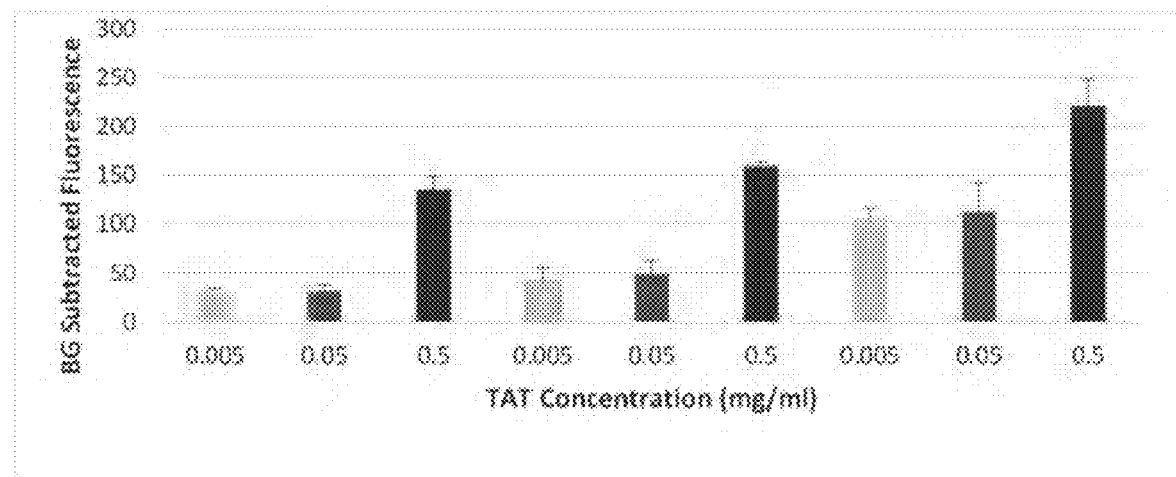
FIG. 6 depicts a chart of BG Subtracted Fluorescence of 9L cells after exposure to FITC-labeled TAT dimers by spectrophotometry.
Figure 7A:
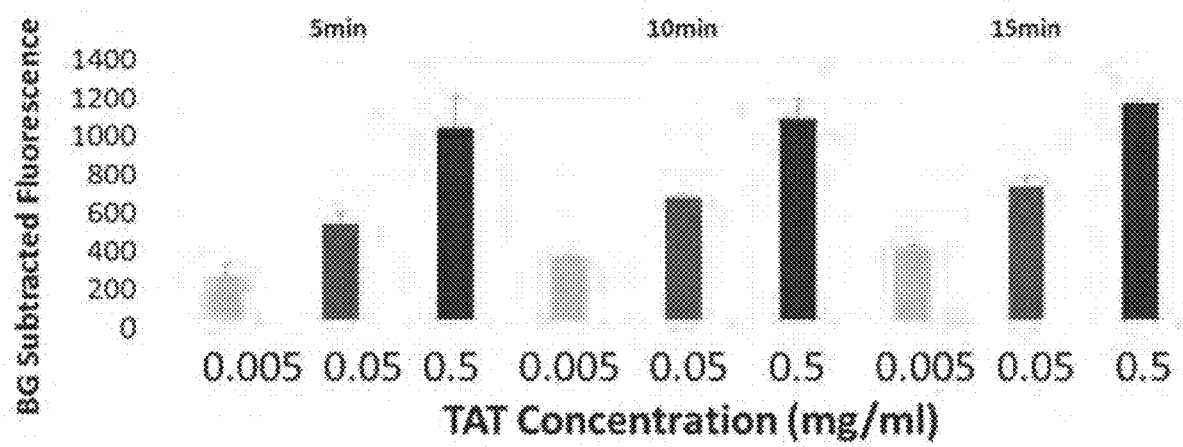
FIG. 7A depicts a chart of BG Subtracted Fluorescence of C6 cells after exposure to FITC-labeled TAT dimers at 5, 10 and 15 minutes post-exposure and at varying levels of FITC-labeled TAT dimers.
Figure 7B:
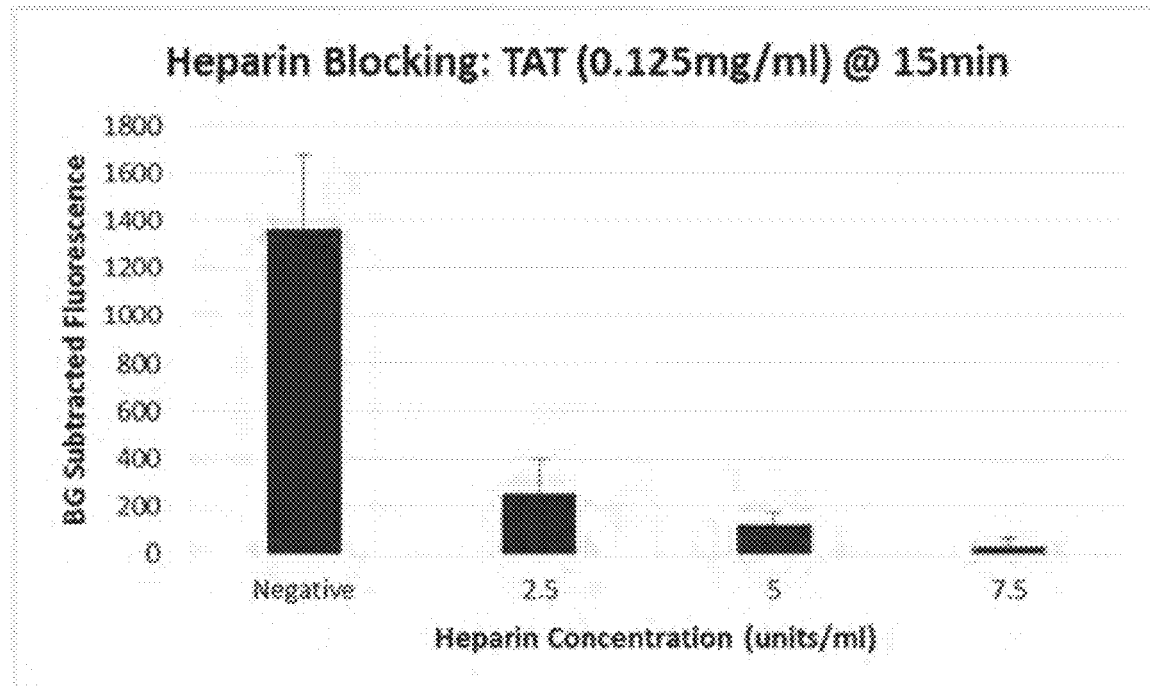
FIG. 7B depicts a chart of BG Subtracted Fluorescence of C6 cells after exposure to FITC-labeled TAT dimer at 0.125 mg/mL for 15 minutes with or without varying levels of heparin.
Figure 7C:
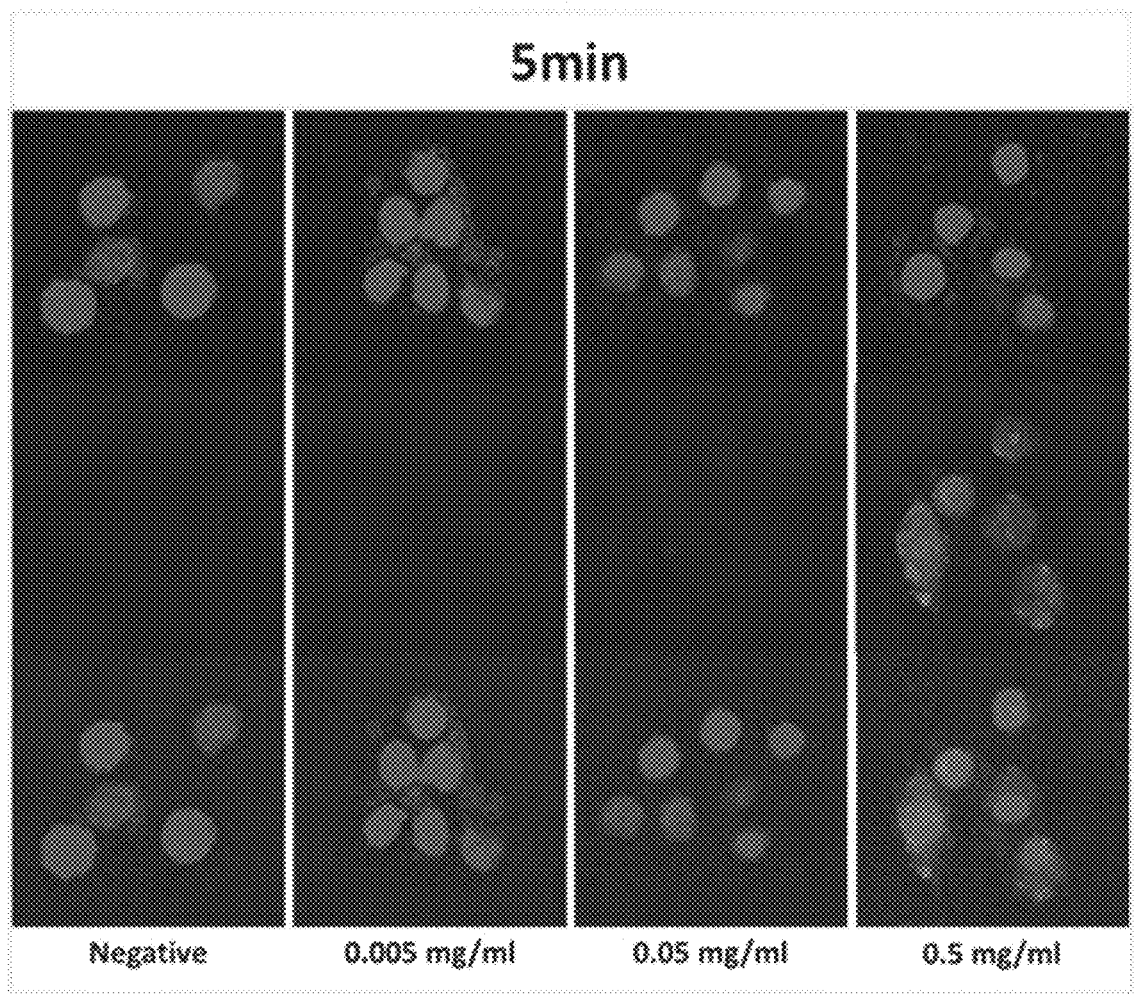
FIG. 7C depicts confocal microscopy images of C6 cells with or without exposure for 5 minutes to varying levels of FITC-labeled TAT dimers showing DAPI-staining (top), FITC fluorescence (middle) and a composite image (bottom).
Figure 7D:
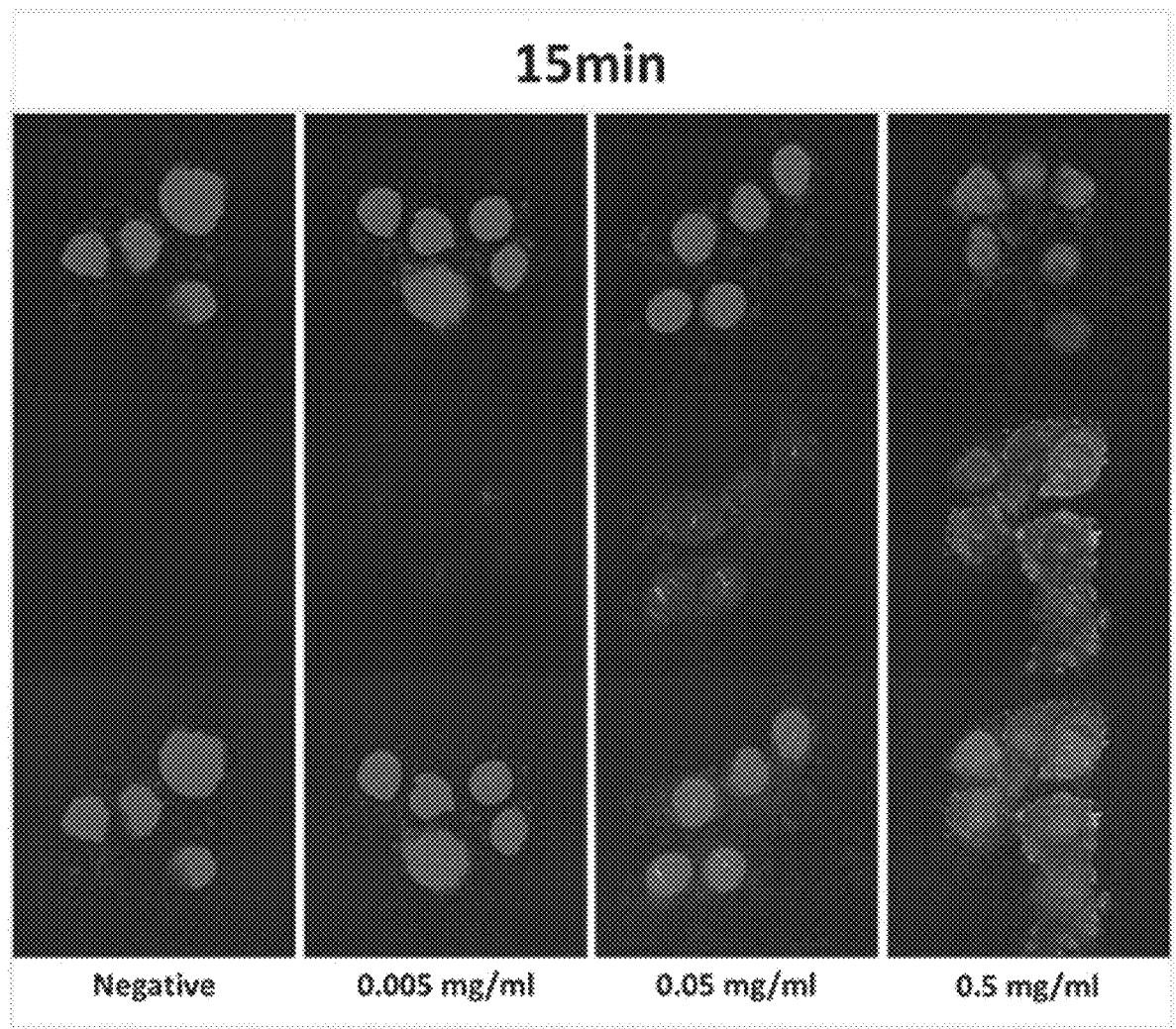
FIG. 7D depicts confocal microscopy images of C6 cells with or without exposure for 15 minutes to varying levels of FITC-labeled TAT dimers showing DAPI-staining (top), FITC fluorescence (middle) and a composite image (bottom).
Figure 8A:
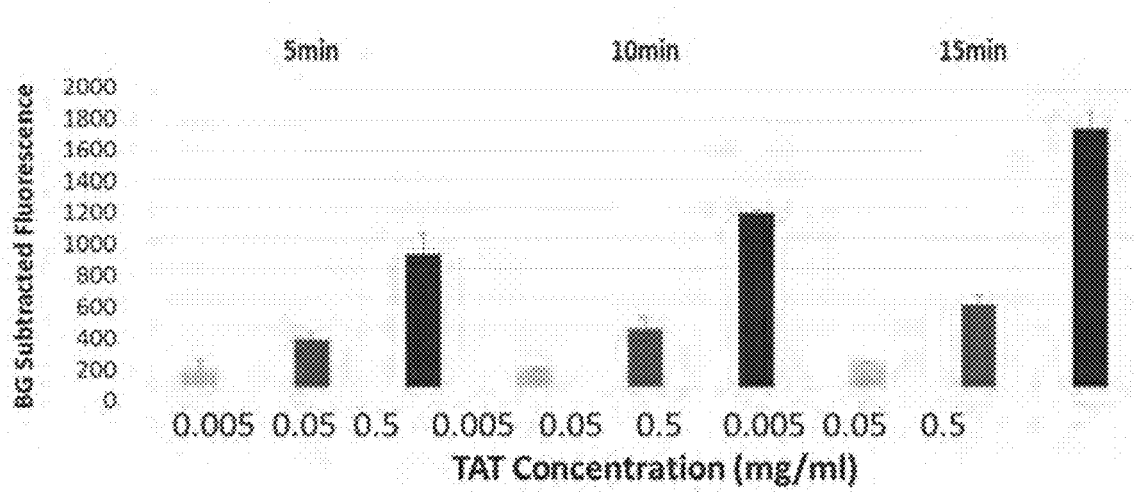
FIG. 8A depicts a chart of BG Subtracted Fluorescence of 4T1 cells after exposure to FITC-labeled TAT dimers at 5, 10 and 15 minutes post-exposure and at varying levels of FITC-labeled TAT dimers.
Figure 8B:
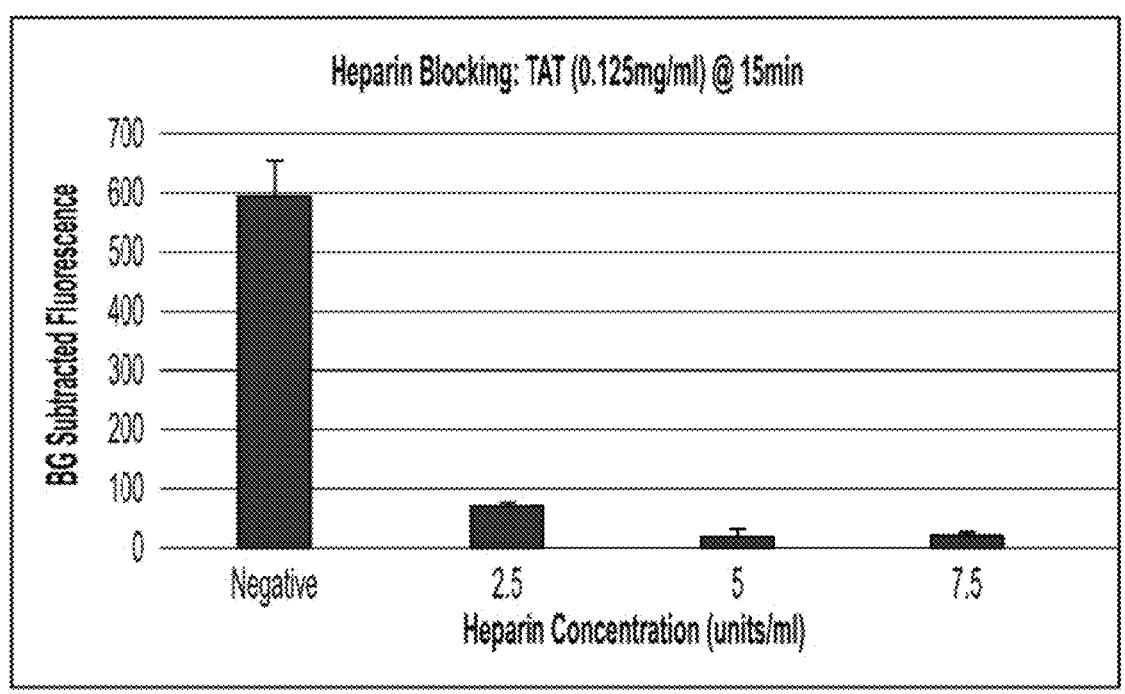
FIG. 8B depicts a chart of BG Subtracted Fluorescence of 4T1 cells after exposure to FITC-labeled TAT dimer at 0.125 mg/mL for 15 minutes with or without varying levels of heparin.
Figure 8C:
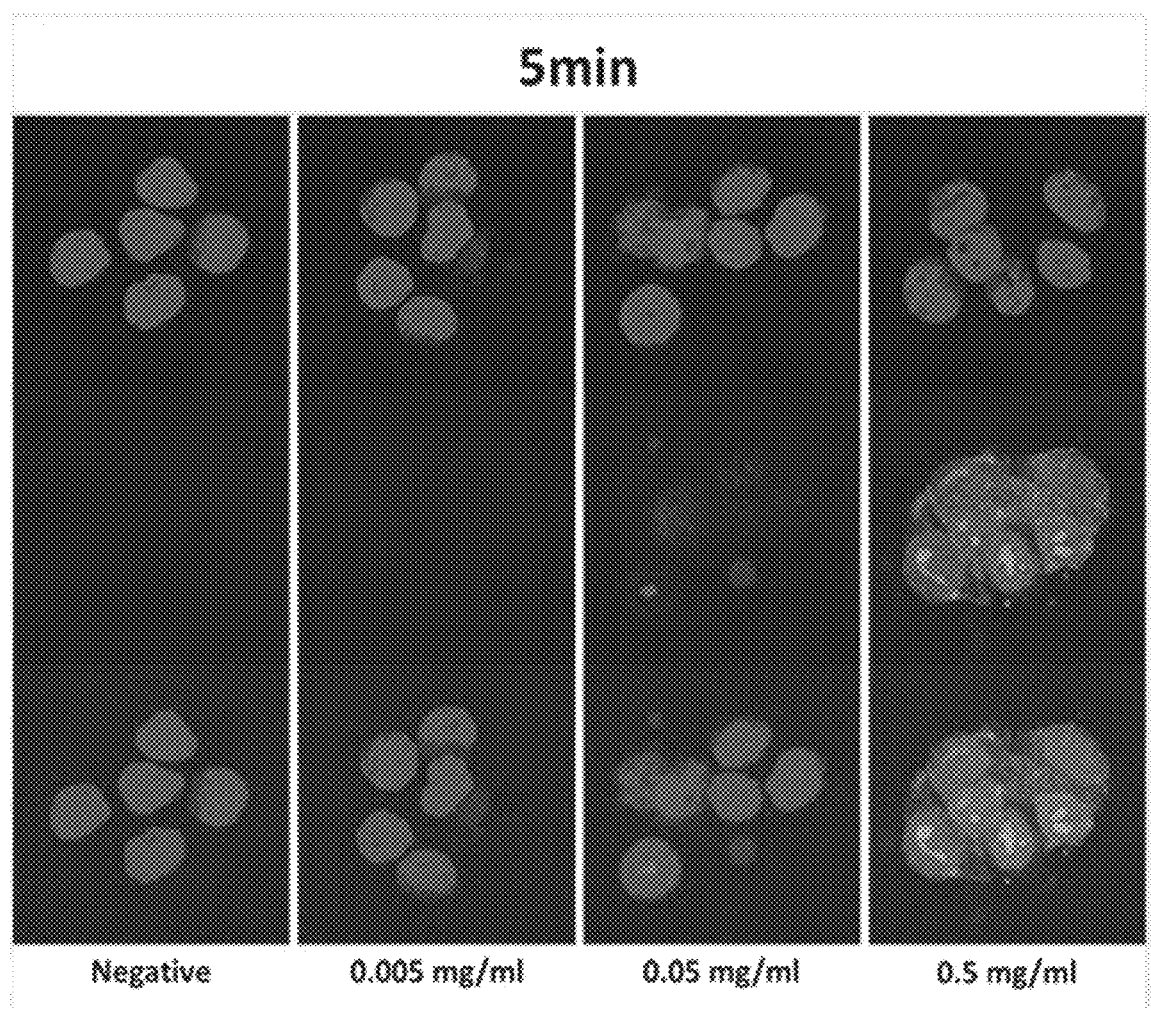
FIG. 8C depicts confocal microscopy images of 4T1 cells with or without exposure for 5 minutes to varying levels of FITC-labeled TAT dimers showing DAPI-staining (top), FITC fluorescence (middle) and a composite image (bottom).
Figure 8D:
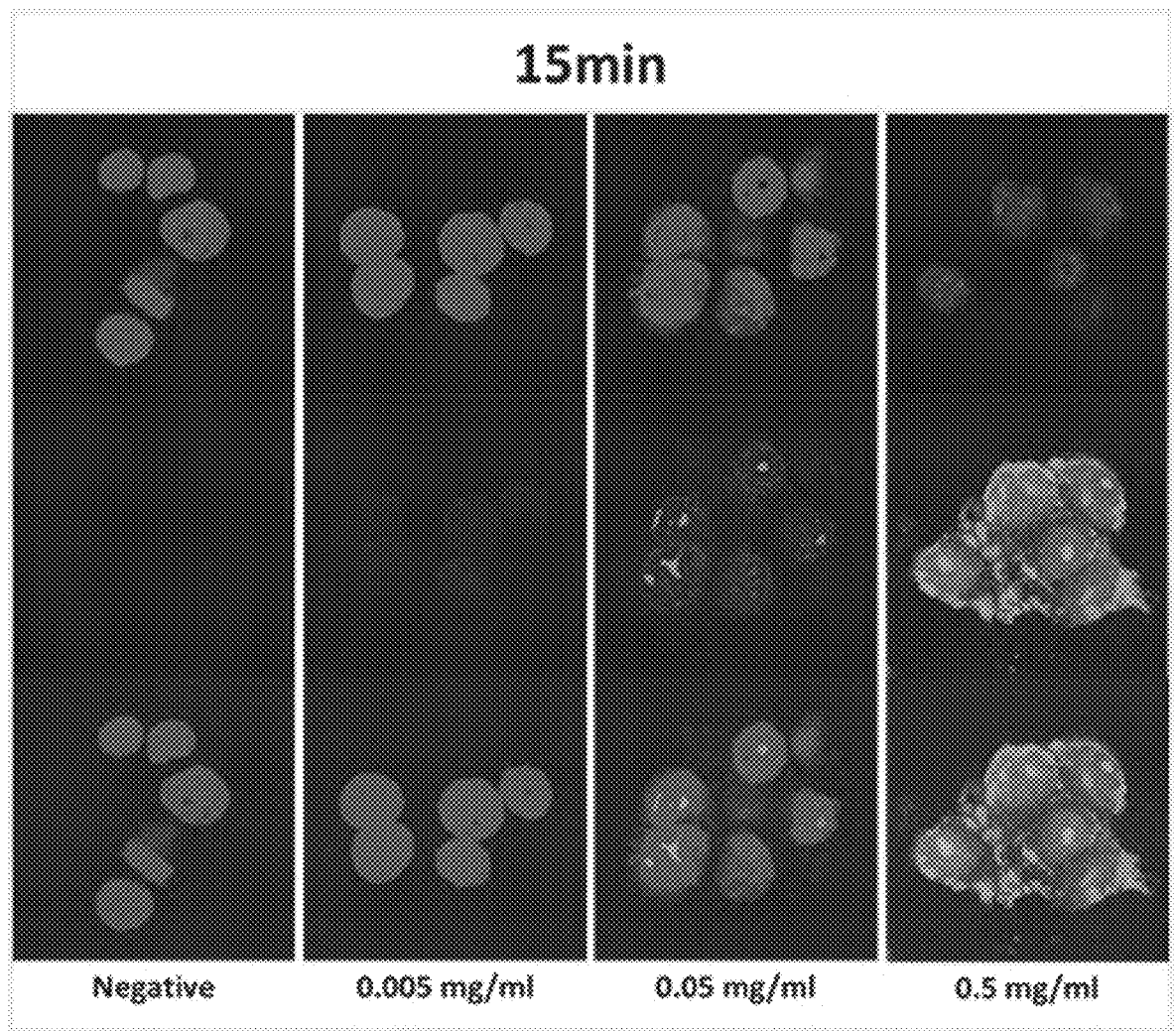
FIG. 8D depicts confocal microscopy images of 4T1 cells with or without exposure for 15 minutes to varying levels of FITC-labeled TAT dimers showing DAPI-staining (top), FITC fluorescence (middle) and a composite image (bottom).
Figure 9A:
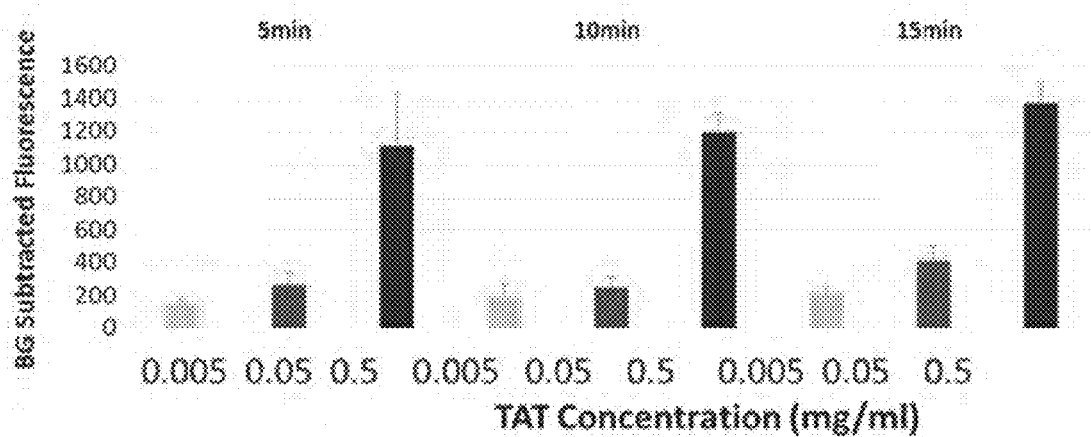
FIG. 9A depicts a chart of BG Subtracted Fluorescence of LLC cells after exposure to FITC-labeled TAT dimers at 5, 10 and 15 minutes post-exposure and at varying levels of FITC-labeled TAT dimers.
Figure 9B:
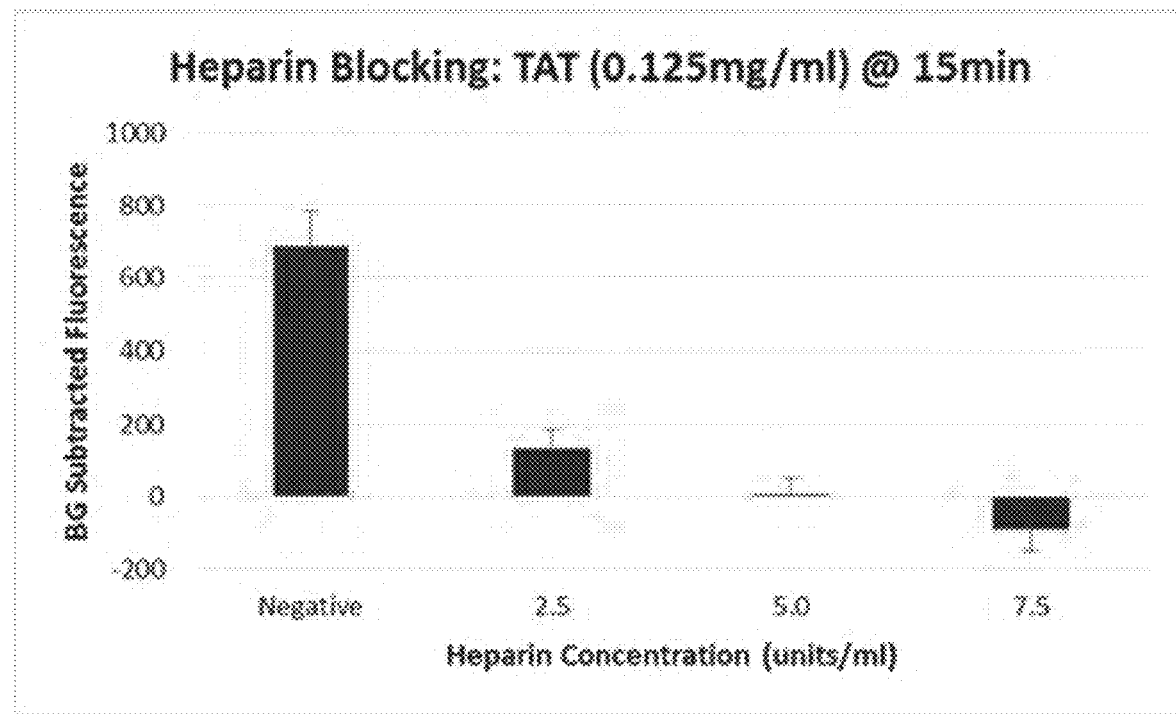
FIG. 9B depicts a chart of BG Subtracted Fluorescence of LLC cells after exposure to FITC-labeled TAT dimer at 0.125 mg/mL for 15 minutes with or without varying levels of heparin.
Figure 10A:
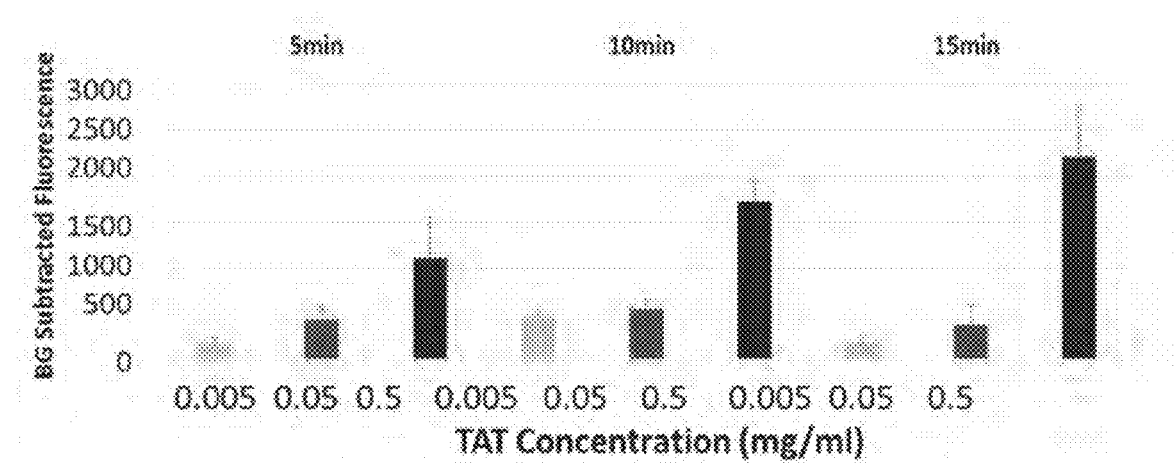
FIG. 10A depicts a chart of BG Subtracted Fluorescence of MDA cells after exposure to FITC-labeled TAT dimers at 5, 10 and 15 minutes post-exposure and at varying levels of FITC-labeled TAT dimers.
Figure 10B:
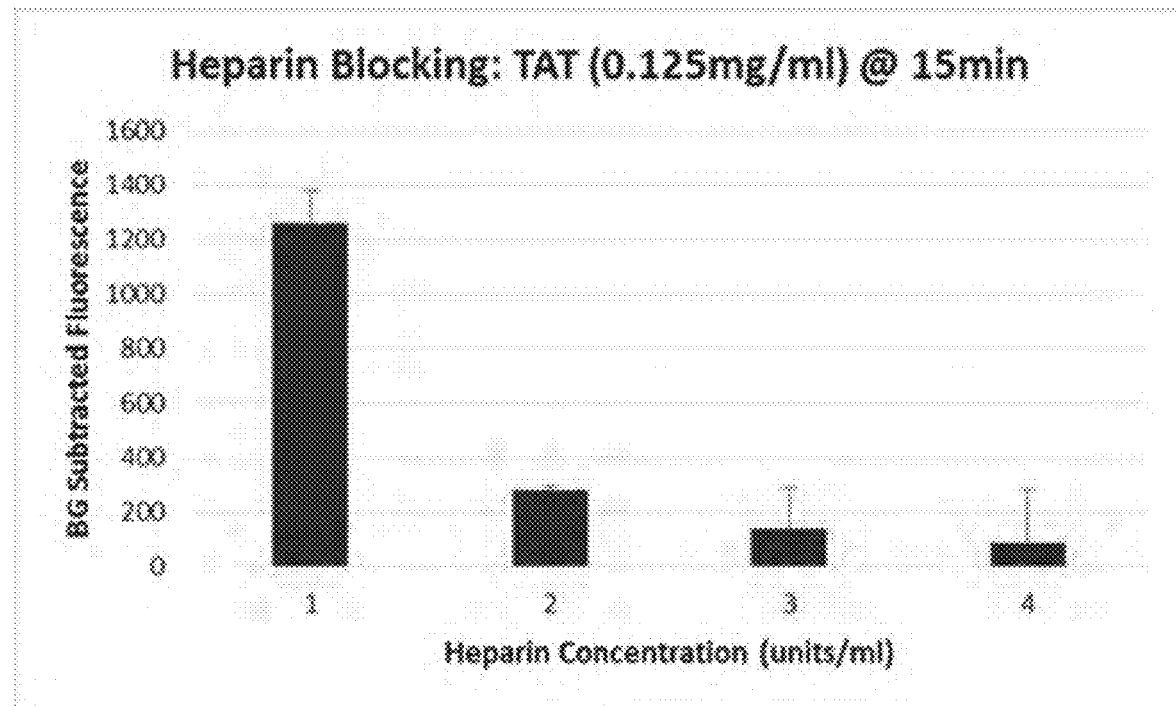
FIG. 10B depicts a chart of BG Subtracted Fluorescence of MDA cells after exposure to FITC-labeled TAT dimer at 0.125 mg/mL for 15 minutes with or without varying levels of heparin.

As shown in FIG. 5C, even after 15 minutes of exposure to the fluorescein-labeled TAT dimer, the presence of heparin blocked fluorescein-labeled TAT dimer complexation to the 9L cells, suggesting that the cationic surface charge of the molecule determines uptake that can be blocked by circulating anionic molecules as fluorescein-labeled TAT dimer complexation was observed in the absence of heparin.

Similar results were observed for the C-6, 4T1, LLC and MDA cell lines. As shown in FIGS. 7A, 8A, 9A and 10A, respectively, uptake of the fluorescein-labeled TAT dimer was concentration dependent. FIGS. 7B, 8B, 9B and 10B show a similar blocking effect of heparin on complexation of the fluorescein-labeled TAT dimer with the cell surface of each cell line.

Four cell lines-9L, 4T1, SKOV-3 and LLC—were used for preliminary cytological studies to show the phosphatidylserine (PS) expression on the surface of the cell membranes by Annexin V uptake by flow cytometry. Cell viability was assessed by propidium iodide (PI) staining.

Flow Cytometry of PS Expression. PS expression of all four cell lines were assessed using the Alexa Fluor® 488 Annexin V/Dead Cell Apoptosis Kit (Invitrogen, Carlsbad, CA) following the recommended flow cytometry protocol. Briefly, cells were harvested using Trypsin-EDTA (0.25%) and washed with phosphate-buffered saline (PBS) by centrifuging at 200 g for 5 minutes followed by removal of the supernatant. Cells were then resuspended in 100 μL of Annexin V binding buffer at about $1 \times 10^6$ cell/mL and stained by adding 5 μL of Alex Fluor® 488 Annexin V and 1 μL of PI (100 μg/mL) and incubated at room temperature for 15 minutes. After incubation, an additional 400 μL of binding buffer was added and fluorescence was measured using the FITC and PE channels on a BD FACS Canto II flow cytometer. Data analysis was performed using the Flow Jo analysis platform.

Figure 11A:
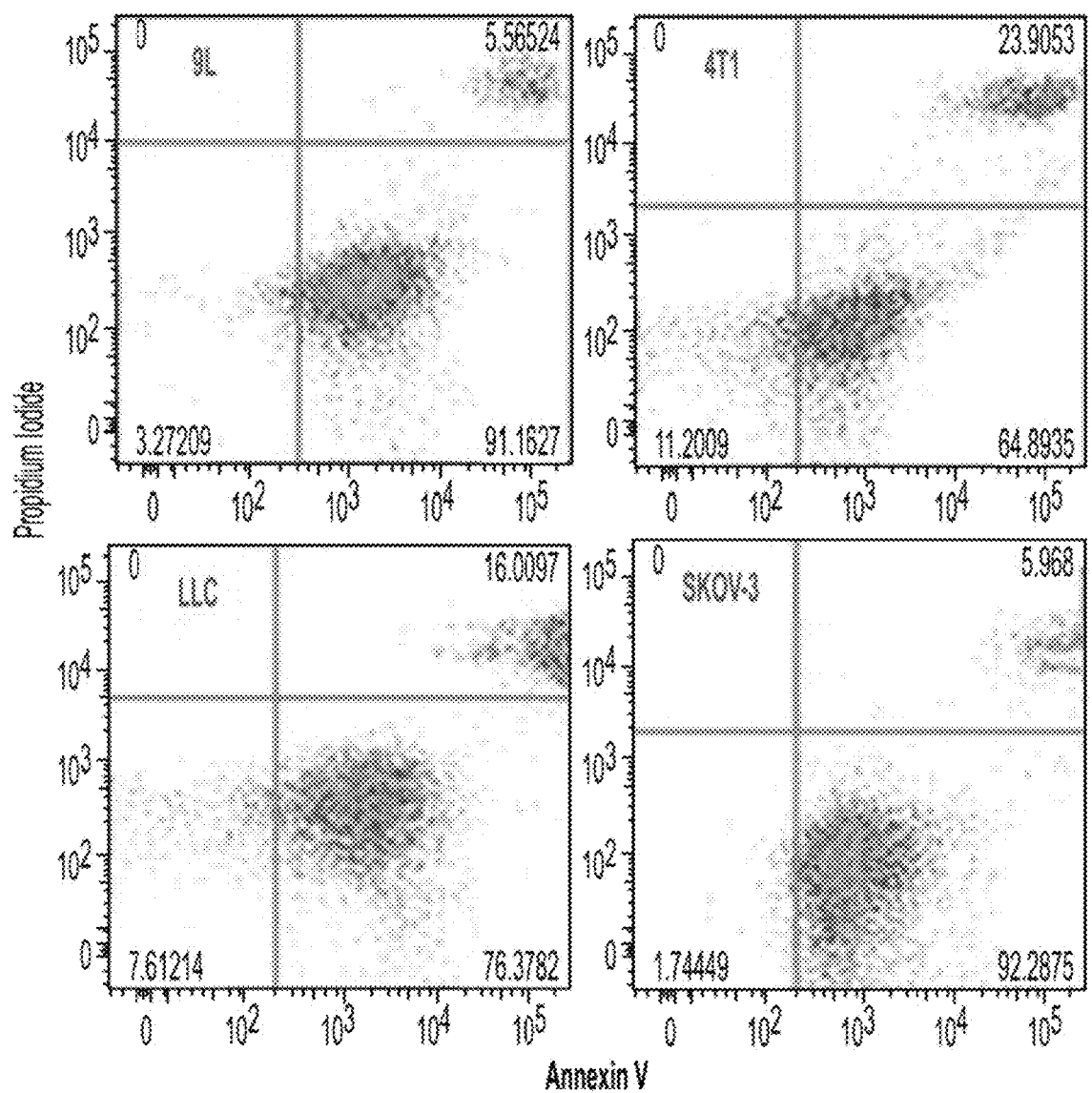
FIG. 11A shows scatterplots for 9L, 4T1, LLC and SKOV-3 cells lines based on propidium iodide staining and FITC-Annexin V fluorescence.
Figure 11B:
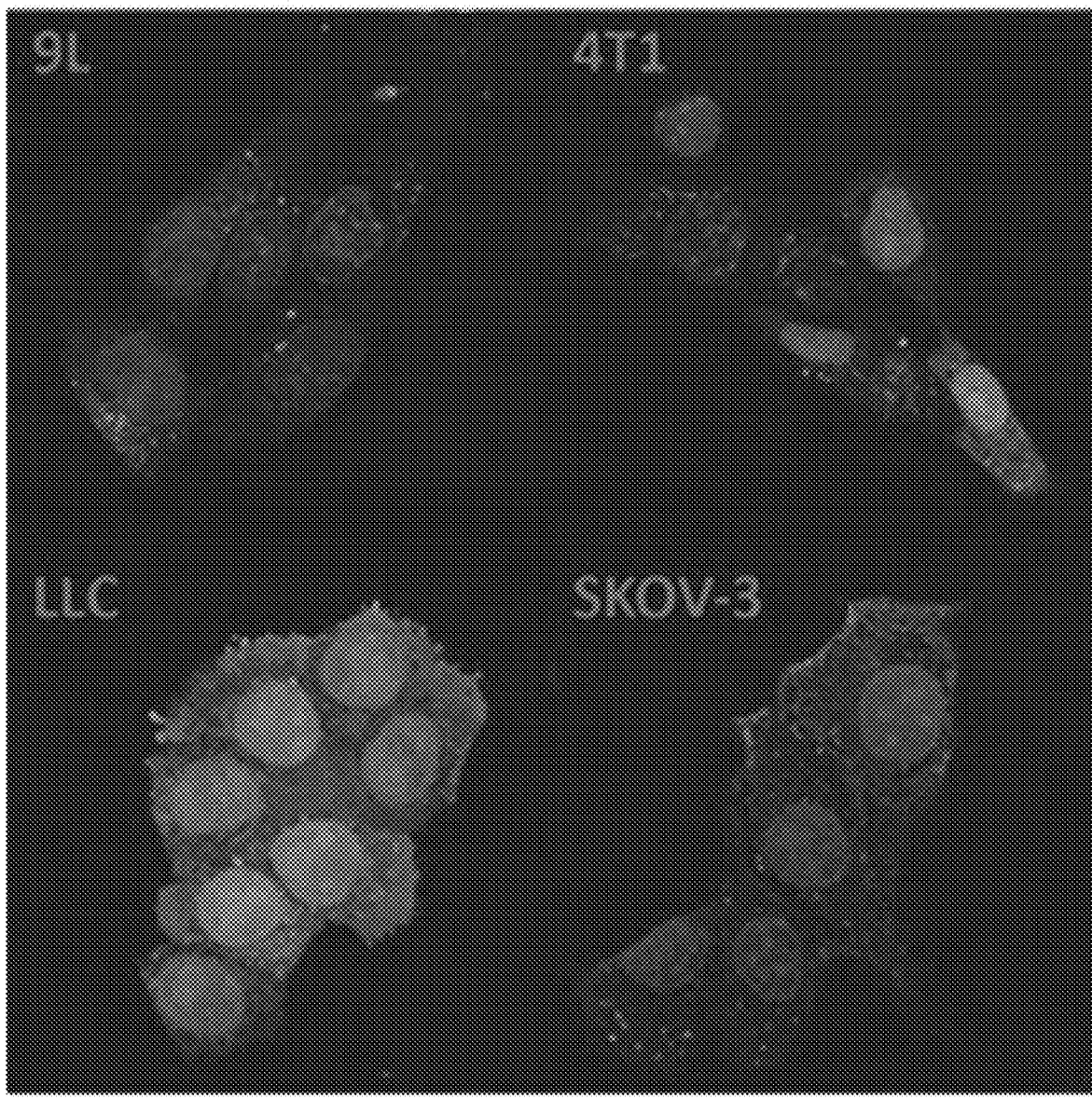
FIG. 11B shows confocal microscopy images of 9L, 4T1, LLC and SKOV-3 cells after exposure to FITC-labeled TAT monomer.
Figure 11C:
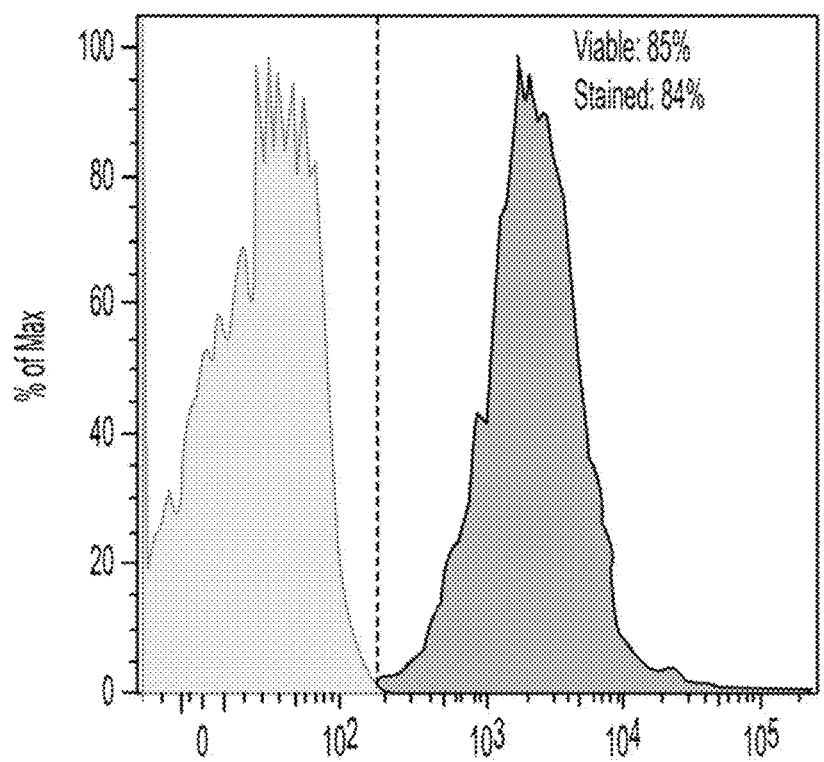
FIG. 11C depicts fluorescence distribution for FITC-Annexin V in treated cells (dark gray) and untreated cells (light gray).
Figure 11D:
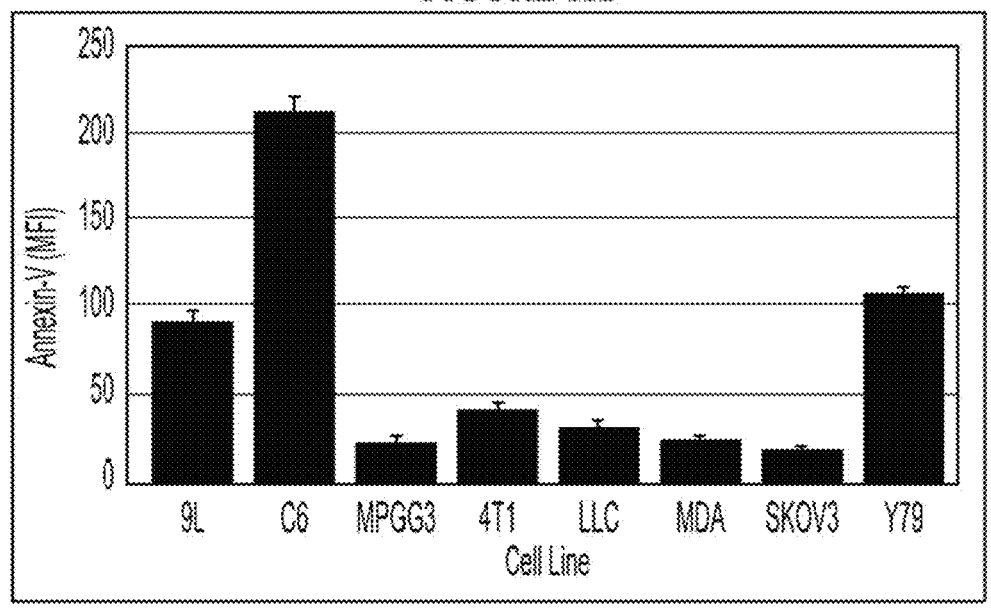
FIG. 11D depicts a chart of MFI by FITC-Annexin V fluorescence for 9L, C6, MPGG3, 4T1, LLC, MDA, SKOV-3 and Y79 cell lines.
Figure 11E:
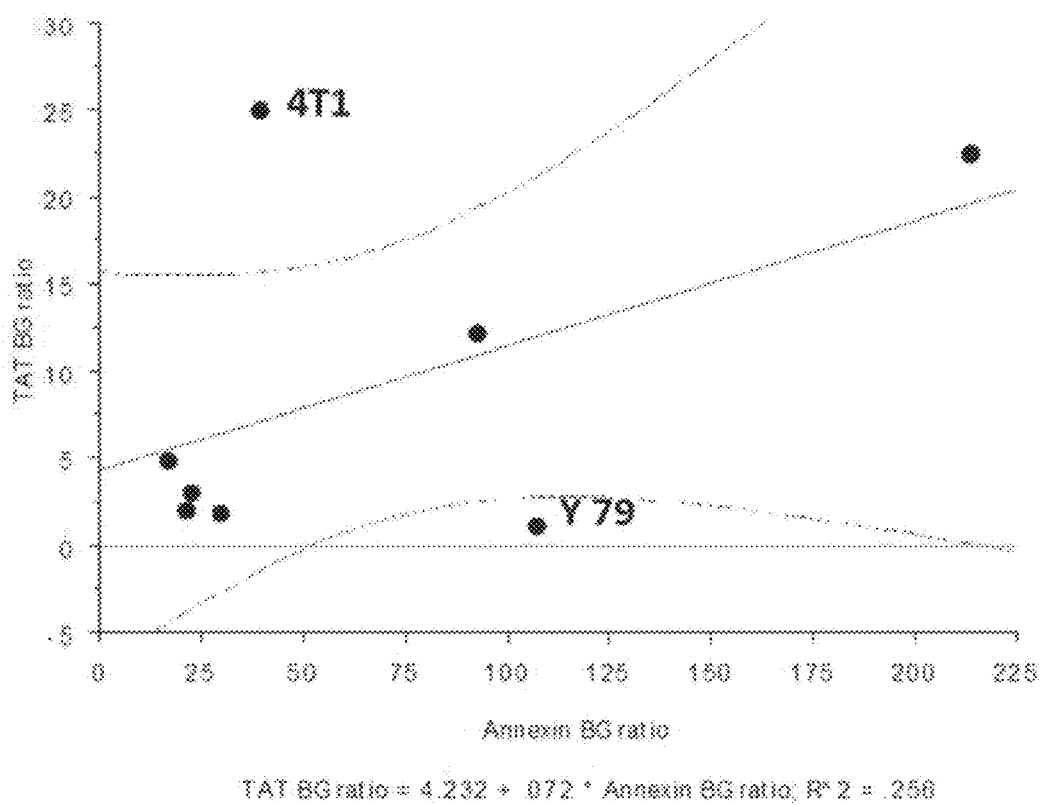
FIG. 11E depicts a plot and linear fit of FITC-TAT monomer fluorescence versus FITC-Annexin V fluorescence by each cell line tested.
Figure 11F:
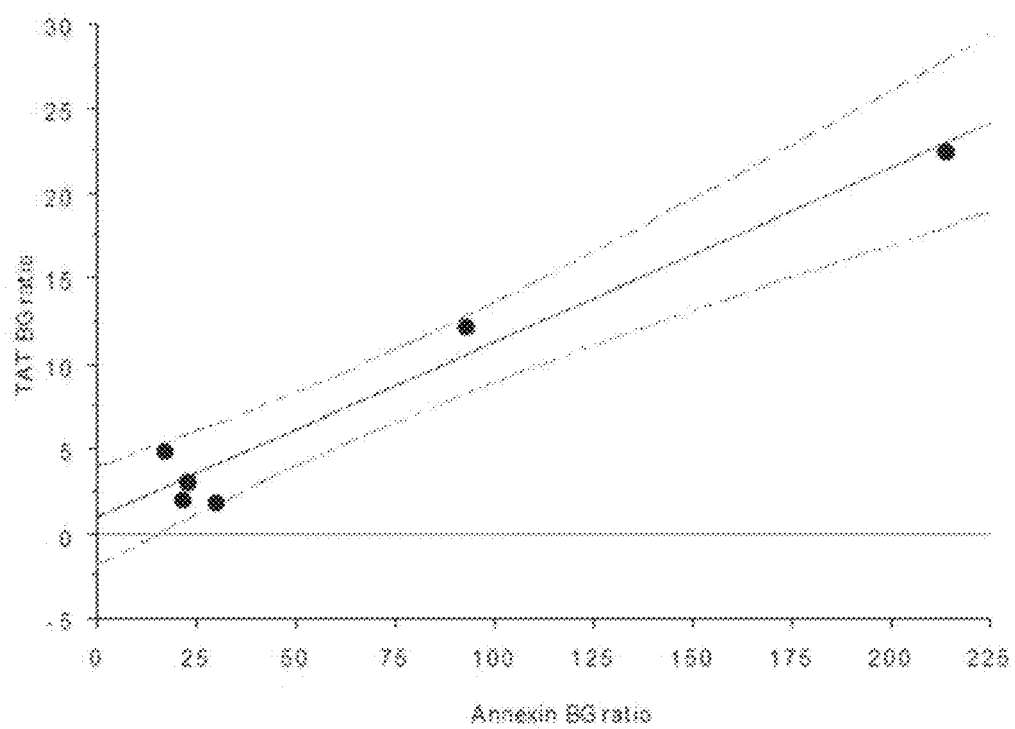
FIG. 11F depicts a plot and linear fit of FITC-TAT monomer fluorescence versus FITC-Annexin V fluorescence by each cell line tested except 4T1 and Y79.

Binding of Annexin by cancer cells. Uptake of Annexin V, a marker of anionic cell surface PS expression, was also observed on cell membranes of the 9L glioma cell line and three other cancer cell lines tested including 9L glioma, LLC (murine lung cancer), 4T1 (murine breast cancer) and SKOV-3 (ovarian cancer). While assessing Annexin V binding, PI was used to assess cell viability. Across the cell lines, 91% of 9L, 76% of LLC, 64% of 4T1 and 92% of SKOV-3 cells were viable (PI negative) and had binding of Annexin V. The cells were also assessed by flow cytometry and confocal microscopy as shown in FIGS. 11A-11D, respectively. FIGS. 11A and 11B show aspects of tumor cell affinity for Annexin V and TAT. Flow cytometry scatterplots show the binding of FITC-Annexin, a surrogate for anionic PS expression on the cell membranes of the cancer cell lines test (FIG. 11A). Confocal microscopy shows the green fluorescence indicating uptake of the cationic cell penetrating peptide TAT (as fluorescein-labeled TAT monomer) in the same cell lines (FIG. 11B). FIG. 11C depicts the fluorescence distribution for FITC-Annexin in treated cells (dark gray) and untreated cells (light gray). FIG. 11D provides a chart of mean fluorescence intensity by cell line showing Annexin binding. It was also observed that PI stained cells had greater binding of Annexin V than live cells. FIGS. 11E-11F show a linear correlation between fluorescein-labeled TAT monomer uptake and Annexin V binding. In FIG. 11F, the 4T1 and Y79 cell were excluded as outliers which yielded a $R^2$ value for the six cells lines of 0.96. These results demonstrate that PS expression and TAT uptake may be linearly related.

In vitro uptake of TAT by cancer cell lines. The cationic CPP TAT was observed to robustly target the cancer cell membranes of all lines tested as judged by confocal microscopy. The time course of TAT uptake was seen to be rapid. Using flow cytometry and confocal imaging, significant uptake of fluorescein labeled TAT monomer could be detected within 5 min after delivery. FIGS. 4A-4C show aspects illustrating the rapid uptake of fluorescein-labeled TAT monomer by 9L glioma cells. The time course of fluorescein-labeled TAT monomer uptake was determined both by flow cytometric and confocal microscopic analysis. Live cell gating (FIG. 4A) and the fluorescence distribution shift over time (FIG. 4A) show the change in fluorescein-labeled TAT monomer uptake for untreated control (−) and at times 0, 5, 10, and 15 min after exposure (FIG. 4B). Corresponding fluorescence microscopy at each time point (FIG. 4C) confirms the rapid uptake of fluorescein-labeled TAT monomer by tumor cells which can be seen (green fluorescence) within 5 min after exposure and increases over time.

Figure 12A:
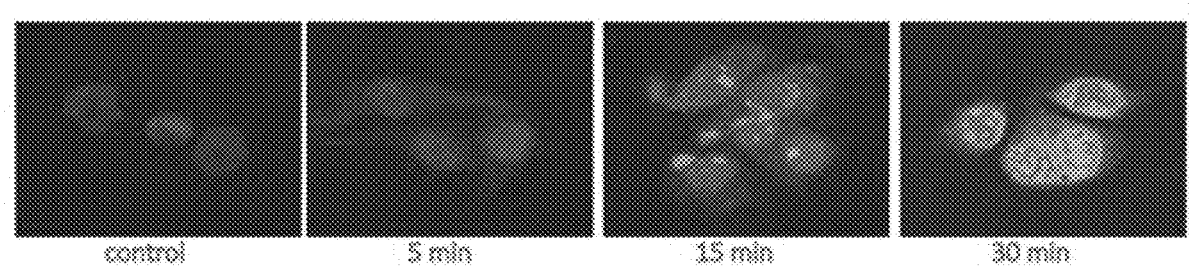
FIG. 12A depicts confocal microscopy at varying timepoints after exposure of 9L cells to FITC-labeled TAT monomer.
Figure 12B:
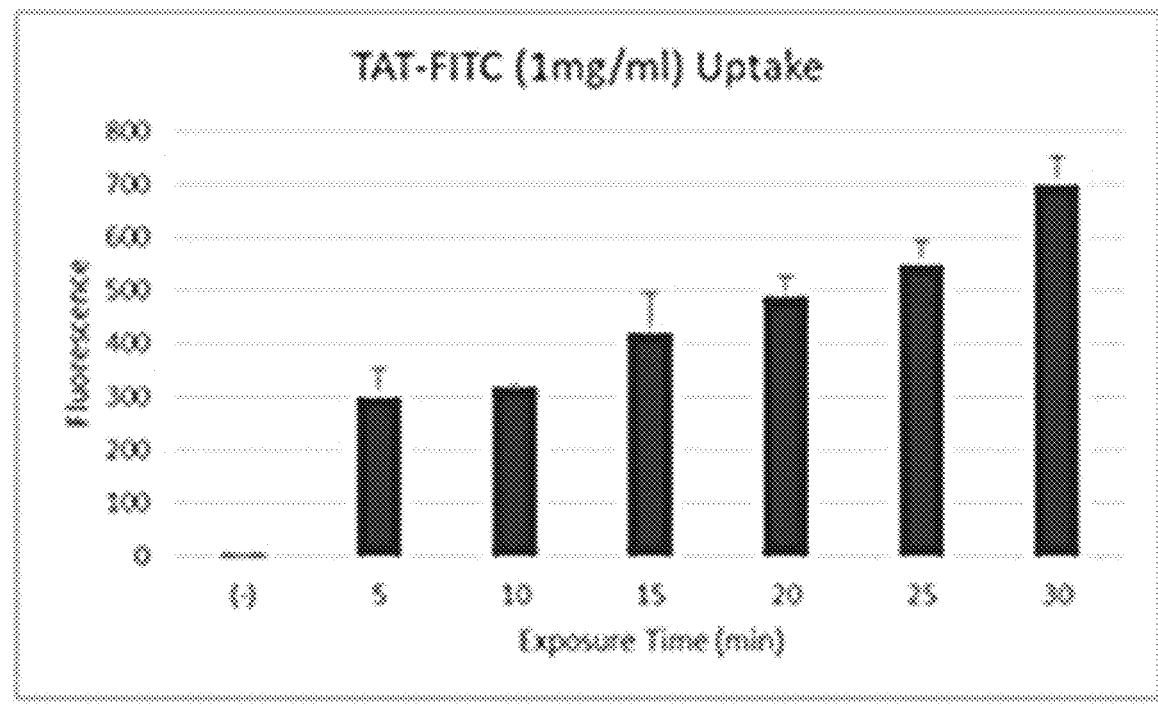
FIG. 12B depicts a chart of fluorescence over time by 9L cells after exposure to FITC-labeled TAT monomer.

TAT uptake studies were undertaken in 9L tumor cell lines using fluorescein labeled TAT monomer. The 9L-Luc cells were grown to 95% confluence verified by fluorescence microscopy. They were exposed to increasing doses of fluorescein-labeled TAT monomer for 5-30 minutes at a concentration of 1 mg/mL. After the period of exposure fluorescein-labeled TAT monomer was washed out. Cell uptake of TAT uptake was determined by fluorescence a Bio-Plex plate reader. With 490 nm excitation and 520 nm emission. Studies were conducted in triplicate and the mean value was reported. Results of this method are shown in FIG. 12B.

Figure 12C:
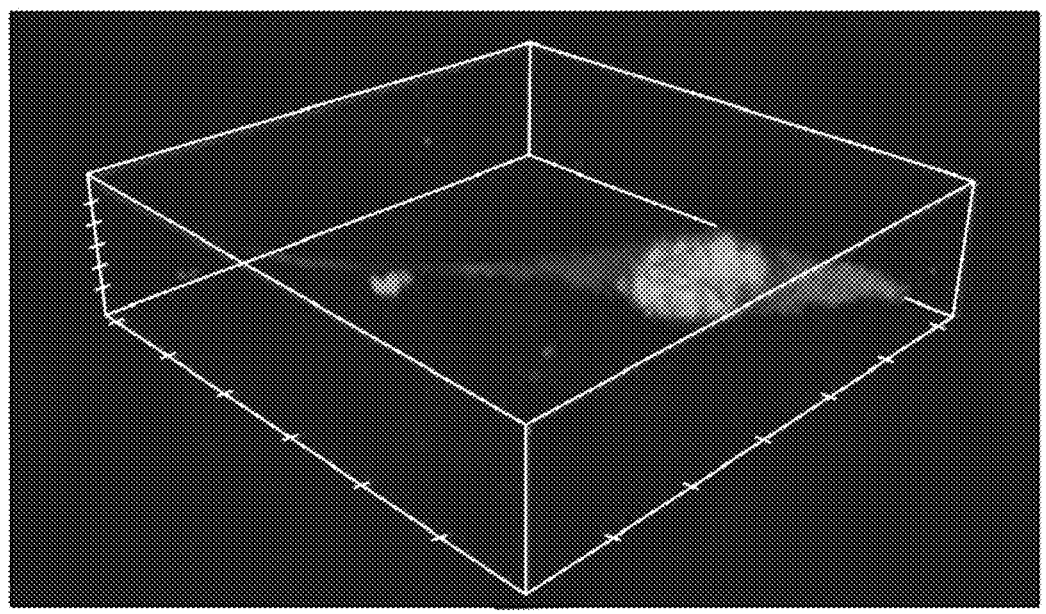
FIG. 12C shows a Z-stack image showing fluorescence due to FITC-labeled TAT monomer in the cytoplasm of a cell.

TAT rapidly targets the cytoplasm and localizes to the nucleus of targeted cells. Spectrophotometric analysis and confocal fluorescence microscopy show a robust uptake of fluorescein-labeled TAT monomer within 5 minutes of exposure to cell cultures (FIGS. 12A-12B). By 15 minutes after initial exposure, fluorescein-labeled TAT monomer localization both within the cytoplasm and nucleus can be seen (FIGS. 12A-12B). Three-dimensional maps created from Z stacking of confocal images confirm robust targeting of fluorescein-labeled TAT monomer to the cell nucleus at 30 minutes (FIG. 12C).

Thus, these results demonstrate that fluorescein-labeled TAT monomer and dimer were taken up by the 9L gliosarcoma cell lines and by other tumor cell lines, and that TAT oligomer conjugates present a viable method for delivery of payloads for treatment of tumor cells.

Example 2: In-Vivo Tumor Selective Drug Delivery

Uptake of fluorescein-labeled TAT dimer was tested in five rats with implanted 9L brain tumors and a control rat without a brain tumor. Three rats received a 0.25 mg dose while two rats received a 0.125 mg dose of the fluorescein-labeled TAT dimer.

Injection method: The injections were undertaken on anesthetized tumor implanted Fisher 344 rats. Surgical preparation on the day of tracer injection included tail vein cannulation, tracheostomy, carotid cannulation, and skull shaving for laser Doppler flow measurements. Hemodynamic and respiratory parameters were continuously monitored. FA-IA delivery was achieved by inducing transient cardiac arrest by bolus injections of esmolol, adenosine, and cold saline. During the arrest 40-50 µl boluses of the fluorescein-labeled TAT dimer were injected into the carotid artery. All drugs were injected pneumatically by a Parker Picospritzer 3 micro-injector that was controlled by a signal generator (Agilent 33220A). 30-35 µl pulses were generated to a total injected volume of 1 ml. During the injection the heart rate and the blood pressure was reduced to about 10-15% of baseline values. As a result blood flow of the brain decreased for 1 to 2 minutes during injections of the fluorescein-labeled TAT dimer. Recovery followed and physiological parameters returned to near baseline values within 5 minutes. The animals were sacrificed after fifteen minutes and uptake of the fluorescein-labeled TAT dimer was determined by fluorescence imaging of the harvested brain tissue.

Gross tumor imaging results: Imaging was performed using a photon counting Evolve 512 camera a 470 nm light source was used for excitation and the brain images were acquired using a 520 nm band pass filter under rigorously standardized conditions. Each image is standardized by two control samples on each side to ensure even excitation.

Figure 13A:
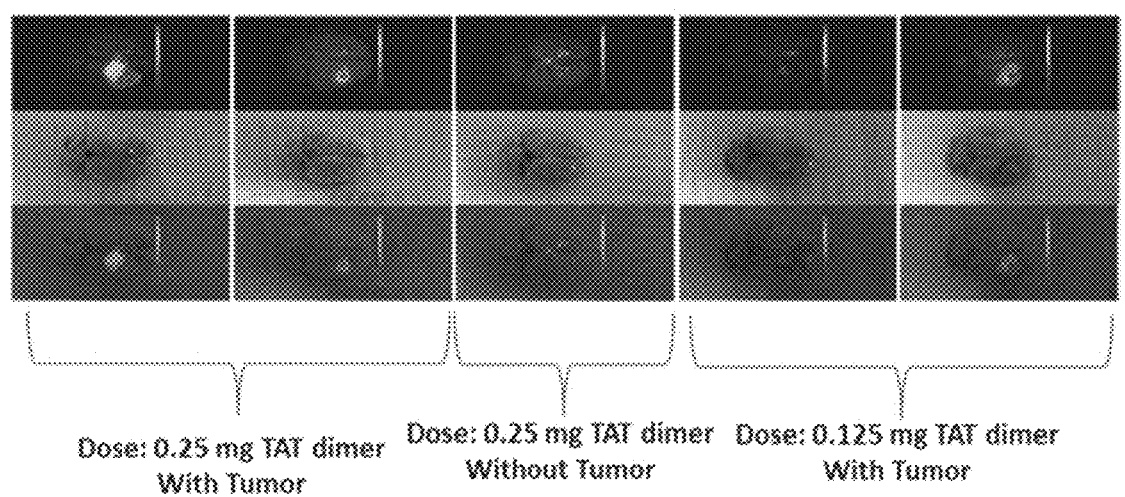
FIG. 13A depicts rat brains with implanted 9L glioma tumors after exposure to FITC-labeled TAT dimer using multi-spectral imaging, gross imaging and superimposed images.

FIG. 13A depicts surface images. As shown in FIG. 13A, four animals showed evidence of a tumor on the right cerebral cortex (middle row) and one animal did not show evidence of a tumor (shown in the middle column) The top row of images show tissue fluorescence while the bottom row show overlap between the fluorescence and gross specimen pictured in the middle row. As shown, all animals with gross tumors showed tumor-selective uptake of the fluorescein-labeled TAT dimer.

In a separate experiment, 14 days post-implantation of 9L glioma tumors, eight rats were anesthetized and prepared for IA-TCH. Blood flow reduction for TCH was achieved by bolus IV injection of adenosine and esmolol that were flushed with cold saline. Rats were injected IA with 1 mL of fluorescein-labeled TAT monomer at 0.5 mg/mL. Animals were sacrificed 15 minutes after TAT injection. Brain tissue was harvested. Gross sections were imaged with multi-spectral imaging (MSI) system using a photon counting cooled fluorescence camera. A 490 nm light was used for excitation while 525 nm filter was used for imaging the emitted light.

Figure 13B:
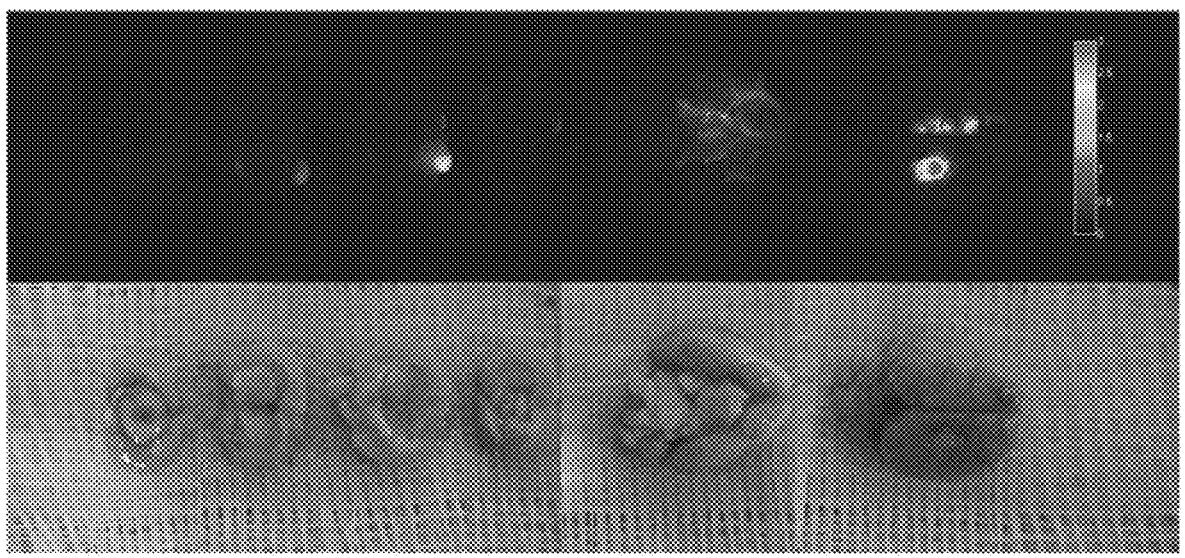
FIG. 13B depicts rat brains implanted with 9L glioma tumors after exposure to FITC-labeled TAT monomer using multi-spectral imaging and gross imaging.
Figure 13C:
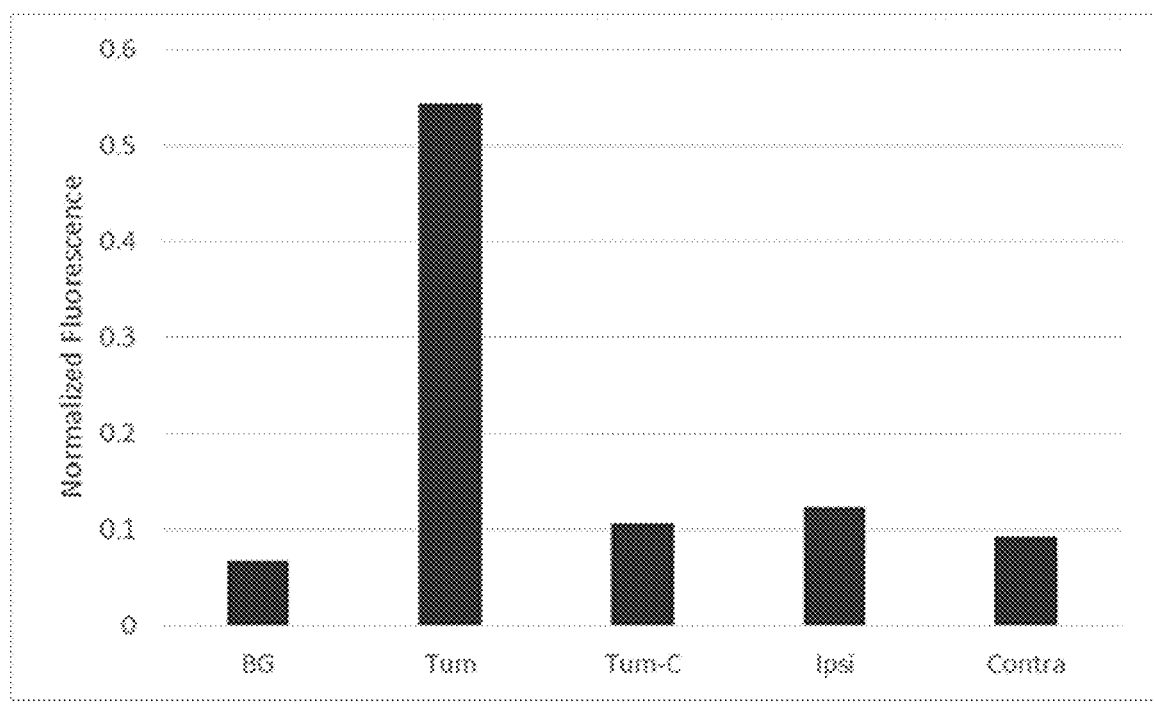
FIG. 13C depicts a chart of normalized fluorescence by brain region for the rat brains shown in FIG. 13B.
Figure 13D:
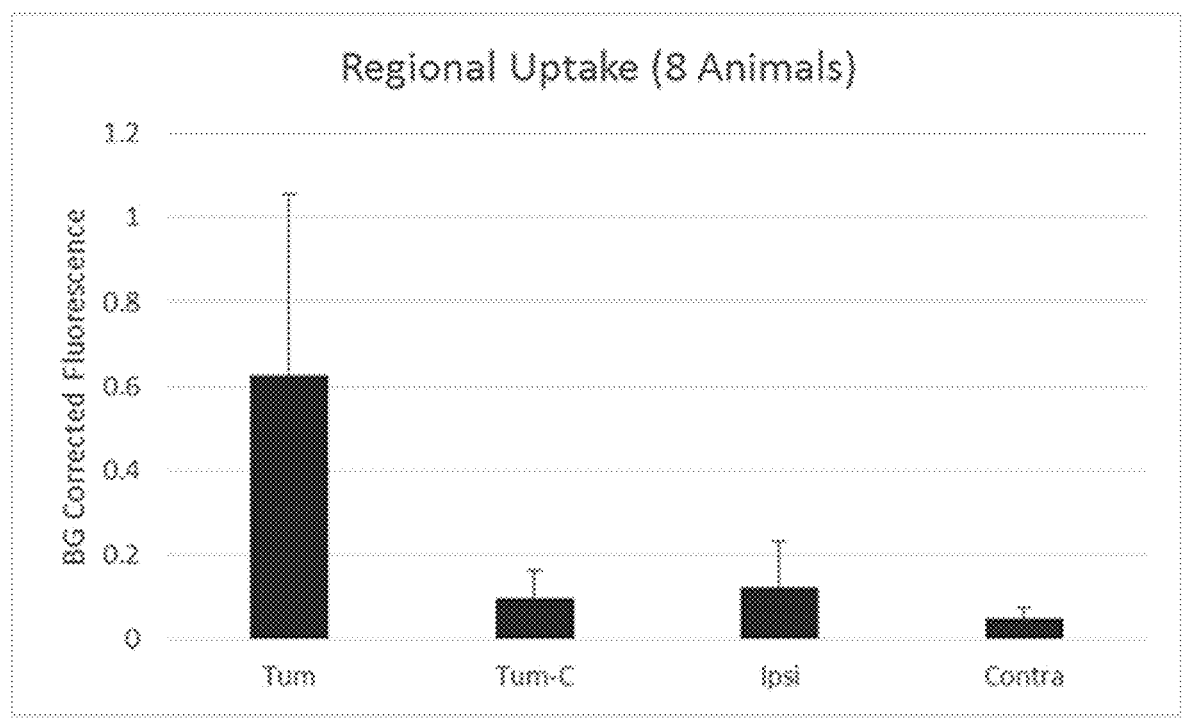
FIG. 13D depicts a chart of background corrected fluorescence by brain region for the same 8 rats as shown in FIG. 13B.

FIG. 13B shows multi-spectral images of the gross rat brain tissue (top row) and normal images of the same gross rat brain tissue (bottom row). FIGS. 13C-13D show regional uptake of fluorescence by region for normalized fluorescence (FIG. 13C) and background corrected fluorescence (FIG. 13D) of all eight animals where BG=background; Tum=tumor; Tum-C=contralateral region corresponding to tumor; Ipsi=ipsilateral region; and Contra=remaining contralateral hemisphere. These data show tumor-specific uptake of the fluorescein-labeled TAT monomer by tumors with a 5× greater uptake in the tumor compared to adjacent regions and a 13× concentration in the tumor versus the opposite side.

Example 3: Targeting Glioma by Intraarterial Delivery of Cell Penetrating Peptides IA-TCH delivery of TAT oligomer conjugates was compared to conventional IV delivery using fluorescein-labeled TAT molecules.

Comparison of L4-TCH and IV TAT delivery. Fisher 344 rats weighing about 200 g were utilized. During initial surgery under ketamine-xylazine isoflurane anesthesia $5\times10^5$ 9 L cells were implanted 3 mm below the skull and 2-3 mm posterior and lateral to the bregma through a 1 mm craniotomy. 14-16 days post-implantation, when tumors are about 3-4 mm wide and the animals are not distressed in any way, administration of fluorescein-labeled TAT monomer was performed. The animals were assigned separately to IV and IA-TCH groups. On the day of drug delivery, animals were sedated with isoflurane and injected with ketamine/xylazine. The tail vein was cannulated for intravenous access. Under aseptic precautions, a tracheostomy and carotid cannulation were performed. Anesthesia was maintained by mechanical ventilation with isoflurane (1.8-2.2%). Thereafter animals were turned prone on a stereotactic frame. The skull was exposed and the region of tumor implantation was shaved to transparency. A laser Doppler probe was implanted on the skull with the aid of a plastic holder to assess cerebral/tumor blood flow. Rectal temperature, pulse pleth (volume), pulse oxygen saturation, EKG, expired and inspired gas composition, brain and skin blood flow with lase Doppler were continuously monitored.

Transient cerebral hypoperfusion and fluorescein-labeled TAT monomer injection. IA injections were made during TCH by the following method. Reduction of blood flow was achieved by bolus IV injections of adenosine (2 mg) and esmolol (2 mg), and cold saline (1.5 mL at 4° C.). Typically such an intervention decreases cerebral blood flow to about 20% of the baseline. The heart rate response varies from sinus bradycardia to a sinus pause. However, physiological parameters rapidly recover within 3-5 minutes. Bolus injections of 40-50 µl of fluorescein-labeled TAT monomer every 2 seconds were performed using a pneumatically driven 1 mL syringe that was driven by a Parker Picospritzer III micro-injector controlled by an Agilent 22330A signal generator. For each animal, a test IA injection was done prior to the onset of hypotension to ensure delivery of the desired injection volume and the injection sequence was resumed after bolus IV injections of hypotensive drugs. For IV fluorescein-labeled TAT monomer injections, the pulse sequence was delivered intravenously without hypotension.

Physiological parameters. Key parameters included inspired and expired gas composition, laser Doppler skin and brain/tumor blood flow, EKG for heart rate, pleth pulse, oxygen saturation, and rectal temperature which were continuously monitored. Data were analyzed at four time points: baseline, at the time of IA injection, 5 minutes after the start of injection, and at the end of the experiment. Since the uptake of fluorescein-labeled TAT monomer was very rapid, animals were sacrificed at 15 minutes by bolus injection of propofol 3 mg and KCl. Immediately after sacrifice, brain tissue was harvested for imaging. All physiological data was recorded at 200 Hz by a Mac Lab data collection system.

Postmortem imaging. In preliminary experiments, known quantities of fluorescein-labeled TAT monomer was dissolved in intralipid and imaged using the multi-spectral imaging system. The multi-spectral imaging system contained two 470 nm light emitting diodes that evenly illuminated the test sample (Thor Labs Inc., NJ). An Evolve-512 (Photometerics Inc., Tucson, AZ) photon multiplying charge coupled device was used to image the sample through a 530 nm band pass filter. The camera is capable of performing background corrections and measuring the photon counts from the region of interest. Imaging conditions (sample, light source, and camera placements) were standardized throughout the experiment.

Immediately after sacrifice, the brains were harvested and immersed in cold saline. Samples of the injected fluorescein-labeled TAT monomer (0.5 mg in 1 mL of calcium and magnesium-free phosphate buffer saline, pH 7.2) were obtained from the dead space of the syringe after use. Samples were loaded on two capillary glass tubes that were placed alongside the tissue samples. Gross and sectional images were obtained in color and with fluorescence as shown in FIGS. 14A-14F. Typically each specimen had 4 sections, one of which through the plane of the tumor was sent for frozen section, the remainder were placed in paraformaldehyde for paraffin blocks and histological sectioning.

Frozen sections (10 μm thick) were imaged under a Nikon confocal microscope with 470 nm excitation. Due to the large size of the tissue sample, small sections of images were obtained and then assembled together. An adjacent section was stained with hematoxylin and eosin to confirm the size and location of the tumor. The total fluorescence in the tumor region, in the non-tumor ipsi-lateral hemisphere, and in the corresponding region contra-lateral to the tumor was quantified. The contra-lateral hemisphere was used for background correction.

Statistical analysis. All data, unless otherwise specified, are presented as mean and standard deviation. The data were analyzed by factorial and repeated measures ANOVA. A P$p$ value of <0.05 was considered significant for IV and IA-TCH comparisons. While a P<0.0083 was significant for repeated measures, ANOVA using Bonferroni-Dunn correction was used for four comparisons: baseline, injection, 5 minutes and end experiment. Analysis was done using Stat View 5.0 software (SAS Institute Inc., Cary, NC).

Figure 14A:
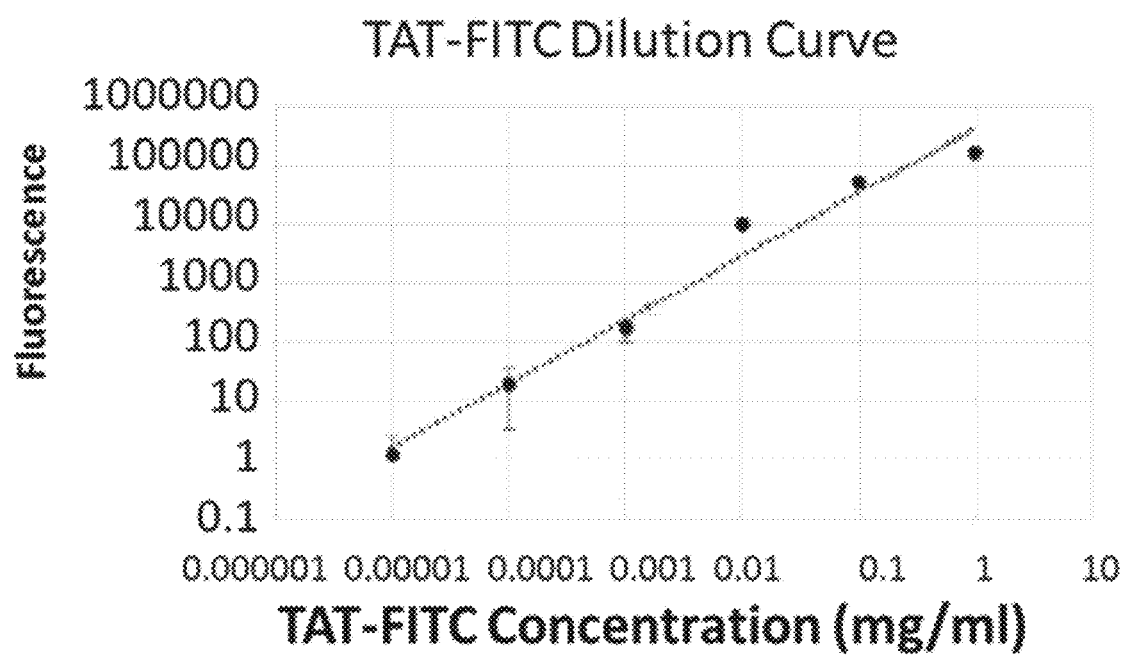
FIG. 14A depicts a dilution curve for fluorescence versus FITC-labeled TAT monomer concentration.
Figure 14B:
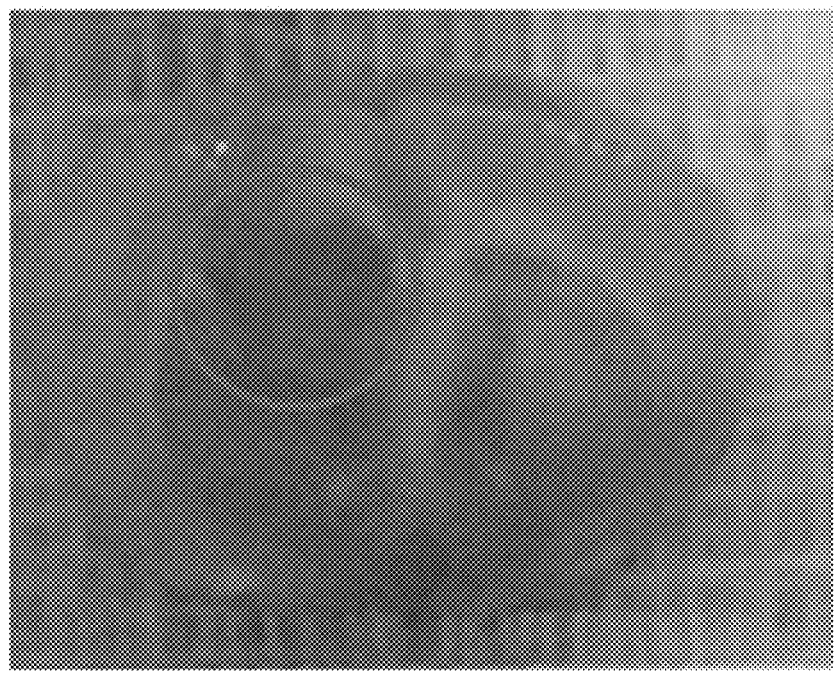
FIG. 14B depicts a gross image of a rat brain with an implanted 9L glioma tumor (indicated by the circle).
Figure 14C:
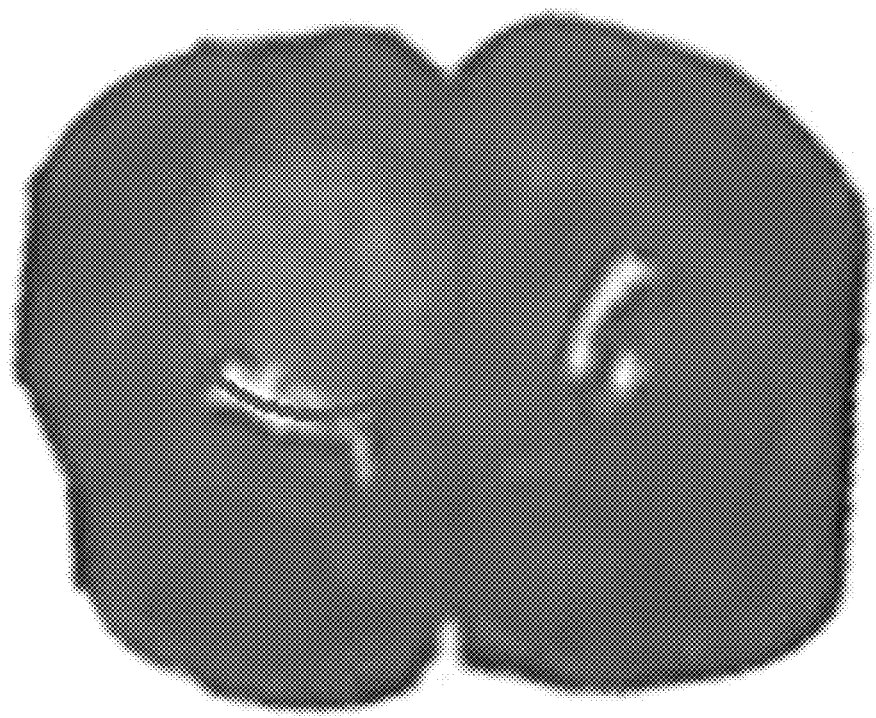
FIG. 14C depicts a hematoxylin and eosin stained slice of the rat brain depicted in FIG. 14B.
Figure 14D:
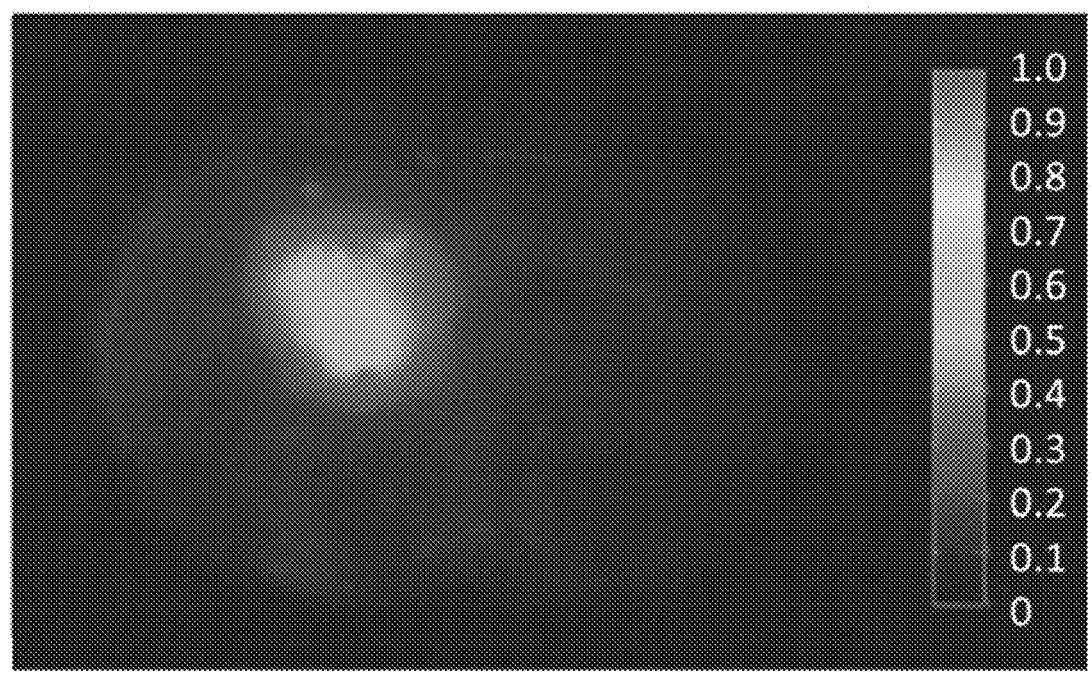
FIG. 14D depicts post-mortem multi-spectral imaging of the rat brain shown in FIG. 14B.
Figure 14E:
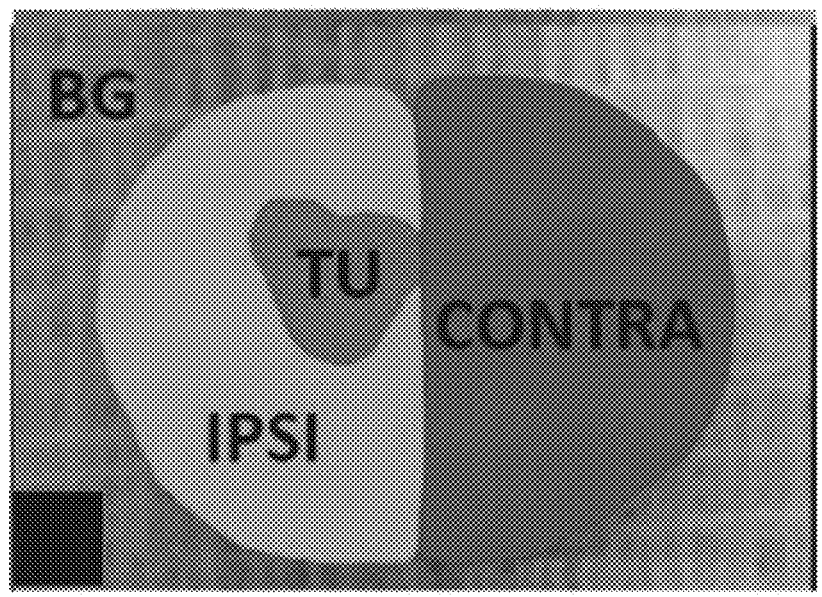
FIG. 14E depicts a schematic brain section corresponding to the rat brain shown in FIG. 14B.
Figure 14F:
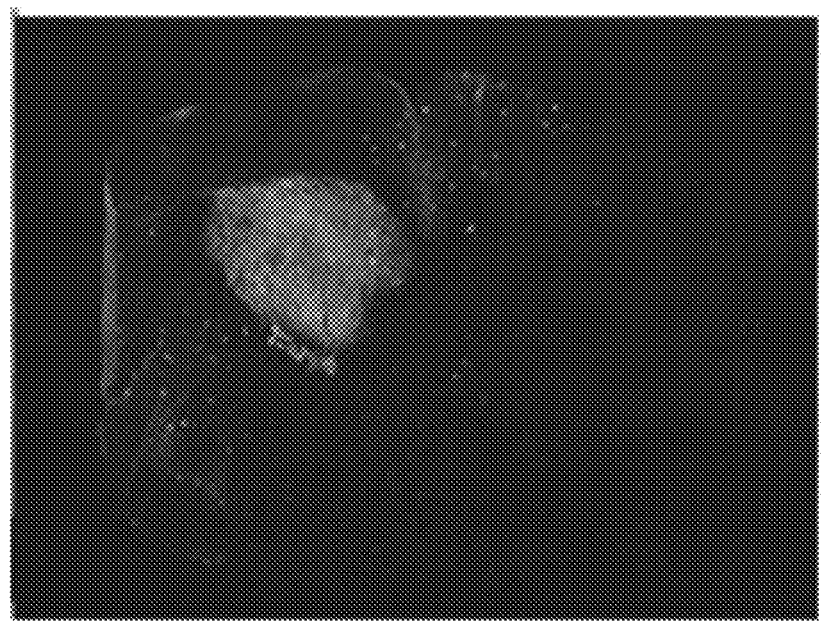
FIG. 14F depicts a confocal microscopy image of a frozen slice of the rat brain shown in FIG. 14B.

FIGS. 14A-14F show aspects of the assessment of fluorescein-labeled TAT monomer uptake by glioma implants. A linear correlation was observed between fluorescein-labeled TAT monomer dissolved in a tissue phantom using multi-spectral imaging (FIG. 14A). Gross (FIG. 14B) and hematoxylin-eosin stained (FIG. 14C) tissue cross sections show the location of the tumor (circled). Post-mortem multispectral imaging shows the uptake of fluorescein-labeled TAT monomer (FIG. 14D). A schematic brain section indicates the regions of fluorescence quantification used for multi-spectral imaging in each specimen (FIG. 14E). Post mortem confocal imaging of the frozen section indicates high density FITC fluorescence (green) within the tumor (FIG. 14F).

In vivo uptake of fluorescein-labeled TAT monomer after IA-TCH versus IV. The tumor uptake of fluorescein-labeled TAT monomer by IA-TCH and IV delivery methods in 9L tumor implants rats was assessed using post-mortem fluorescence tissue imaging. FA-IA delivery was achieved by inducing transient cardiac arrest, by bolus injections of esmolol, adenosine, and cold saline. During the arrest 40-50 μl boluses of FITC-TAT were injected into the carotid artery. In tumor bearing rats no differences were observed in baseline data with regards to weight and physiological parameters between the IV and the IA-TCH groups. As expected there were significant differences at the time of drug injection but the physiological parameters were essential comparable at baseline and at 5 minutes and at the end of the experiment, Table 5. 9L glioma uptake of fluorescein-labeled TAT monomer in gross specimens was assessed by multispectral imaging and confocal microscopy with concordant findings.

Figure 15:
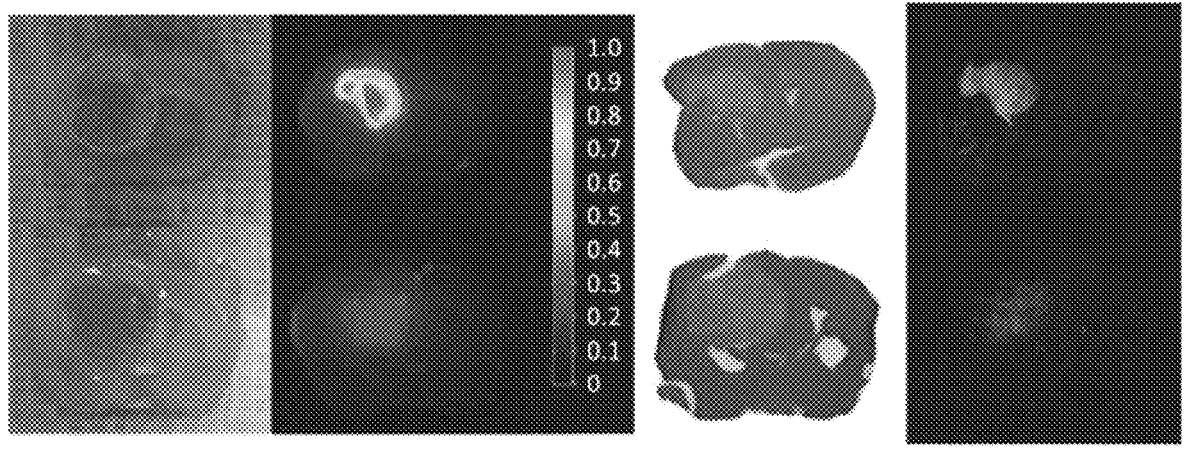
FIG. 15 depicts side-by-side gross, multi-spectral, hematoxylin and eosin stained and confocal microscopy images of rat brains with implanted 9L glioma tumors after IA-TCH (top) and IV (bottom) administration of FITC-labeled TAT monomer.

Tumor uptake of fluorescein-labeled TAT monomer was assessed by two methods. Gross imaging of the tumor specimen revealed preferential tumor uptake of fluorescein-labeled TAT monomer by 9-L xenografts that was four fold greater by the IA-TCI-1 method as compared to the IV method. Both methods of delivery showed a greater uptake by the tumor compared to the adjacent normal brain or the contralateral side (FIG. 15). However the preferential tumor uptake of fluorescein-labeled TAT monomer was much greater with IA-TCH than by the IV method. Representative gross brain sections after IA-TCH (top) and IV (bottom) delivery are shown in FIG. 15 left panel (the circle indicates the tumor). Corresponding multispectral images show higher intensity of signal within the tumor after IA-TCH (FIG. 15 second from left panel) as compared to IV injection. Confocal microscopy fluorescence measurements also revealed a nearly four-fold increase in tumor uptake with IA-TCH delivery compared to IV delivery. The results by gross fluorescence images were confirmed by confocal microscopy of postmortem tissue sections (Table 5). The IA-TCH method generated 6.1-fold, while the IV method generated 2.3-fold, greater tumor concentration compared to brain tissue on the ipsi-lateral side. Overall the IA-TCH method was 4× more effective than the IV method. Higher intensity green fluorescence signal within the tumor after IA as compared to IV injections confirms the superior efficiency of IA-TCH delivery to IV delivery. A similar analysis was performed on frozen brain sections. Representative hematoxylin and eosin stained sections corresponding stitched confocal microscopy are shown in FIG. 15 right panel.

Table 5 summarizes the physiological changes observed during delivery of fluorescein-labeled TAT monomer by IA-TCH compared to IV delivery. Data are expressed as mean±standard deviation. As shown in Table 6, quantitative multispectral imaging of gross specimens indicates that the IA-TCH method generates 6.1-fold greater tumor deposition compared to non-tumor brain tissue in the ipsilateral hemisphere, normalized to the non-tumor contralateral hemisphere. In contrast, the IV method of delivery generates only 2.4-fold greater tumor deposition compared to non-tumor brain tissue in the ipsilateral hemisphere. A similarly robust and statistically significant result was seen when measurements where performed using confocal microscopy of frozen specimens (Table 7). In Tables 5-7, * indicates using repeated measures of ANOVA with post hoc Bonferroni-Dunn correction, there is a difference from all other stages, P<0.0083; #indicates using factorial ANOVA, there is a difference between two groups, P<0.05; a indicates Different from base; and b indicates Different from base and injection.

TABLE 5

Comparison of IA-TCH and IV delivery of fluorescein-labeled TAT monomer

| Physiological changes (n = 6) | | Base | Injection | 5 min | End |
|---|---|---|---|---|---|
| Temp (° C.) | IA-TCH | 37.1 ± 1.3 | 36.6 ± 1.3 | 36.6 ± 1.1 | 36.9 ± 1.1 |
| | IV | 35.9 ± 0.9 | 35.9 ± 0.9 | 36.1 ± 0.9 | 36.5 ± 1.0 |
| ETCO$_2$ (% Δbase) | IA-TCH | 100 ± 0 | 54 ± 50 | 71 ± 17 | 92 ± 27 |
| | IV | 100 ± 0 | 75 ± 39 | 85 ± 37 | 86 ± 14 |
| Isoflurane (ET %) | IA-TCH | 2.2 ± 0.2 | 0.8 ± 0.9* | 1.8 ± 0.8 | 2.2 ± 0.4 |
| | IV | 2.2 ± 0.3 | 0.4 ± 0.1* | 2.1 ± 0.2 | 2.1 ± 0.3 |
| SaO$_2$ (%) | IA-TCH | 98 ± 2 | 92 ± 11* | 95 ± | 798 ± 3 |
| | IV | 100 ± 5 | 97 ± 4 | 97 ± 4 | 99 ± 2 |
| HR (BMP) | IA-TCH | 289 ± 19 | 63 ± 41*,# | 273 ± 59 | 310 ± 11 |
| | IV | 267 ± 17 | 274 ± 31 | 267 ± 68 | 283 ± 10 |
| Sk · BF (% Δbase) | IA-TCH | 100 ± 0 | 18 ± 10* | 104 ± 38 | 92 ± 16 |
| | IV | 100 ± 0 | 144 ± 50a,# | 106 ± 28 | 116 ± 30 |
| CBF (% Δbase) | IA-TCH | 100 ± 0 | 29 ± 26 | 90 ± 32 | 81 ± 13 |
| | IV | 100 ± 0* | 122 ± 21# | 73 ± 13b | 73 ± 12b |

TABLE 6

Uptake of fluorescein-labeled TAT monomer by multi-spectral imaging of gross specimens

| Parameter (n = 6) | IA-TCH | IV |
|---|---|---|
| Tumor fluorescence (AU) | 0.277 ± 0.139# | 0.063 ± 0.030 |
| Ipsilateral fluorescence (AU) | 0.047 ± 0.019# | 0.028 ± 0.005 |
| Contralateral fluorescence (AU) | 0.029 ± 0.012 | 0.25 ± 0.004 |
| Tumor/contralateral ratio | 10.1 ± 4.9# | 2.7 ± 1.5 |
| Tumor/ipsilateral ratio | 6.1 ± 2.6# | 2.4 ± 1.2 |
| Ipsi/contra-lateral ratio | 1.7 ± 0.5# | 1.1 ± 0.3 |

TABLE 7

Uptake of fluorescein-labeled TAT monomer by confocal microscopy imaging of frozen sections

| Parameter (n = 6) | IA-TCH | IV |
|---|---|---|
| Tumor fluorescence (AU) | 1758 ± 474# | 528 ± 246 |
| Ipsi-lateral fluorescence (AU) | 353 ± 76# | 216 ± 65 |
| Contralateral fluorescence (AU) | 161 ± 94 | 205 ± 67 |
| Tumor/contralateral ratio | 13.8 ± 7.6# | 3.0 ± 1.4 |
| Tumor/ipsi-lateral ratio | 4.9 ± 0.7# | 2.4 ± 1.1 |
| Ipsi/contralateral ratio | 2.7 ± 1.4# | 1.1 ± 0.5 |

Thus, the tumor specificity and efficiency of FITC-TAT delivery was much greater after IA-TCH delivery than after IV delivery. No differences were observed in baseline data or after 5 min post-injection between the two groups (IA-TCH versus IV) with regard to clinical and other physiological parameters. As expected, there were significant differences noted in the physiological parameters at the time of drug injection secondary to pharmacological induction of TCH (Table 5).

These experiments show the feasibility of tumor selective drug delivery of TAT conjugates by IA injections during a coordinated reduction of cerebral blood flow (IA-TCH). Cytological studies showed uptake of TAT was applicable to other cancer cell lines. Collectively these results point to the potential of using TAT as a carrier for IA-TCH assisted drug delivery for the treatment of primary and secondary brain cancers and other malignancies.

An additional experiment was performed to assess the in vivo uptake of fluorescein-labeled TAT dimer by IA-TCH. About 14 days after 9L glioma tumor implantation, rats were anesthetized and prepared for TAT dimer delivery experiments. TAT dimer was conjugated with fluorescein such that its concentrations in post mortem samples could be determined immediately by multispectral imaging and confocal imaging. TAT dimer (0.25 mg) and monomer (0.125 mg) were tested using IA-TCH delivery both containing equal amounts of fluorescein were evaluated. The blood flow reduction was achieved by bolus IV injection of adenosine and esmolol that were flushed with cold saline. Animals were sacrificed 15 minutes after TAT injection. Brain tissue was harvested. Gross sections were imaged with multi-spectral imaging (MSI) system using a photon counting cooled fluorescence camera. A 490 nm light was used for excitation while 525 nm filter was used for imaging the emitted light.

Figure 16A:
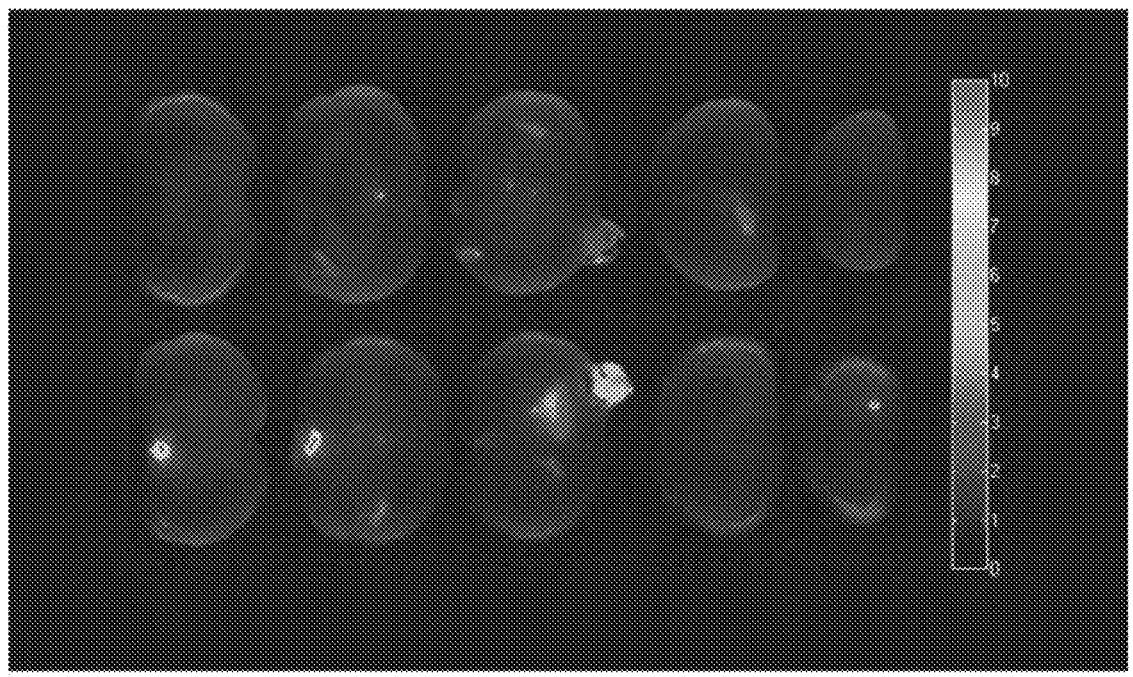
FIG. 16A depicts multi-spectral imaging of five rat brains treated with FITC-labeled TAT dimer.
Figure 16B:
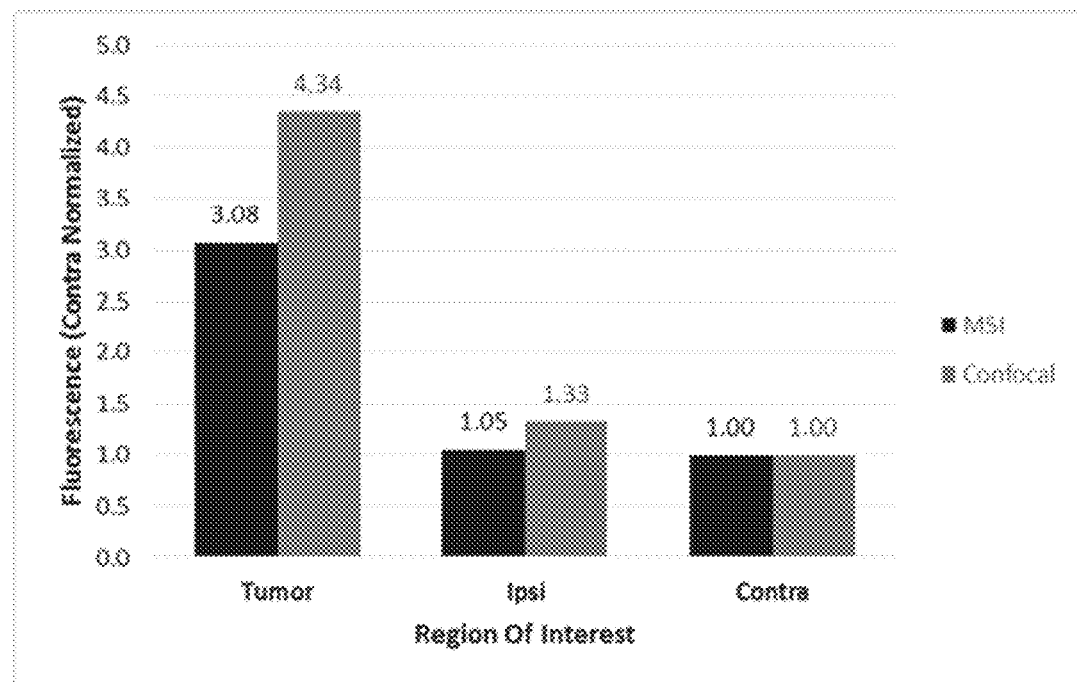
FIG. 16B depicts a chart showing contra normalized fluorescence by brain region by multi-spectral imaging (MSI) and confocal microscopy for the rat brains shown in FIG. 16A.
Figure 16C:
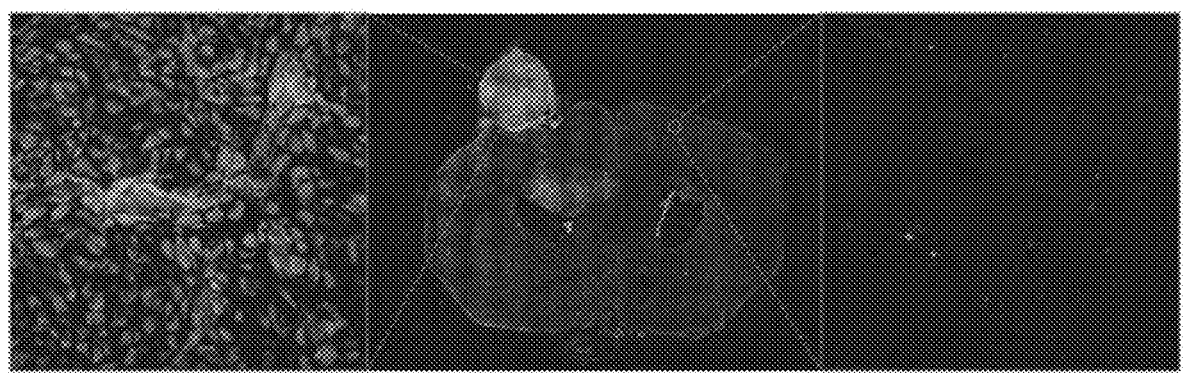
FIG. 16C depicts confocal microscopy images of the brain of a single rat from the images shown in FIG. 16A.
Figure 16D:
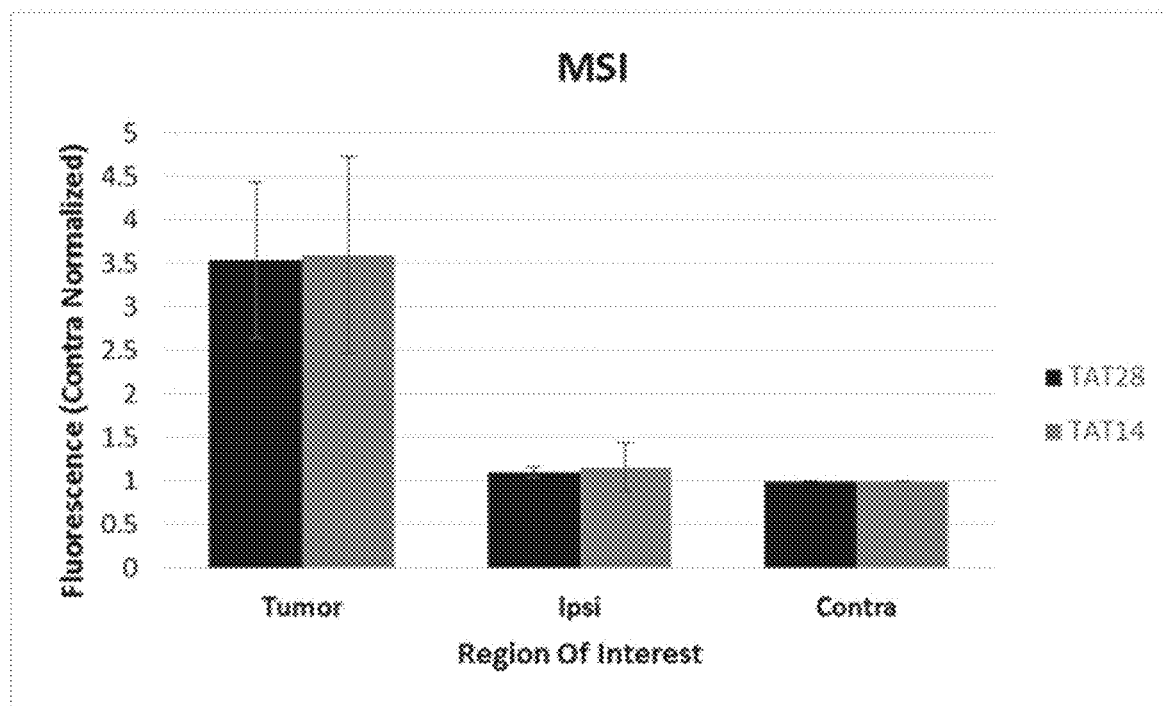
FIG. 16D depicts a chart of contra normalized fluorescence by brain region for rats treated with either FITC-labeled TAT monomer (TAT14) or FITC-labeled TAT dimer (TAT28) as measured by multi-spectral imaging.
Figure 16E:
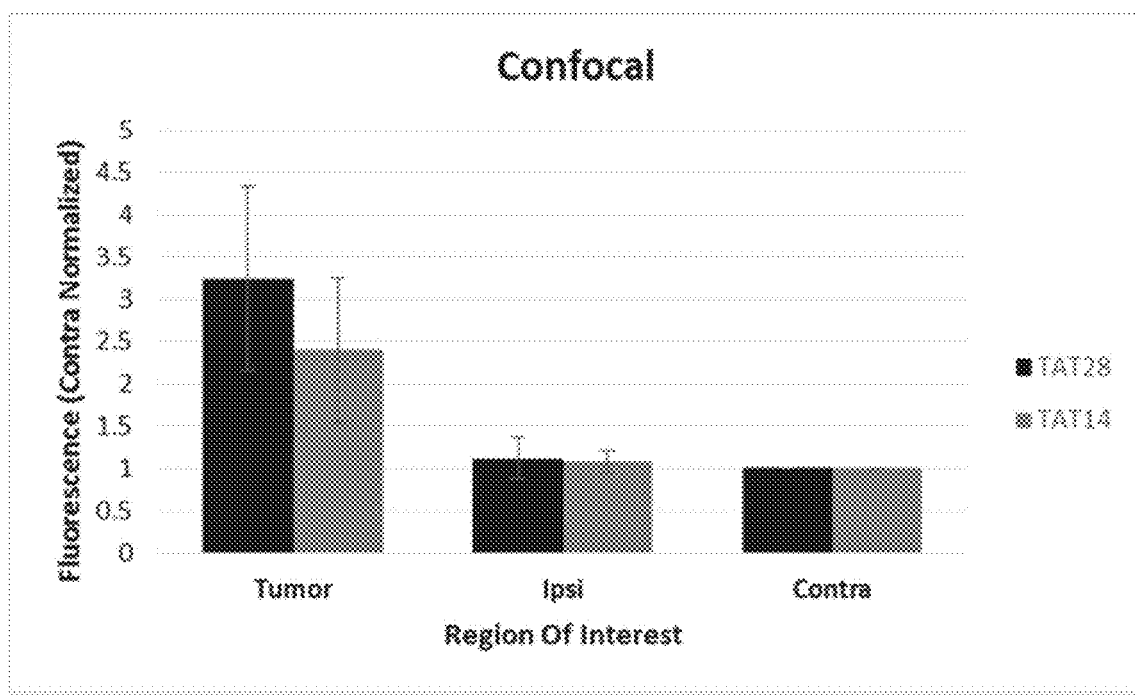
FIG. 16E depicts a chart of contra normalized fluorescence by brain region for rats treated with either FITC-labeled TAT monomer (TAT14) or FITC-labeled TAT dimer (TAT28) as measured by confocal microscopy.

Five rats were tested for each monomer and dimer. FIGS. 16A-16C show multi-spectral imaging of the five rat brains treated with fluorescein-labeled TAT dimer (FIG. 16A), fluorescence by multi-spectral imaging and confocal microscopy by brain region (FIG. 16B) and confocal microscopy images for a single rat. The bar charts in FIGS. 16D-16E show the tumor uptake relative to the non tumor regions of the brain. Both monomer and dimer were able to achieve tumor selective drug delivery. Confocal microscopy revealed greater uptake of the dimer compared to monomer.

The uptake of monomer and the dimer was similar with MSI imaging. Confocal imaging revealed greater uptake of the dimer. When combined with cytological studies (Expt 6) particularly with heparin block of uptake we believe that the dimer is a better carrier for drug delivery to 9L gliomas. Other tumors might show subtle differences in uptake however the IA-TCH method seems to be particularly suited for delivery of cationic peptides as carriers for targeting cancers.

Example 4: Feasibility of TAT-Guided Intra-Arterial Doxorubicin to Gliomas

The purpose of this example is to demonstrate that intra-arterial injection of TAT can target brain tumors with high degree of selectivity, and furthermore, that TAT can be conjugated to doxorubicin for delivery to brain tumors.

Methods

Animal preparation, IA-TCH injection, and brain tumor implantation. Animal protocols were approved by the Columbia University Institutional Animal Care and Use Committee (IACUC). Studies were primarily conducted on Sprague-Dawley rats weighing 250 to 300 grams. In the case of electron multiplying charge-coupled device imaging studies, Fisher 344 rats implanted with 9L brain tumors were utilized. The surgical preparation including anesthesia, carotid and femoral cannulation, cerebral blood flow and vital sign monitoring, as well as in vivo fluorescence imaging have been previously described in detail.

IA injections of cell-penetrating peptides (CPPs) were made during TCH as 65 μL pulses totaling 1 ml in volume. TCH was produced by a bolus injection of adenosine, esmolol, and cold saline. Animals were allowed to hemodynamically recover from TCH and euthanized 10 minutes after injection. Uptake of CPPs was assessed with a fluorescence camera and with confocal fluorescence microscopy.

For in vivo tumor delivery studies, rats were implanted with C6 brain tumor cells as previously described. Ten days after tumor implantation the animals received IA-TCH injection of 0.5 mg fluorescein-labeled TAT monomer using the methods described above. They were scarified 10 minutes later and the brains were harvested and sectioned.

Cell-penetrating peptides. Two experimental cell-penetrating peptides were tested: 1. octaarginine, also called $(Arg)_8$ or R-8 (SEQ ID NO: 13) and 2. trans-activator of transcription or TAT (Lifetien Inc.). The 14 amino acid peptide sequence for TAT is Gly-Arg-Lys-Lys-Arg-Arg-Gln-Arg-Arg-Arg-Pro-Pro-Gln-Gln-COOH (SEQ ID NO: 11). Both cell-penetrating peptides (CPPs) were labeled with fluorescein so that their distribution could be identified by multispectral imaging and with fluorescence microscopy of the frozen brain sections.

Fluorescence and electron multiplying charge-coupled device imaging. Fluorescence imaging was done with a white light excitation through a 470 nm filter with central frequency. Emission was observed through a 520 nm band pass filter using a fluorescence camera (Prosilica GE™ AVI Technologies Inc.). All images were normalized to the background and to the injected FITC-TAT concentrations—a sample of which was imaged alongside in a capillary tube.

In addition to the standard fluorescence imaging described above, we assess tumor uptake of TAT-FITC using a higher resolution, quantitative tool utilizing an electron-multiplying charge coupled device. To accomplish this we used two warm white light LEDs to evenly illuminate the tissue samples through a narrow (10 nm) band pass filter with 470 nm central transmission (Thor Labs, New Jersey). An Evolve 520 high sensitivity electron multiplying charge-coupled device (Photometeric Inc. Tucson, AZ) was utilized while using a 520 nm narrow band pass filter. Each sample was normalized to the background and to the injected drug concentrations. Four 2 mm sections were interrogated for each specimen on either side of the plane of tumor implantation. The data was corrected for ambient light, tissue independent background fluorescence, and contralateral hemisphere tissue fluorescence.

TAT-Dox synthesis. TAT-conjugated doxorubicin (TAT-Dox) was custom synthesized using the method described by Shi et al (Fleet Bioprocessing, Hants, UK) to yield a conjugate with doxorubicin N-terminally linked to the TAT peptide. A 5.8 ml solution containing doxorubicin hydrochloride (8.04 mg/ml) and triethylamine (TEA) (2.81 mg/ml) was prepared in anhydrous DMF. To this 1.1 equivalents of SMP (also called BMPS) was added as 3 ml of a 7.85 mg/ml solution in DMF. The mixture was roller-mixed at 20° C. and the reaction monitored by TLC using 70:30:3 chloroform:methanol:TEA. After approximately 2 hours DOX·HCl (Rf 0.48) was no longer visible by TLC and replaced by a DOX-SMP spot (Rf 0.79). The reaction mixture (8.8 ml) was split into two 50 ml centrifuge tubes. To each 30 ml of cold diethyl ether was added, resulting in the precipitation of Dox-SMP. This was centrifuged at 3000 g for 15 min. and the supernatant removed. The supernatant was stored at −40° C. to encourage further precipitation of Dox-SMP which were separated in the same fashion. The solids were pooled and washed with cold diethyl-ether (2×5 ml) and dried overnight by vacuum desiccation. 14.5 mg of Dox-SMP was dissolved in 3.15 ml DMF to which 2 ml (1 equiv) of TAT peptide (18.15 mg/ml) and 61 μl of TEA were added. The mixture was roller-mixed for 2 hours at 20° C. The reaction mixture was split into two 50 ml centrifuge tubes. To each 28 ml of cold diethyl ether was added, resulting in the precipitation of TAT-Dox. This was centrifuged at 3000 g for 15 minutes and the supernatant removed. The solids were pooled and washed with cold diethyl ether (2×5 ml) and dried overnight by vacuum desiccation to afford TAT-Dox in pure form in 40% yield.

In vitro cytotoxicity studies and uptake analysis. The relative cytotoxicity of fluorescein-labeled TAT monomer, TAT-Dox, and Dox were assessed using BrdU bioluminescence and MTT assays. 9L luciferase-expressing (9L-Luc) gliosarcoma cells (provided by Dr. Brian Ross University of Michigan, Ann Arbor) were incubated in a 96 well plate and grown to 95% confluence. 9L-Luc cells were cultured in Delbecco's Modified Eagle Medium (DMEM) with fetal bovine serum (10%), streptomycin (100 mg/ml) and penicillin (100 U/ml) and 1-glutamine 2 mM in an atmosphere 95/5% $O_2$ and $CO_2$ with 100% humidity. They were exposed to 1, 10, and 100 μM of the compound for 1-hour and assessed for viability at 24 hours. Data for all three assays was normalized to the survival of untreated cells. Assays were run in triplicate and fluorescence values were averaged for each treatment. The 3% hydrogen peroxide treated cells provided positive controls.

Cytological survival study data was analyzed by factorial ANOVA with Bonferroni/Dunn post hoc testing for multiple comparisons.

Results

Figure 17:
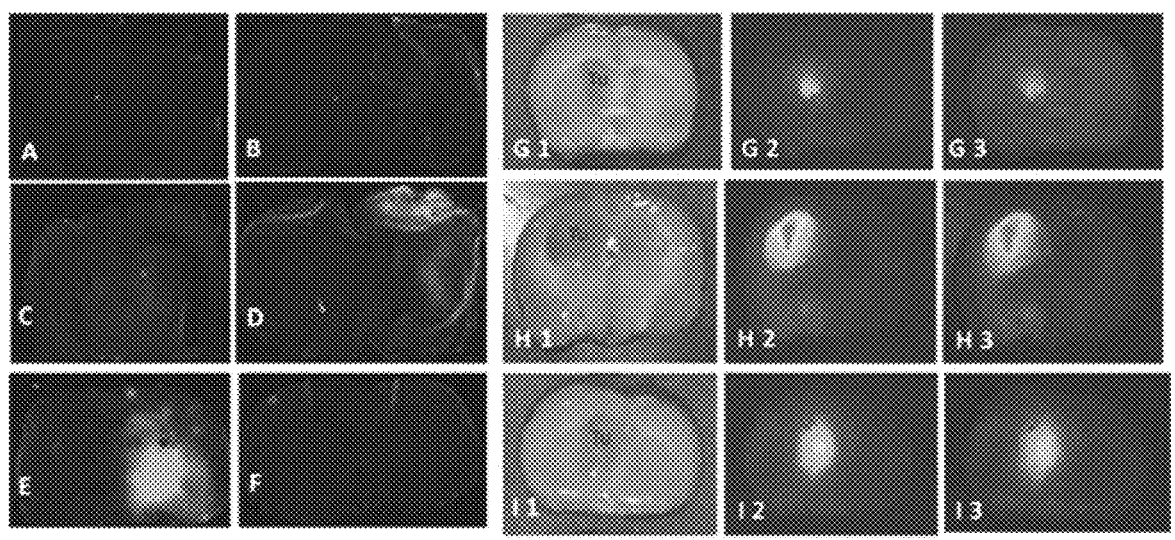
FIG. 17 depicts provides visual assessment of uptake of FITC labeled R8 (A, B) and FITC-labeled TAT monomer (D-F) in healthy and C6 tumor bearing rats (G-I). Images of brain cross sections A-F were obtained by confocal microscopy. (A) Normal untreated brain tissue. (B) FA-IA delivery of R9. (C-E) IA-THC delivery of three doses of TAT-FITC, 0.25, 0.5 and 1 mg, respectively. (F) IV delivery of 0.5 mg of TAT where a diffuse uptake of TAT in and beyond the blood vessels was seen preferentially in the white matter. (G-I) Uptake of FITC-TAT by tumor bearing three C6 tumor bearing rats. (G1-I1) Gross brain sections showing tumor (Tu). (G2-I2) Fluorescence images (G3-I3) Superimposed images.

IA delivery of cell-penetrating peptides to the brain is feasible. As a proof of principle experiment to determine if CPPs can be effectively targeted to the brain we performed IA-TCH injections of FITC labeled R8 and fluorescein-labeled TAT monomer. Using confocal microscopy we show that this is indeed the case with both CPPs having detectable deposition preferentially to the hemisphere ipsilateral to carotid injection (FIG. 17). Semi-quantitative analysis indicates that the distribution of R8 is more discrete and predominantly within vessel walls while TAT has more diffuse deposition within the white matter. Thus, TAT-FITC was utilized in subsequent experiments as it appeared to penetrate the brain parenchyma more readily. Importantly, a dose dependent increase in TAT parenchymal deposition was observes over the dose range tested (0.25-1 mg) (FIG. 17).

Fluorescein labeled TAT is rapidly taken up by glioma cells. Having now shown that TAT can be effectively delivered in a hemisphere specific manner through IA-TCH we asked whether tumor specific uptake could also be achieved. Initial experiments assessed the delivery of TAT-FITC after IA-TCH injection in C6 glioma-bearing animals. Semi-quantitative fluorescence imaging suggests that deposition is preferentially targeted to the tumor mass in all animals that were tested (N=3) (FIG. 17 G-H).

Figure 18A:
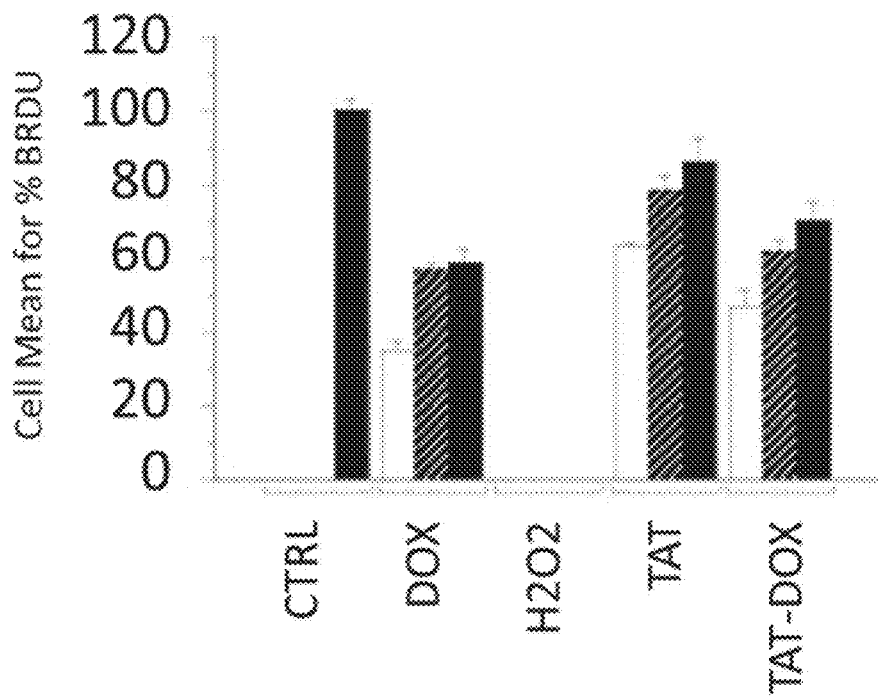
FIG. 18A depicts a chart of the results of a BrdU assay for 9L cells after exposure to TAT-conjugated doxorubicin.
Figure 18B:
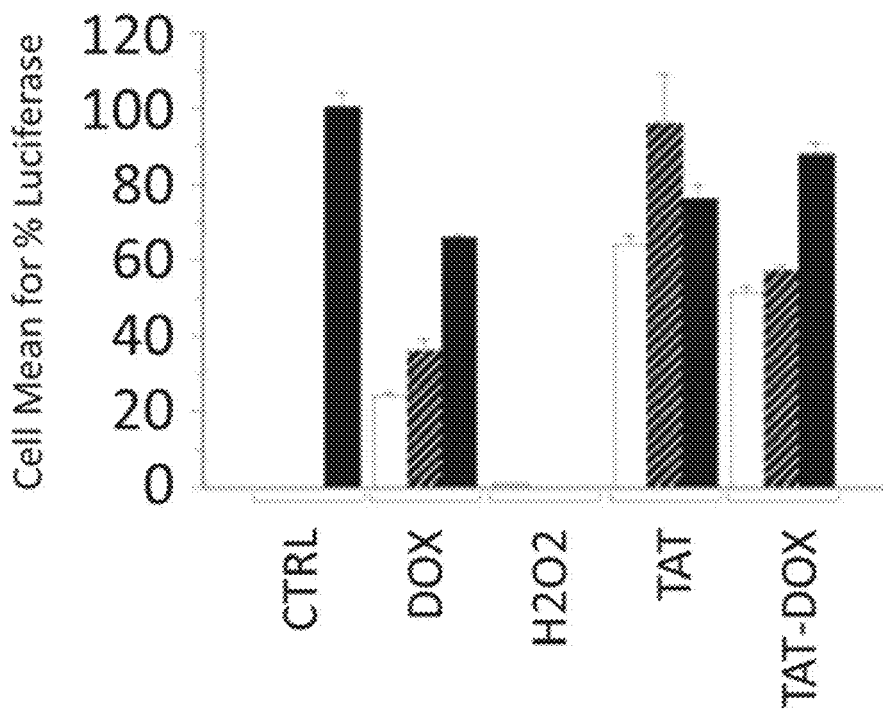
FIG. 18B depicts a chart of the results of a bioluminescence assay for 9L cells after exposure to TAT-conjugated doxorubicin.
Figure 19A:
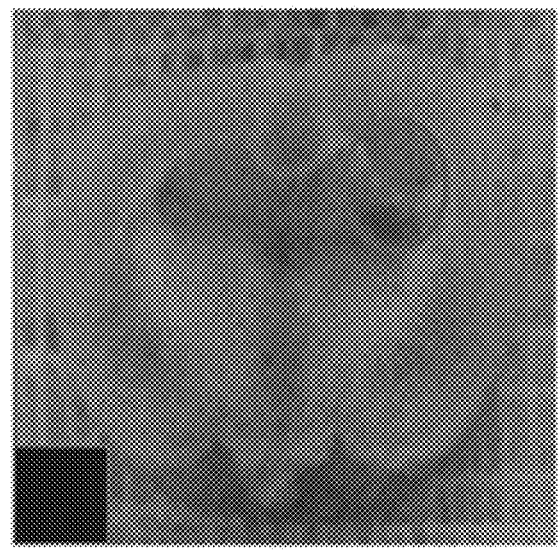
FIG. 19A depicts a gross brain section showing a tumor (circled).
Figure 19B:
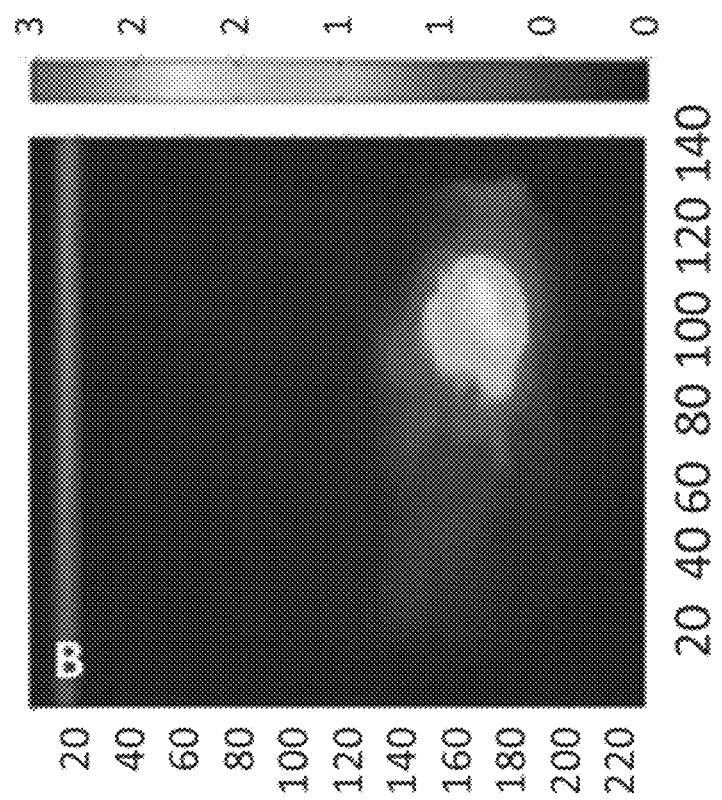
FIG. 19B shows fluorescence imaging of a tumor section of the tumor shown in FIG. 19A with uptake of FITC-labeled TAT-monomer.
Figure 19C:
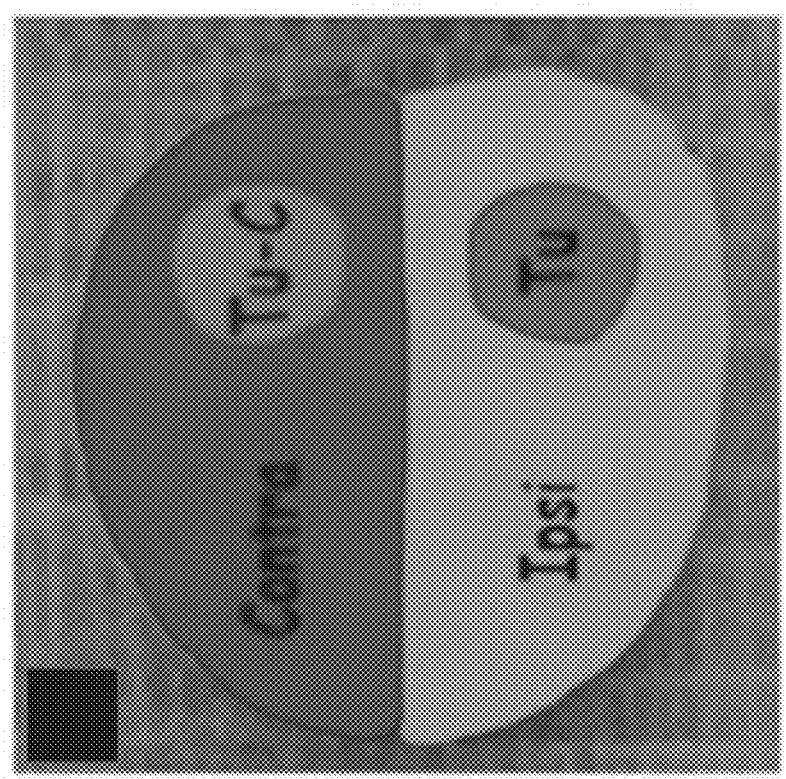
FIG. 19C depicts a schematic brain section corresponding to the rat brain shown in FIG. 19A which includes the tumor region (Tu), ipsilateral brain tissue (ipsi), region in the contralateral hemisphere corresponding to the tumor (Tu-C), remaining contralateral brain tissue and tissue (Contra) and background.
Figure 19D:
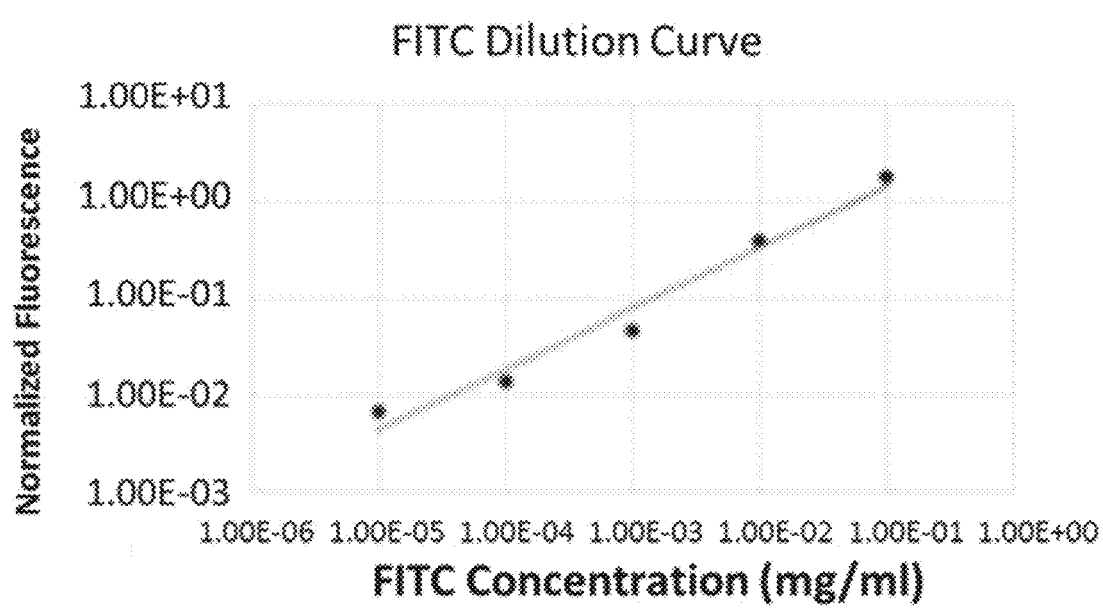
FIG. 19D depicts a linear correlation was between dissolved and measured FITC concentrations by fluorescence.
Figure 19E:
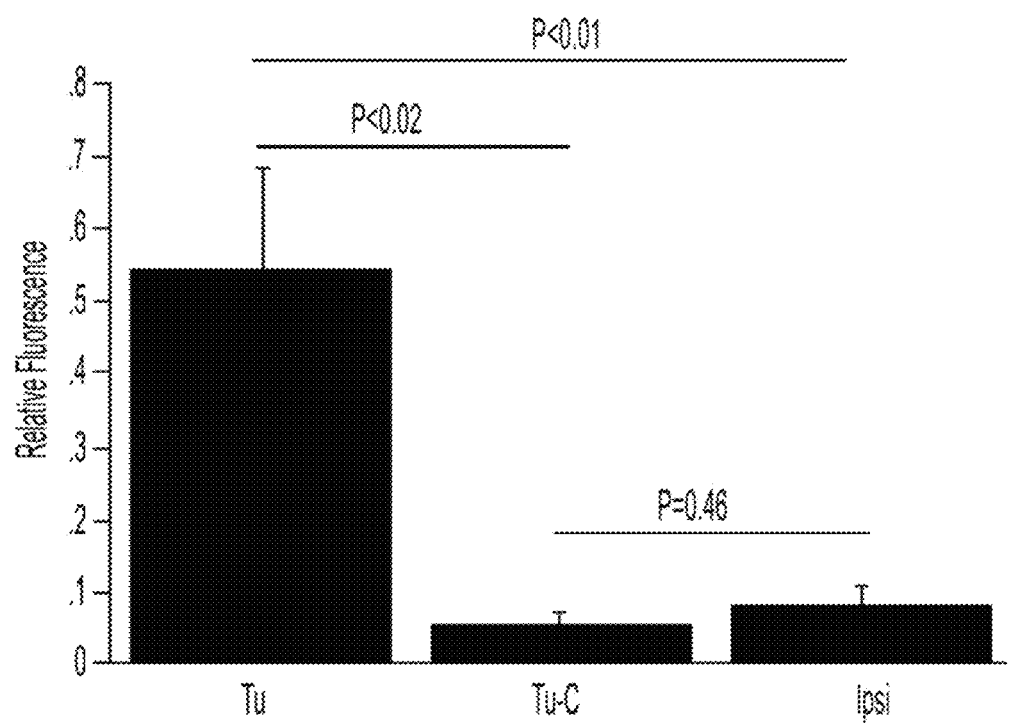
FIG. 19E depicts a chart of measurements for six animals showing 10.5× greater fluorescence in the tumor as compared to the tumor site on the contralateral hemisphere and 7.4× greater when compared to the ipsilateral non-tumor regions after treatment of FITC-labeled TAT monomer.
Figure 19F:
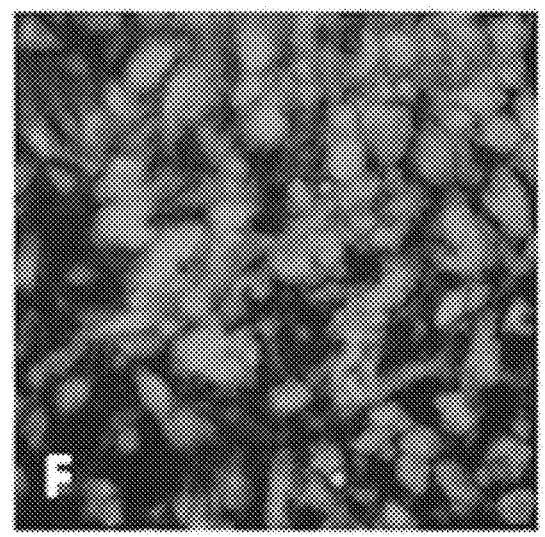
FIG. 19F depicts uptake of FITC-TAT by glioma cells under confocal microscopy.

TAT-conjugated doxorubicin retains cytotoxic properties in vitro. To gain insight into the ability of TAT-conjugated doxorubicin (TAT-Dox) to kill 9L glioma cells we performed a series of in vitro cytotoxicity experiments. In culture we assessed cellular viability as judged by BrdU and bioluminescence assays. Glioma cell cultures were exposed to increasing concentrations of Dox, TAT, and TAT-Dox. Increasing doses over the tested range (1-100 µM) were seen to increase the toxicity of each compound. The toxicity of TAT-Dox was intermediate between that of TAT (lowest toxicity) and Dox (highest toxicity), FIGS. 18A-18B.

Quantitative Assessment of Tumor TAT-FITC uptake by 9L glioma cell lines. Quantitative assessment of TAT-FITC tumor specificity was then investigated by imaging 9L-glioma bearing rats with a high sensitivity electron multiplying charge-coupled device. Animals received again underwent standard IA-TCH injection of TAT-FITC (N=8). When corrections were made for background fluorescence using the contralateral hemisphere, the tumor uptake compared to the ipsilateral cerebral hemisphere on the side of drug infusion was increased by 7.7-fold. In comparison to the corresponding contralateral region, the tumor had 11.7-fold greater TAT deposition (FIGS. 19A-19F).

Figure 20:
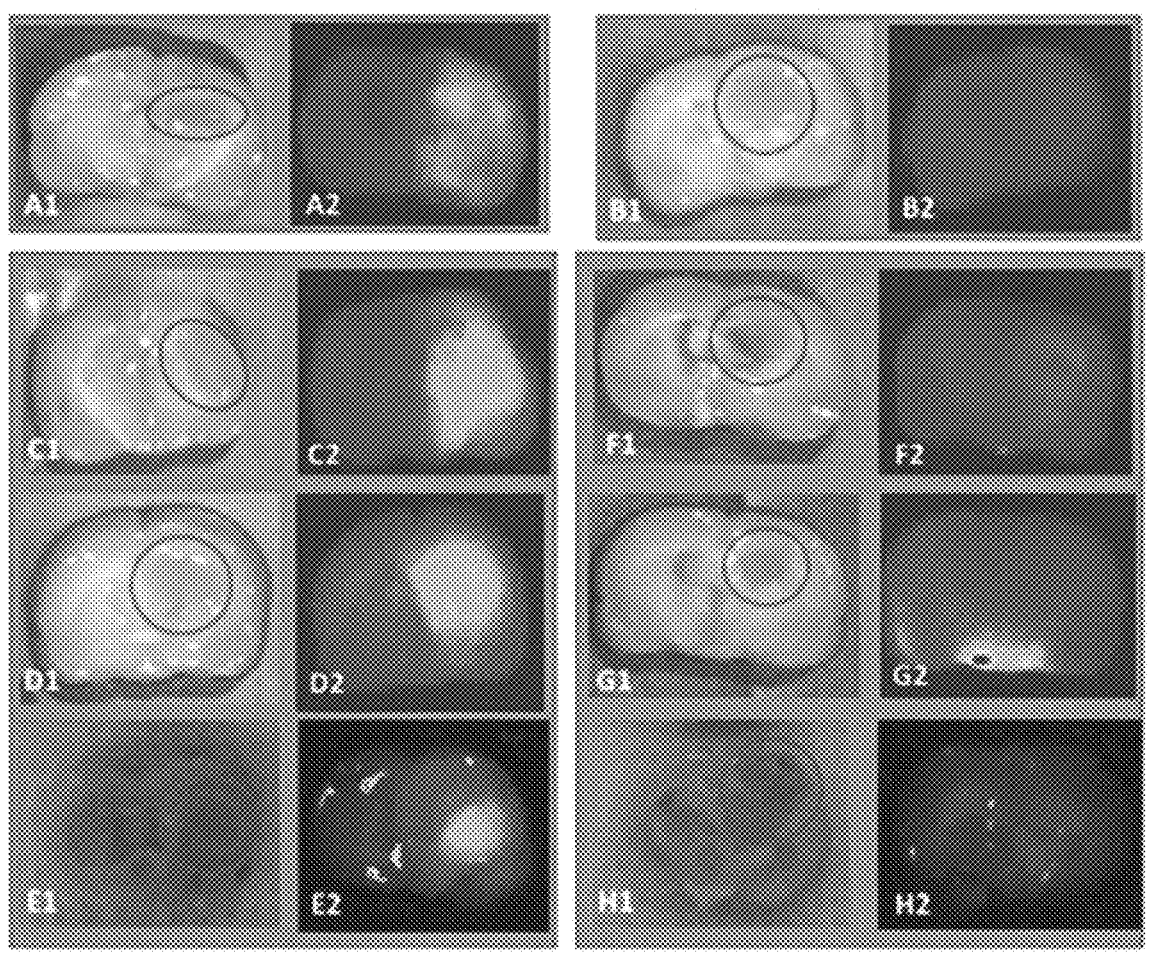
FIG. 20 provides a visual assessment of tumor selective uptake of TAT-Dox. A1 and A2 show gross and fluorescence images of intraarterial deliver of TAT-Dox. B1 and B2 show intravenous delivery of TAT-Dox. C1 to E1 and C2 to E2 show IA-TCH delivery of TAT Dox. F1 to H1 and F2 to H2 show FA-IA delivery of molar equivalent unconjugated Dox.

TAT enhances the effectiveness doxorubicin tumor delivery. To investigate whether TAT facilitates doxorubicin targeting to brain tumors, we conducted in vivo experiments in comparing the IA-TCH delivery of TAT versus TAT-Dox (N=8). Injection of TAT-Dox resulted preferential tumor uptake in all animals observed. This was seen to be much greater than the uptake of Dox alone (FIG. 20).

These series of experiments demonstrate the feasibility of selectively targeting gliomas using IA-TCH delivery of TAT-linked doxorubicin. The principles utilized are more generally applicable to other similar antineoplastic agents that do not effectively penetrate the blood-brain or blood-glioma barrier when delivered by conventional routes. The results show that dramatic improvements in drug delivery are possible using flow arrest methods in conjunction with TAT-conjugation. Both C-6 and 9-L glioma models demonstrated preferential tumor uptake, suggesting methodological robustness that may be applicable across other brain cancer cell lines as well as in human gliomas.

Example 5: Anesthesia Assisted Chemotherapy (ACT) of Brain Tumors

The profound effect of anesthetic drugs on cerebral blood flow (CBF) and metabolism can be used to improve IA drug delivery. Intravenous and volatile anesthetics have significantly different effects particularly on cerebral blood flow. We have observed HIV derived cell penetrating peptide, trans-activator of transcription, TAT, to be an effective carrier for drug intraarterial (IA) delivery when injected during transient cerebral hypoperfusion (TCH). We were therefore interested in assessing whether the choice of the anesthetic agent affected tumor specific delivery of TAT.

Experiments were conducted on anesthetized 9L tumor bearing rats. During the experiments brain/skin blood flow, pulse pleth/oximetery, EKG, inspired/expired gas composition and EEG were monitored. Background anesthesia with isoflurane was compared with IV propofol infusion at 100 mg/kg/hr. These doses were needed to produce EEG silence in rats. Fluorescein labeled TAT (0.5 mg) was injected during transient cerebral hypoperfusion achieved by injection of adenosine esmolol and a bolus of cold saline. The animals were euthanized 15 min later and brain tissue was harvested for fluorescent imaging. Each image was normalized to the background and the injected concentration.

Figure 21A:
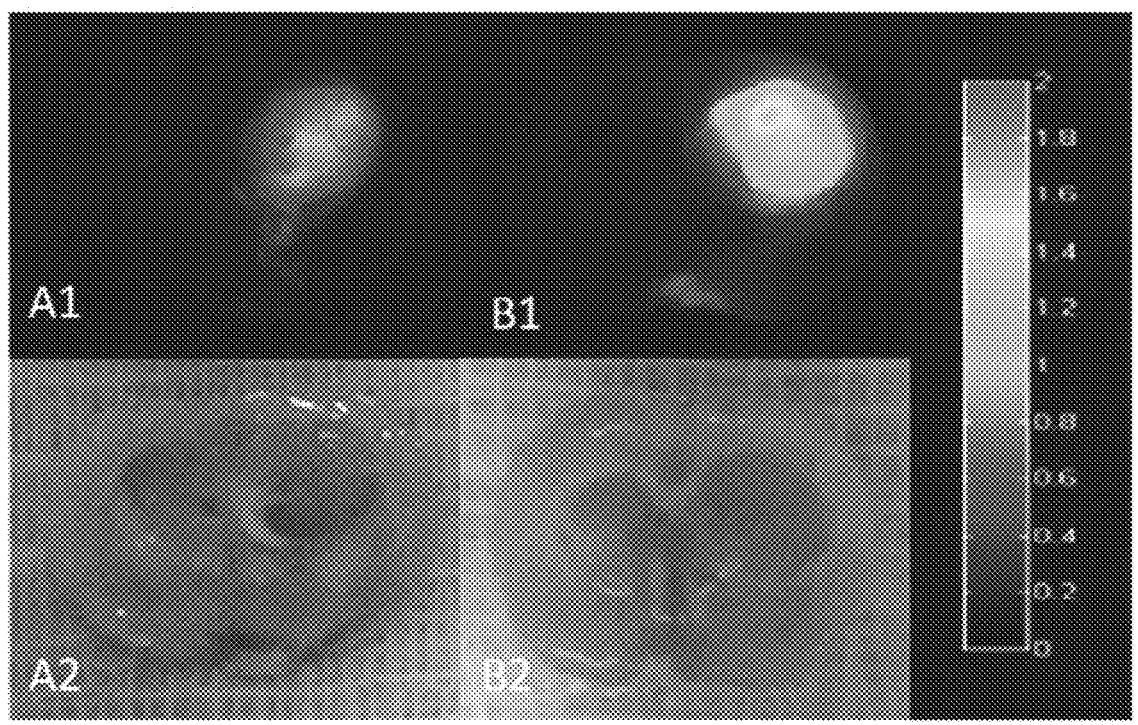
FIG. 21A provides a quantitative and visual assessment of the effect of anesthesia on intraarterial delivery of fluorescein labeled TAT (FITC-TAT). A1 and A2 show deep isoflurane anesthesia and B1 and B2 show deep propofol anesthesia, both of which are sufficient to produce EEG silence. Uptake of FITC-TAT was greater with propofol anesthesia.
Figure 21B:
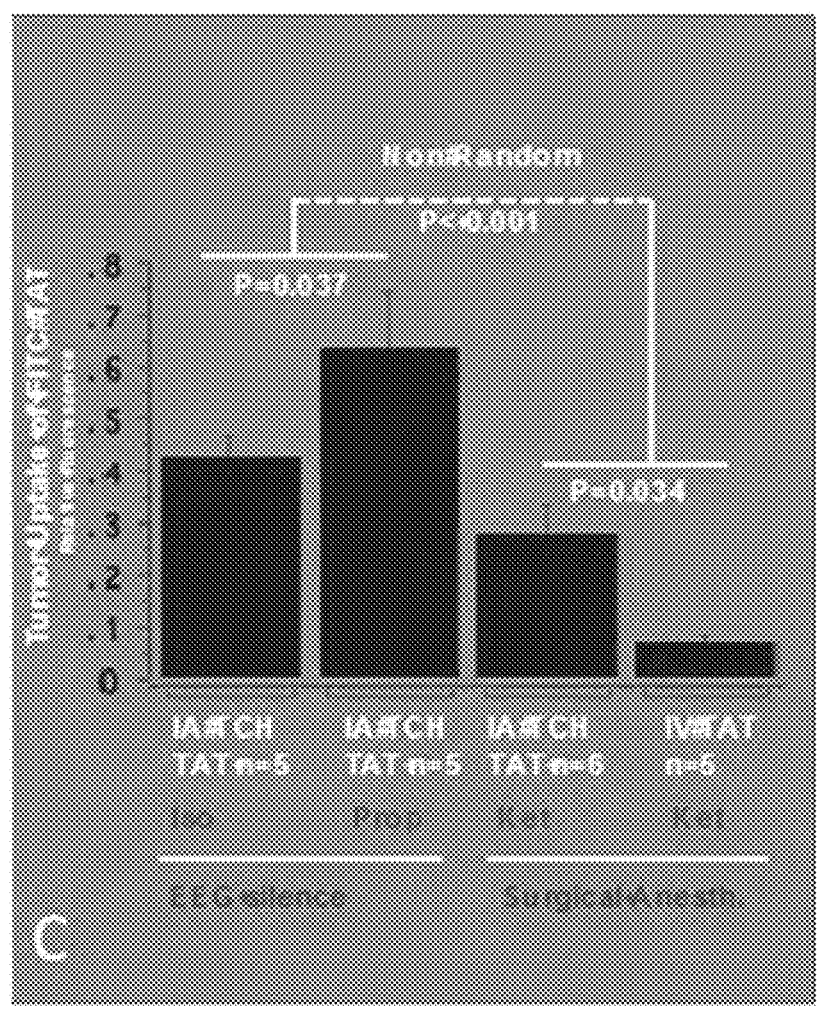
FIG. 21B provides a quantitative assessment of the effect of anesthesia on intraarterial delivery of fluorescein labeled TAT (FITC-TAT). Uptake of FITC-TAT in two groups of animals under EEG silence vs. surgical anesthesia. EEG silence was superior to the lighter level of surgical anesthesia. A greater uptake of TAT-FITC was seen with deep anesthesia with propofol which was superior to isoflurane anesthesia.

Representative data from this ongoing study is shown in FIGS. 21A-21B. A greater tumor concentration was achieved under deep propofol anesthesia compared to deep isoflurane anesthesia. Hemodynamic parameters recovered earlier during propofol anesthesia compared to isoflurane anesthesia. Yet there was a significantly greater uptake of TAT during deep propofol anesthesia compared to isoflurane anesthesia. When TAT uptake was compared with an earlier group of animals in which FITC-TAT monomer was injected intraarterially IA-TCH or IV TCH, deeper levels of anesthesia improved TAT uptake compared to surgical anesthesia.

The experiment shows that the choice and depth of anesthesia may have a profound effect on IA FITC-TAT delivery. Without being bound to theory, these improvements could be due to the regional hemodynamic effects of anesthetics and/or because of direct effects on tumor cell membranes. In follow-up cell culture studies, we are investigating the effects of anesthetic on tumor uptake of TAT and if there are any effects on membrane fluidity. Anesthetic drug selection and techniques may play a significant role in improving IA chemotherapy.

Example 6: TAT Monomer Animal Studies

By attaching TAT (monomer or oligomer) to a dye (such as Cy5) with light absorption properties different from hemoglobin, the delivery of TAT to brain tumors can be tracked in a sub second time frame. TAT monomer was conjugated to Cy5 by a commercial supplier. Three rats with 9L glioma implants were used. The skull over the site of measurement (tumor, tumor brain edge or healthy brain) is thinned and a fiberoptic probe connected to a diffuse reflectance spectroscopy (DRS) device is placed into the site. The probe carries white light to the brain and collects the tissue backscattered light to a spectroscope. The spectral changes from baseline (e.g. red versus black) in the tissue can be rapidly analyzed to assess tissue TAT concentrations. Similar probes can be put on the skin to assess TAT delivery in that location. This technique enables rapid sub-second assessment of tissue TAT concentrations and over prolonged time periods that are necessary to assess carriers for IA-TCH delivery.

Figure 22A:
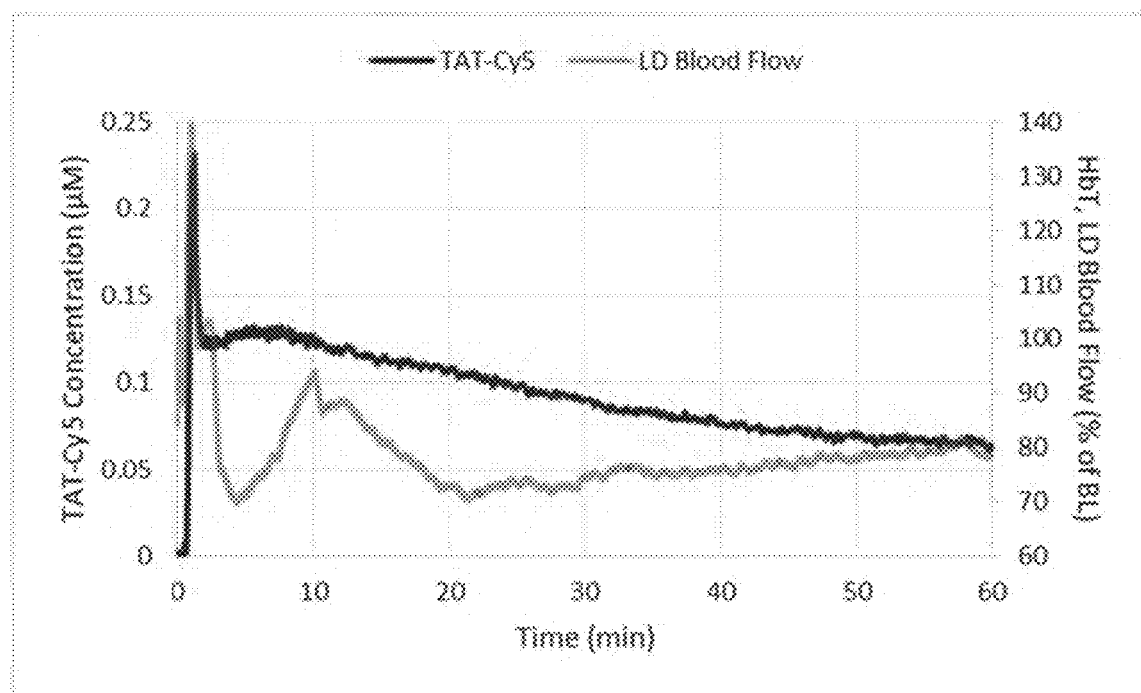
FIG. 22A depicts the concentration of Cy5-conjugated TAT monomer and blood flow over time (blue) in brain tumor after IA delivery without TCH. Blood flow changes are shown in red.
Figure 22B:
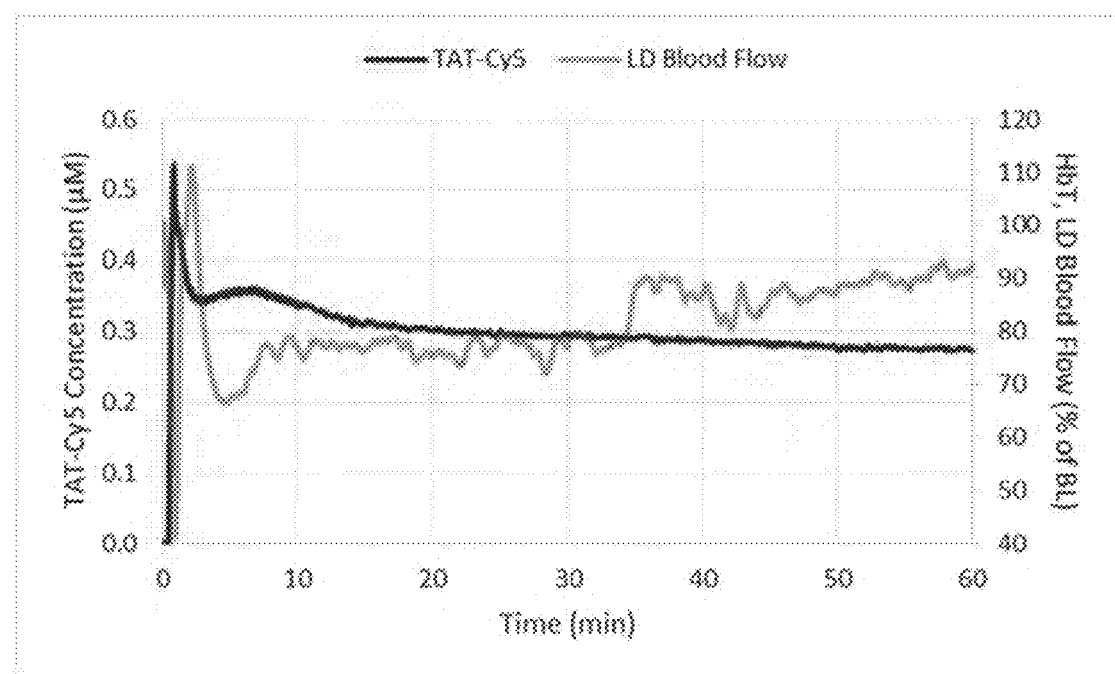
FIG. 22B depicts the concentration of Cy5-conjugated TAT monomer and blood flow over time (blue) in brain tumor after IA-TCH delivery. Blood flow changes are shown in red.
Figure 22C:
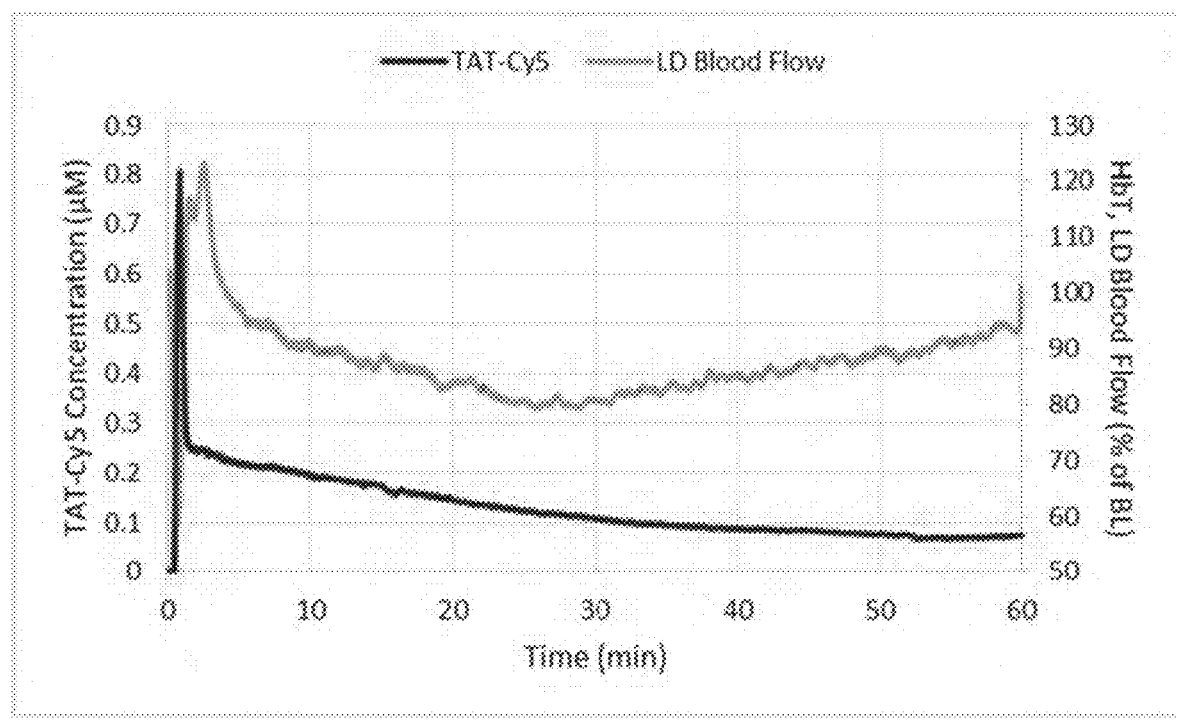
FIG. 22C depicts the concentration of Cy5-conjugated TAT monomer and blood flow over time (blue) in proximity to the tumor after IA-TCH delivery. Blood flow changes are shown in red.

Rats were placed under general anesthesia and their skulls were shaved to visualize the tumor beneath the bone. The skin on the lateral aspect of the thigh was also shaved. Two fiber optic probes each with afferent and efferent fibers as applied to the to the brain tumor, tumor edge and to skin respectively in the three animals. These fiber optic probe deliver white light (450-850 nm) and collect the tissue backscattered light. Change in spectrum of the returning light enables us to measure the concentration of the cy-5-TAT. With this method changes in tissue concentrations of cy-TAT can be determined in a sub-second time frame. Prior to use in animals we calibrated the device in a tissue phantom. Cy5-conjugated TAT monomer was injected via IA with or without TCH in rats with brain tumors and via IA-TCH in a rat with a normal brain. As shown in FIGS. 22A-22C, the injection with TCH in a rat with a brain tumor (FIG. 22B) achieved a higher concentration and greater retention of Cy5-conjugated TAT monomer compared to the injection without TCH (FIG. 22A) and to injection in a normal brain where the Cy5-conjugated TAT monomer was cleared rapidly from the brain (FIG. 22C). While TAT is cleared rapidly from normal rat brains, it is retained better in brain tumors where it was shown to be retained for over an hour which can be sufficient to yield cytotoxic effects. It can be seen that retention of the dye was greater in brain tumor tissue than in peri-tumor tissue.

Example 7: Melphalan-Conjugated TAT Cytotoxicity

Figure 23A:
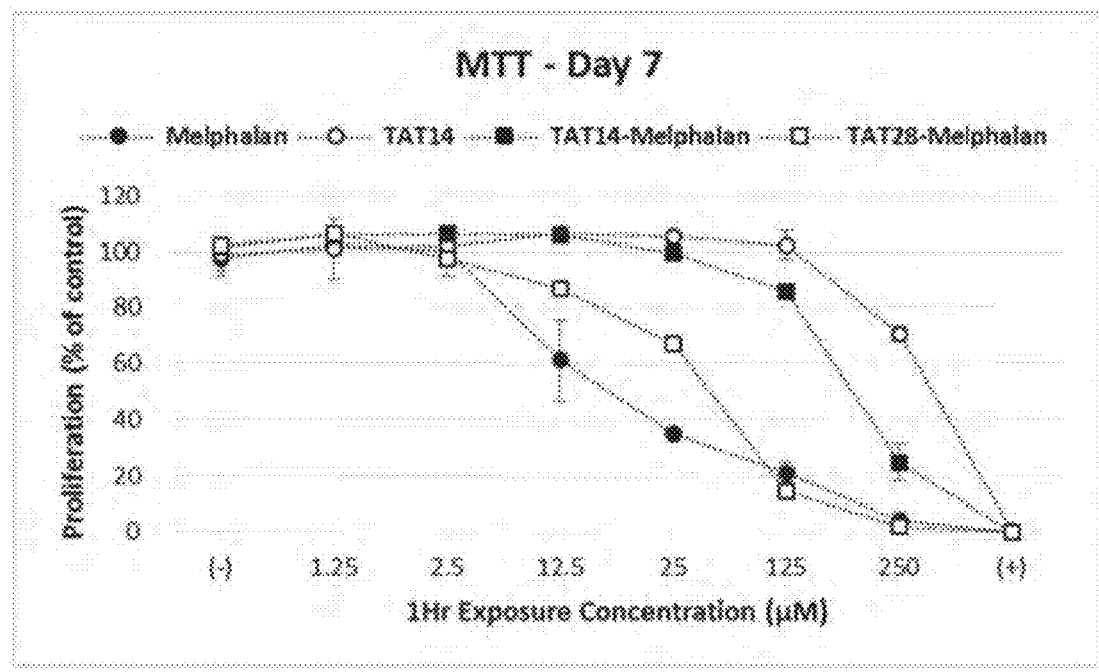
FIG. 23A depicts a chart of a MTT assay showing proliferation of cells versus transient exposure to different concentrations of melphalan, TAT alone, TAT monomer melphalan and TAT dimer melphalan.
Figure 23B:
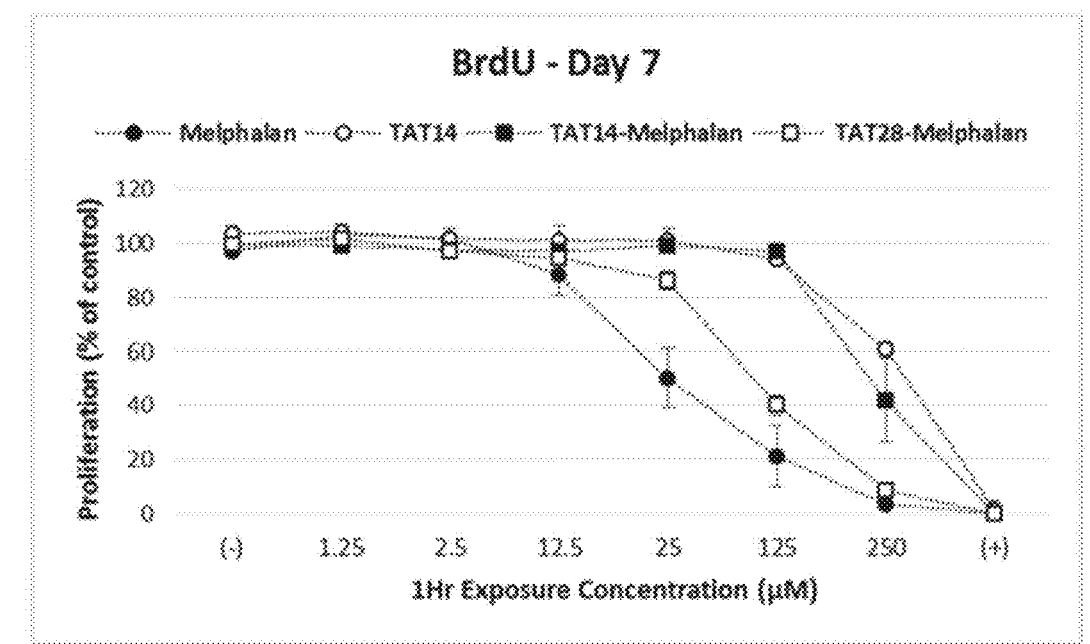
FIG. 23B depicts a chart of a BrdU assay showing proliferation of cells versus transient exposure to different concentrations of melphalan, TAT alone, TAT monomer melphalan and TAT dimer melphalan.
Figure 24A:
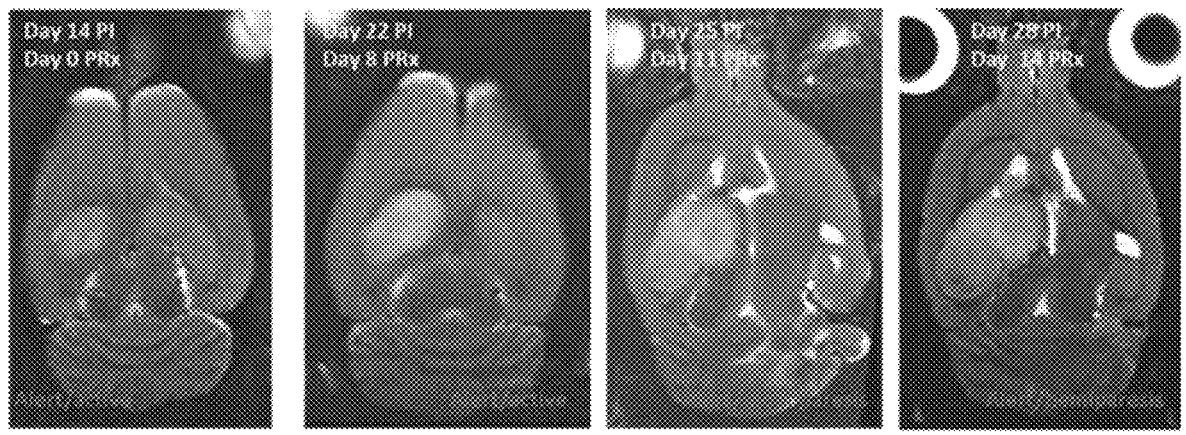
FIG. 24A shows serial MRI images of a control rat brain tumor progression.
Figure 24B:
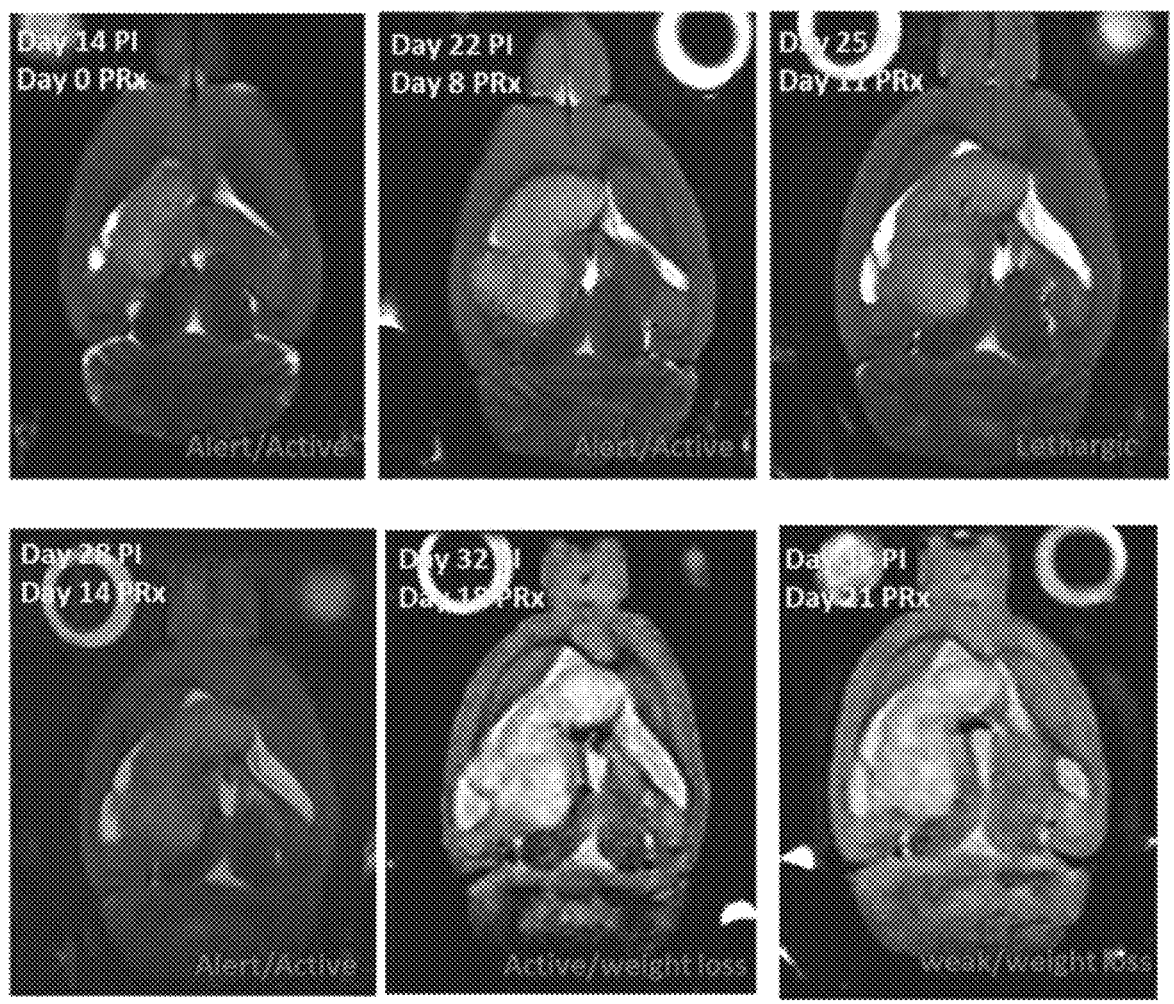
FIG. 24B shows serial MRI images of a rat brain after implantation of a 9L glioma tumor following IV TAT monomer melphalan treatment (Days 14-35).
Figure 24C:
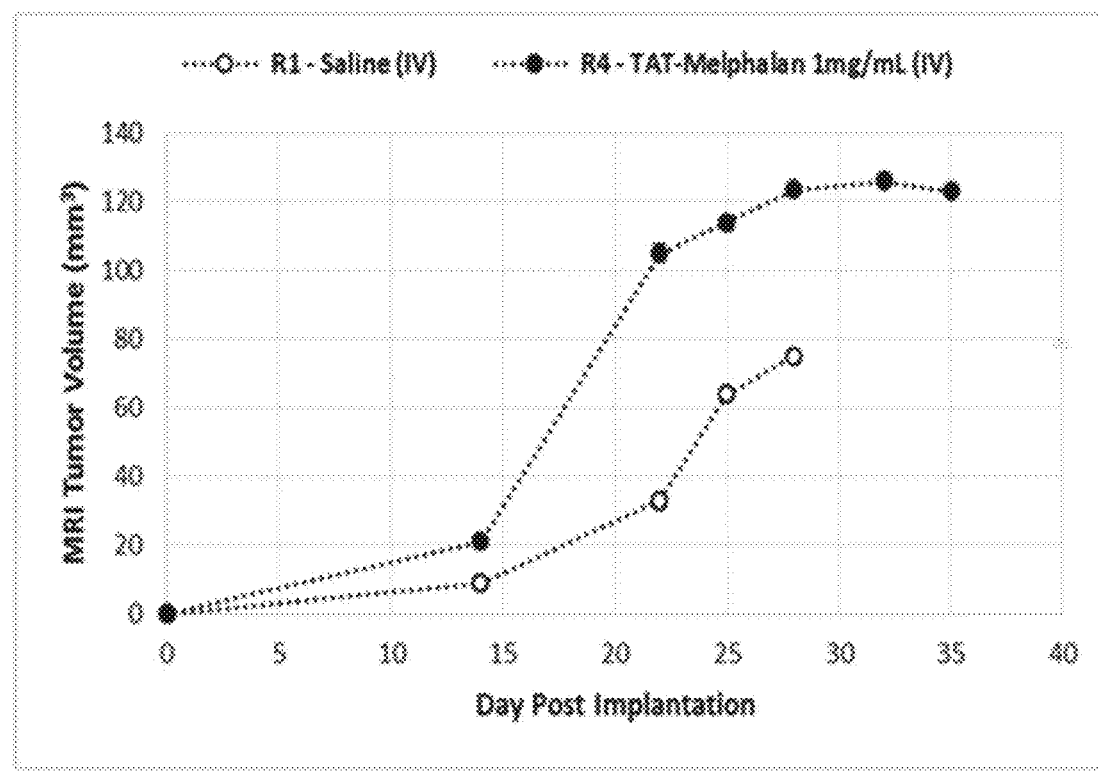
FIG. 24C depicts a chart of absolute MRI tumor volume versus days post-implantation for control and IV TAT monomer treated rats.
Figure 24D:
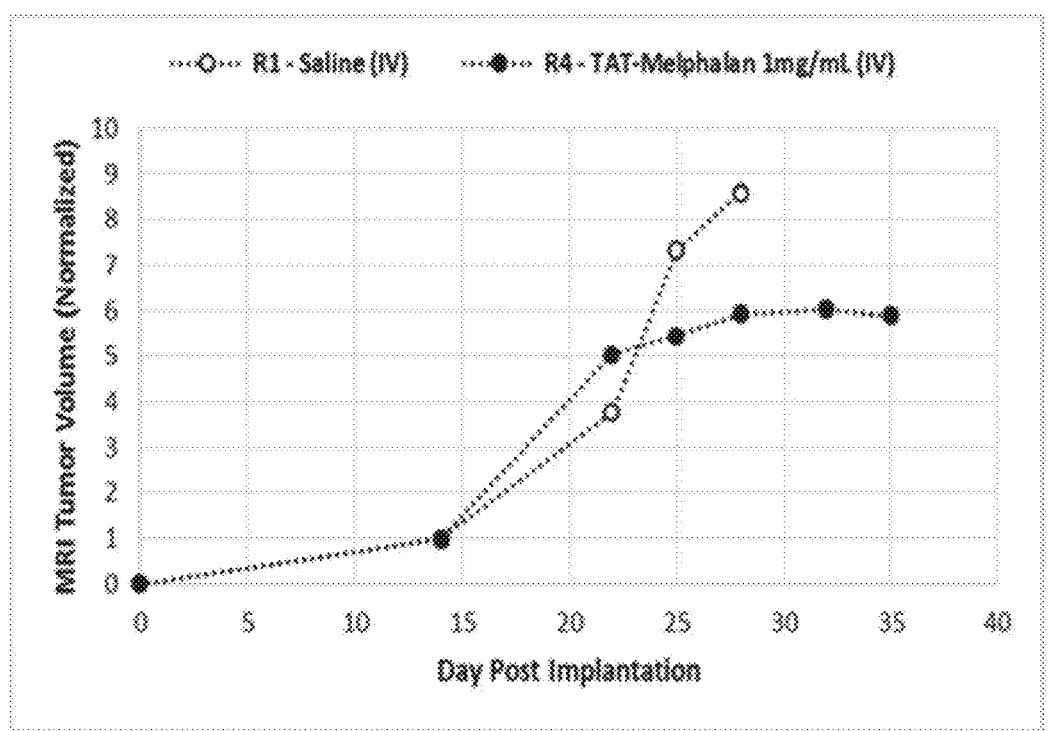
FIG. 24D depicts a chart of normalized MRI tumor volume versus days post-implantation for control and IV TAT monomer melphalan treated rats.

Cytotoxicity Study. 9L cells were grown to confluence in 96-well plates. Individual wells were exposed to no treatment or increasing concentrations of melphalan, TAT monomer, melphalan-conjugated TAT monomer (obtained from a supplier) or melphalan-conjugated TAT dimer (obtained from a supplier). Cells were incubated under these conditions for one hour. Growth factors were then reintroduced and the cells were grown for a week with standard periodic care. After 7 days, MTT and BrdU assays were used to assess cell viability. All tests were done in quadruplicate and data normalized to the untreated group. The assay results are shown in FIGS. 23A (MTT Assay) and 23B (BrdU Assay). As shown, conjugated of melphalan to either TAT monomer or TAT dimer resulted in attenuated cytotoxic activity of the drug but that cytotoxicity increases from TAT monomer to melphalan-conjugated TAT monomer to melphalan-conjugated TAT dimer to melphalan alone. IV injection of the In addition, 1 mg of melphalan-conjugated TAT dimer was administered to one tumor bearing rat and a saline control was administered to a control tumor bearing rat and serial MRI imaging was performed at days 14, 22, 25, 28, 32 and 35 days post-implantation (corresponding to 0, 8, 11, 14, 18 and 21 days post-injection). The MRI images are shown in FIGS. 24A (control) and 24B (tumor bearing rat brain). The control rat died at 29 days while the tumor bearing rat died at 35 days post-implantation. FIG. 24C shows the tumor volume as measured by MRI in both rats and FIG. 24D shows the normalized tumor volume by MRI.

Example 8: Single Versus Multiple Intra-Arterial Injections

Single Arrest Study. 9L glioma tumors were implanted into eight rats. 14 days post-implantation, the rats were anesthetized and prepared for the injections. Two delivery methods were used to deliver fluorescein-labeled TAT monomer: (1) traditional IV injection via the tail vein for 2 minutes; and (2) IA-TCH. Blood flow reduction was achieved by bolus IV injection of adenosine and esmolol that were flushed with cold saline. Animals were sacrificed 15 minutes after injection. Brain tissues were harvested and imaged using a multi-spectral imaging system using a photon counted cooled fluorescence camera. A 470 nm light was used for excitation while a 530 nm filter was used for imaging the emitted light. Brain tissues were also hematoxylin and eosin stained and imaged by confocal microscopy.

Multiple Arrest Study. 9L glioma tumors were implanted into five rats. 14 days post-implantation, the rats were anesthetized and prepared for the injections. Blood flow reduction was achieved by bolus IV injection of adenosine and esmolol that were flushed with cold saline. Four arrest cycles were used to deliver fluorescein-conjugated TAT monomer via intra-arterial injection with a 5 minute recovery period between each arrest. Animals were sacrificed 15 minutes after injection. Brain tissues were harvested an imaged using a multi-spectral imaging system using a photon counted cooled fluorescence camera. A 470 nm light was used for excitation while a 530 nm filter was used for imaging the emitted light. The single arrest cycle data was obtained from historical controls.

Figure 25A:
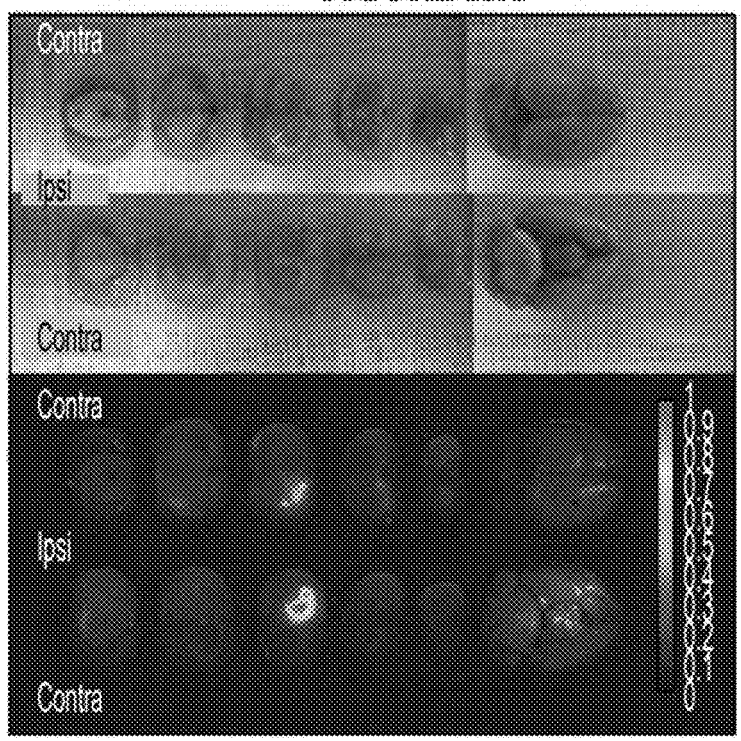
FIG. 25A depicts gross brain images and both multi-spectral imaging and hematoxylin and eosin stained brain sections for IA-TCH FITC-labeled TAT monomer treated rats.
Figure 25A:
Figure 25B:
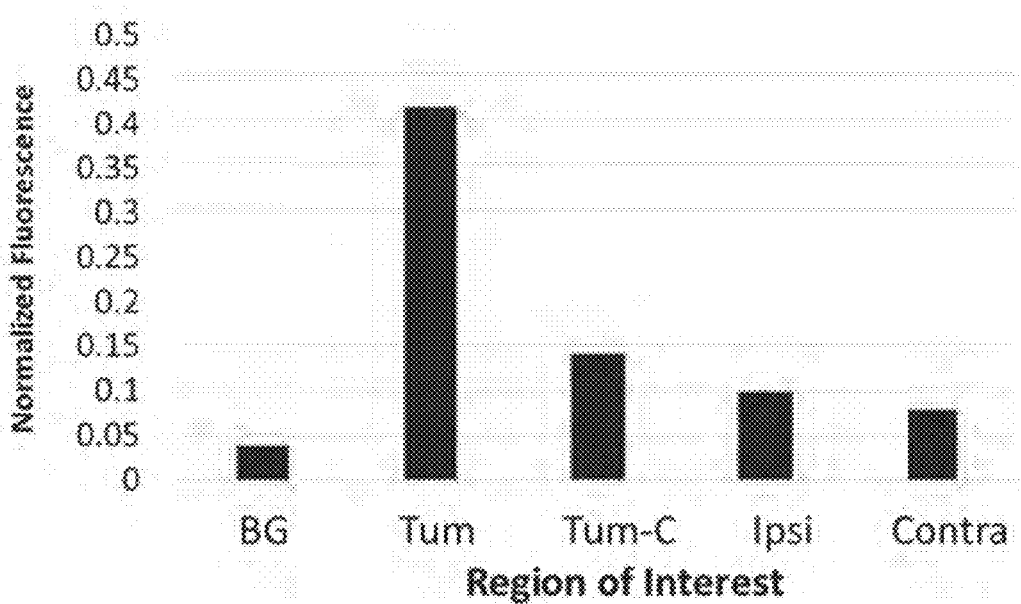
FIG. 25B depicts a chart showing normalized fluorescence by brain region for the IA-TCH treated rats shown in FIG. 25A.

FIG. 25A shows the brain tissue images for the contralateral hemisphere (left column) and ipsilateral brain tissue (second column) via normal imaging side-by-side with multi-spectral imaging and hematoxylin and eosin staining. FIG. 25B shows a chart of fluorescence in the background (BG), tumor (Tum), region in the contralateral hemisphere corresponding to the tumor (Tum-C), ipsilateral brain tissue (Ipsi) and remaining contralateral hemisphere (Contra).

Figure 25C:
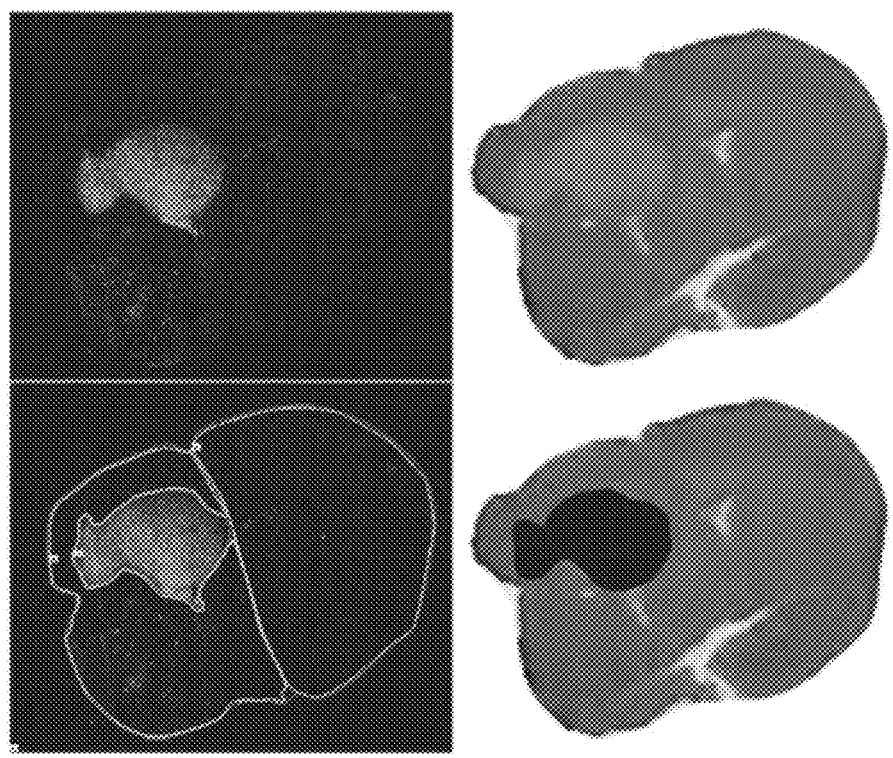
FIG. 25C depicts confocal microscopy and hematoxylin and eosin stained brain sections for IA-TCH FITC-labeled TAT monomer treated rats.
Figure 25D:
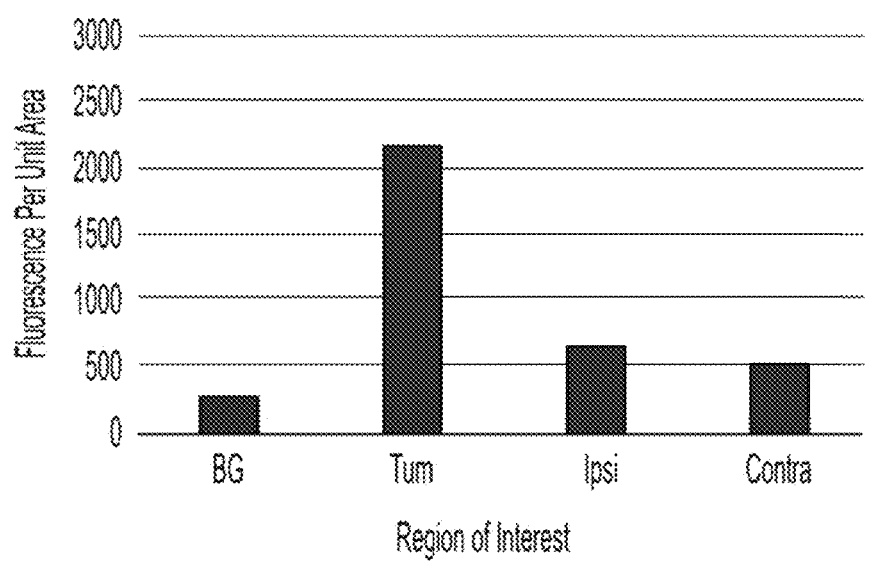
FIG. 25D depicts a chart of fluorescence by brain region for the rats shown in FIG. 25C.
Figure 26A:
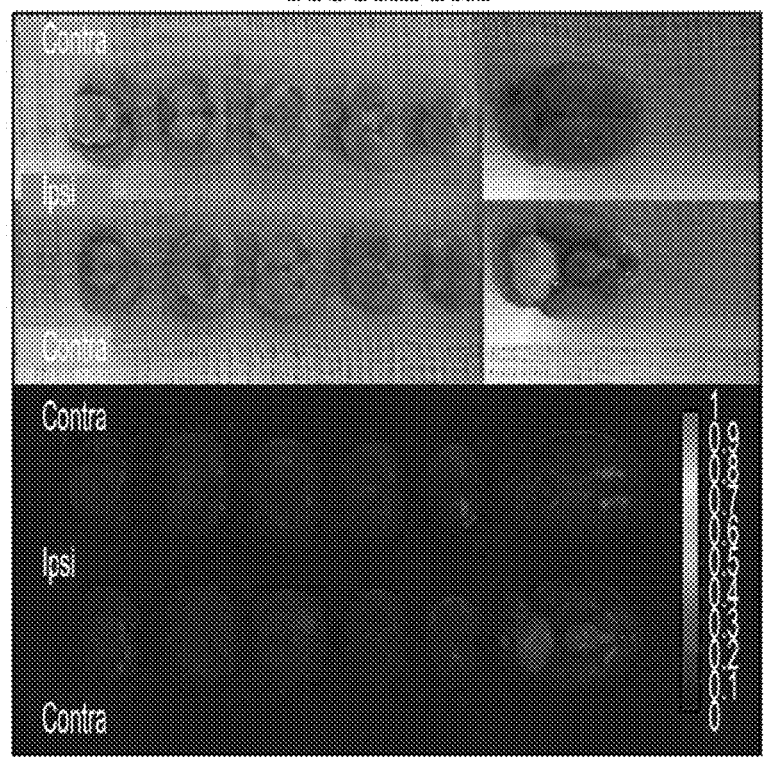
FIG. 26A shows images of control rat brains including gross brain images and both multi-spectral imaging and hematoxylin and eosin staining of corresponding brain sections for an IV FITC-labeled TAT monomer treated rat.
Figure 26A:
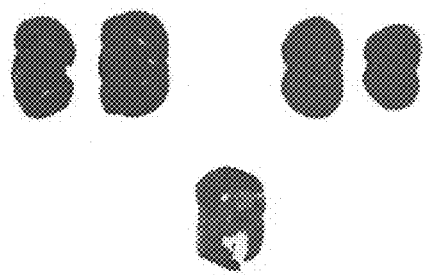
Figure 26B:
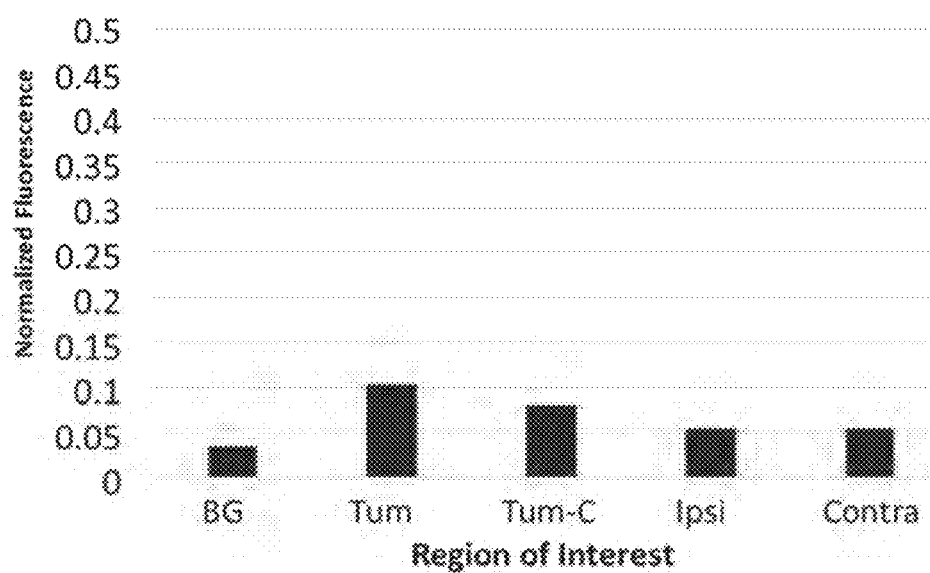
FIG. 26B shows normalized fluorescence by brain region for the IV TAT monomer treated rat shown in FIG. 26A.
Figure 26C:
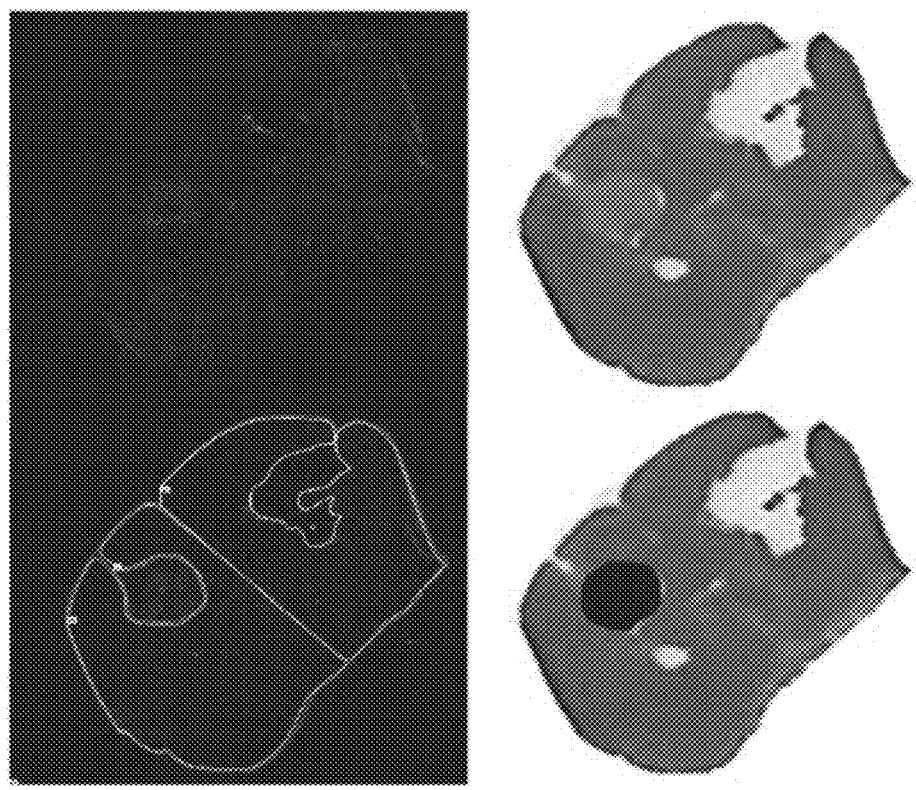
FIG. 26C depicts confocal microscopy and hematoxylin and eosin stained brain sections for an IV treated rat.
Figure 26D:
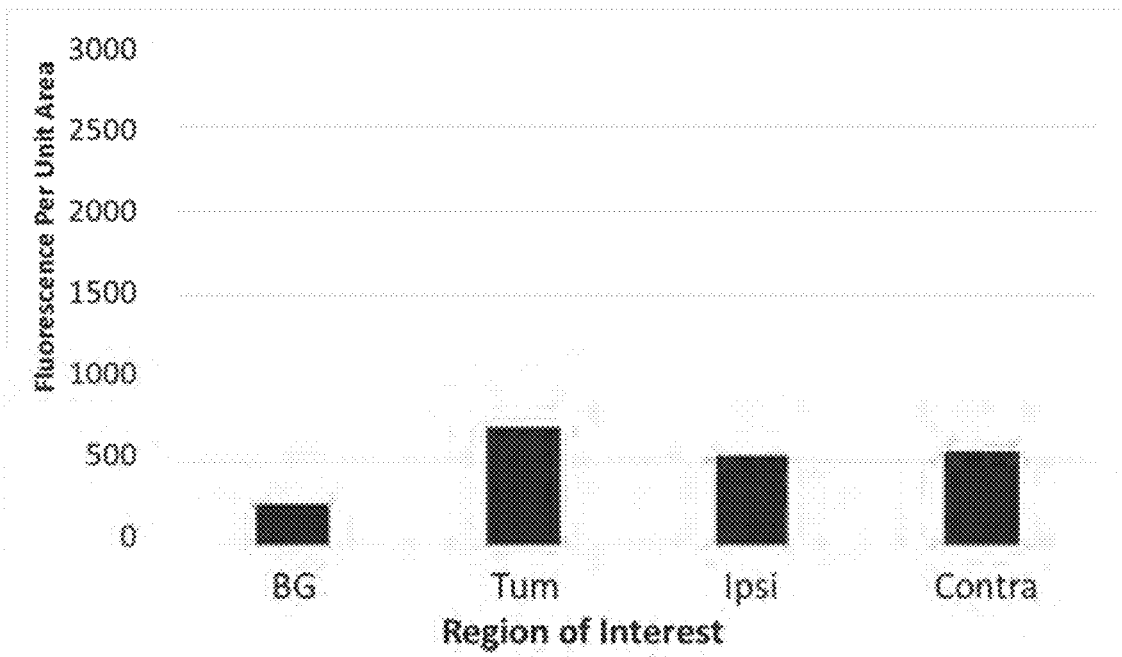
FIG. 26D depicts a chart of fluorescence by brain region for the rat shown in FIG. 26C.

FIG. 25C shows the brain tissue images under confocal microscopy for the contralateral hemisphere (top row) and tumor hemisphere (bottom row) side-by-side with the hematoxylin and eosin stained sections. FIG. 25D shows a chart of fluorescence in the background (BG), tumor (Tum), ipsilateral brain tissue (Ipsi) and the contralateral hemisphere (Contra).

FIGS. 26A-26D shows corresponding images and charts for the IV (control) rat brains.

Figure 27A:
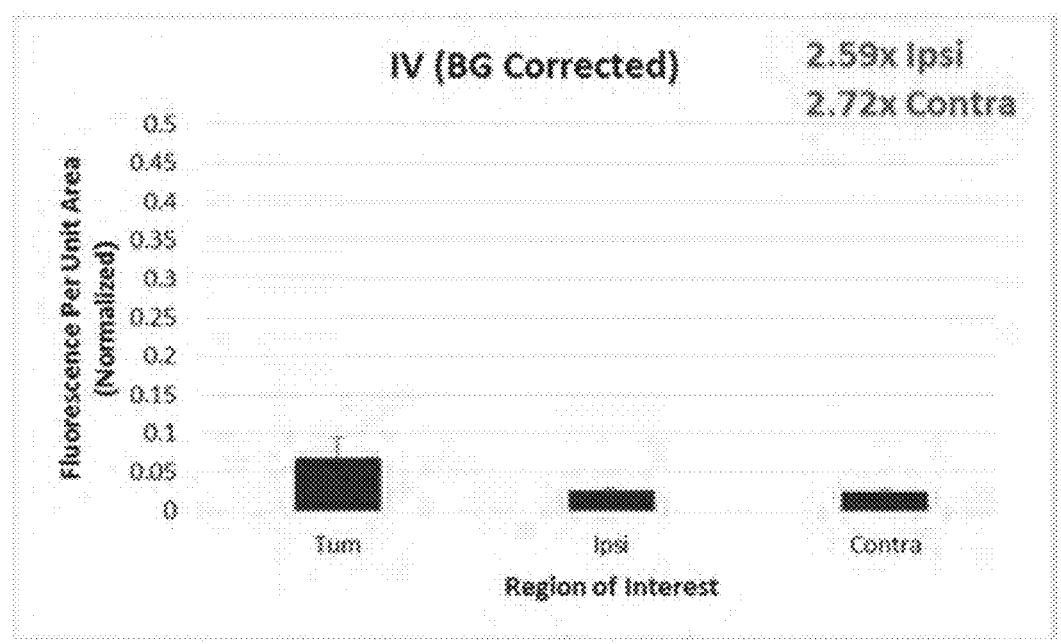
FIG. 27A depicts a chart of fluorescence by brain region for IV-treated rats using multi-spectral imaging.
Figure 27B:
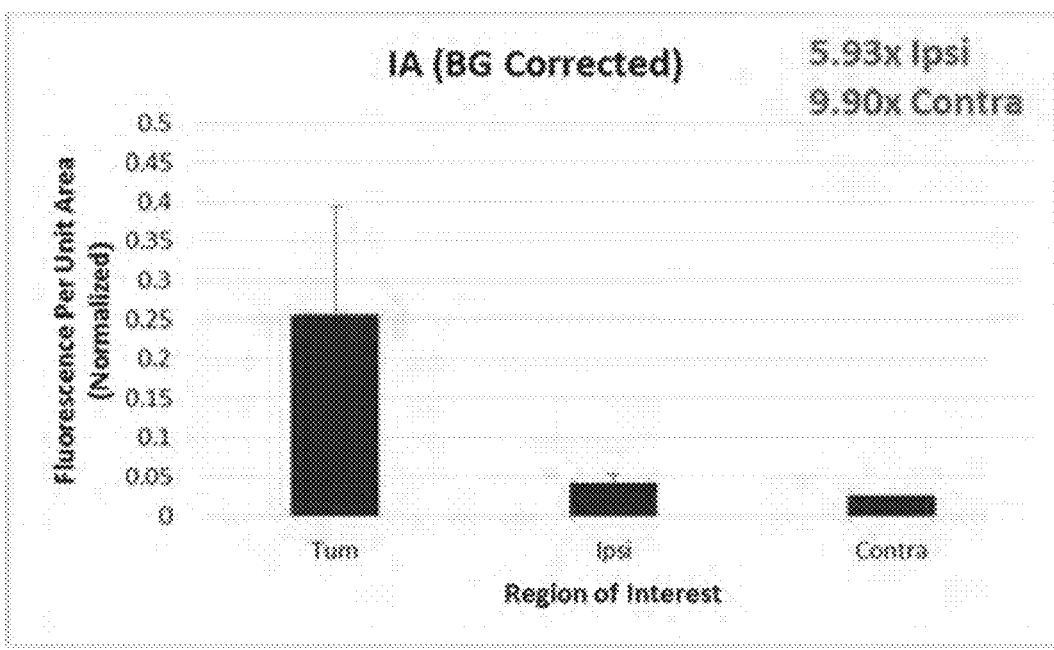
FIG. 27B depicts a chart of fluorescence by brain region for IA-TCH treated rats using multi-spectral imaging.
Figure 27C:
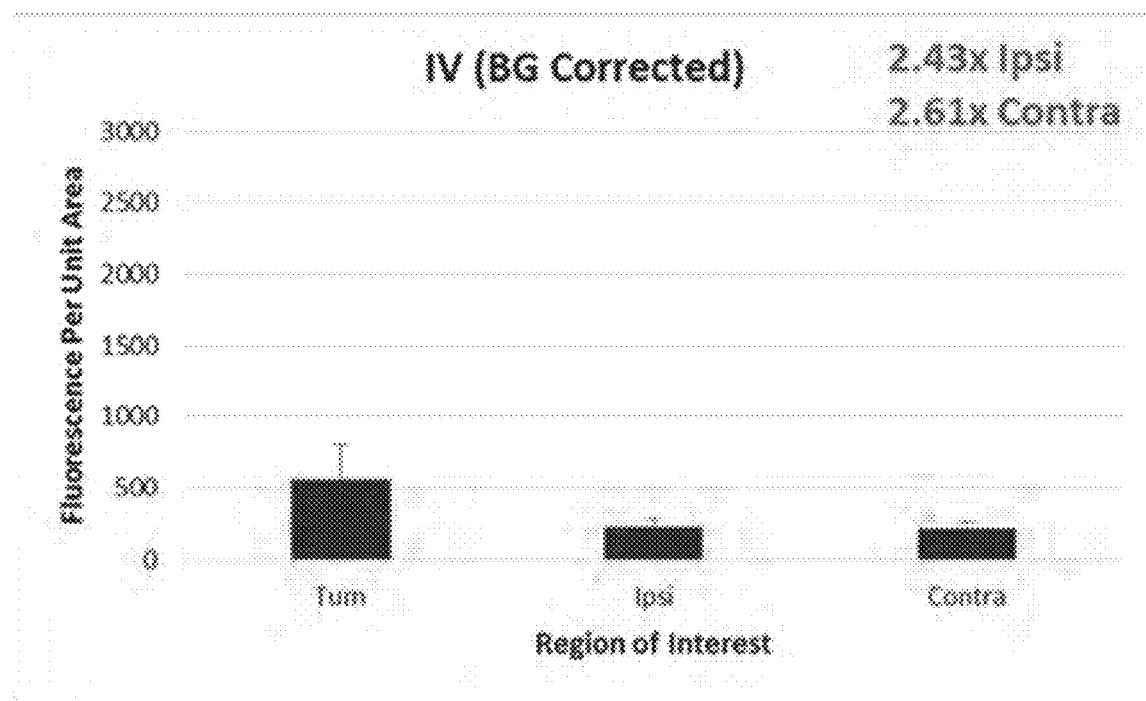
FIG. 27C depicts a chart of fluorescence by brain region for IV-treated rats using confocal microscopy.
Figure 27D:
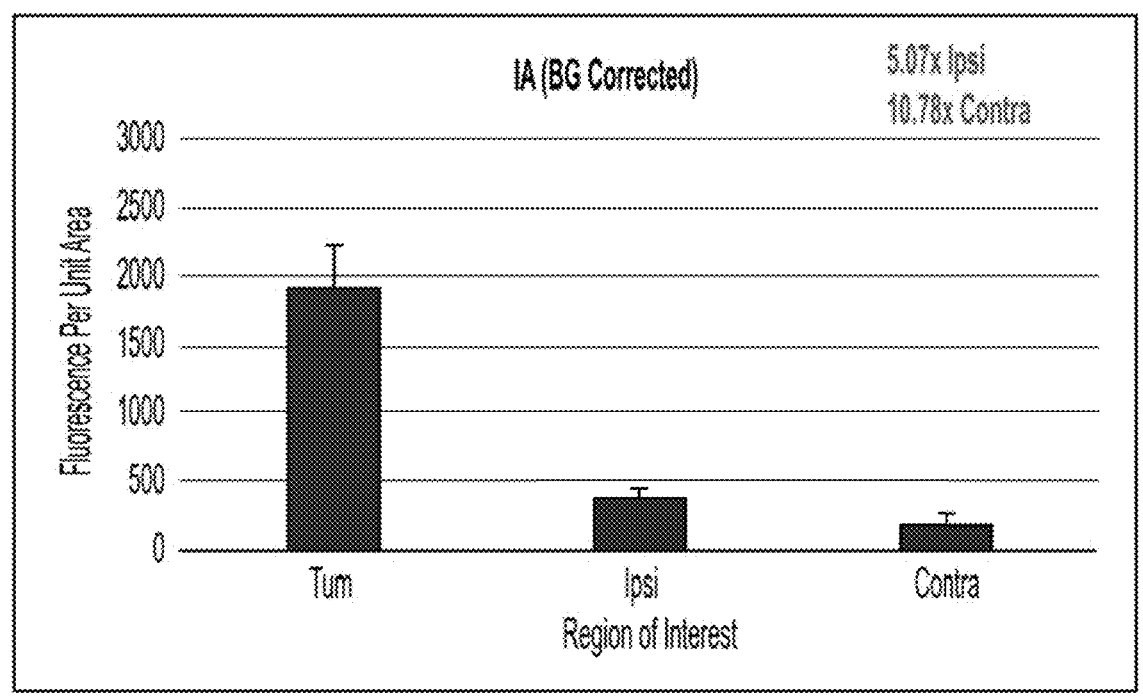
FIG. 27D depicts a chart of fluorescence by brain region for IA-TCI treated rats using confocal microscopy.

FIGS. 27A-27D show comparison charts of the background corrected fluorescence for the IV (FIGS. 27A and 27C) and IA-TCH (FIGS. 27B and 27D) methods for the tumor (Tum), ipsilateral brain tissue (Ipsi) and contralateral hemisphere (Contra) for multi-spectral imaging (FIGS. 27A and 27B) and confocal microscopy (FIGS. 27C and 27D). These data show fluorescence is 2.59× in the tumor versus the ipsilateral brain tissue and 2.72× versus the contralateral hemisphere for IV injection using multi-spectral imaging (FIG. 27A). Correspondingly for IA-TCH, the data show fluorescence is 5.93× in the tumor versus the ipsilateral brain tissue and 9.90× versus the contralateral hemisphere (FIG. 27B). These data show fluorescence is 2.43× in the tumor versus the ipsilateral brain tissue and 2.61× versus the contralateral hemisphere for IV injection using confocal microscopy (FIG. 27C). Correspondingly for IA-TCH, the data show fluorescence is 5.07× in the tumor versus the ipsilateral brain tissue and 10.78× versus the contralateral hemisphere (FIG. 27D). While both injection methods showed tumor-selective TAT uptake, the IA-TCH achieved a higher concentration of about four-fold greater than the IV method. IA-TCH shows 5-6× improved tumor selectivity versus 2× for IV injections.

Figure 28A:
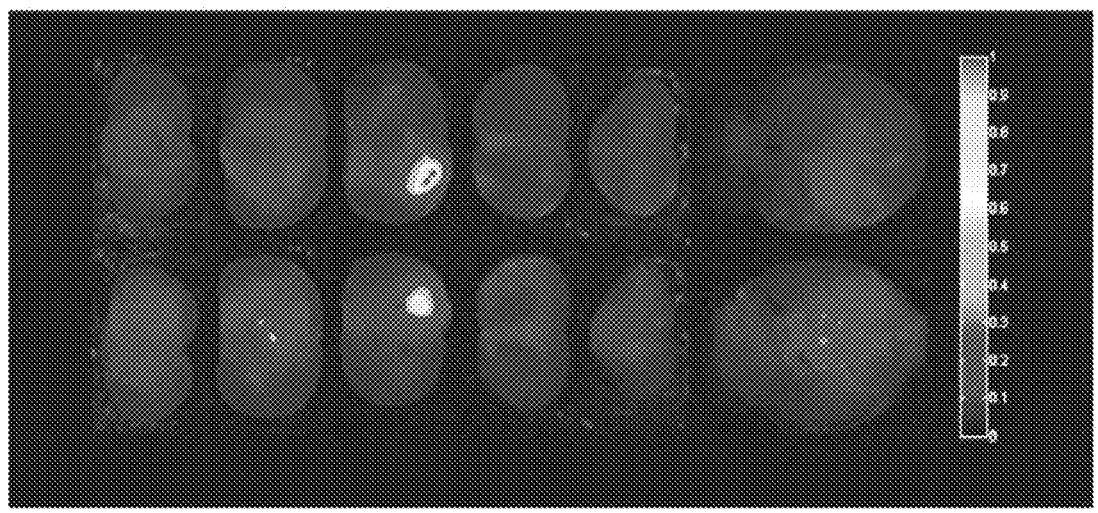
FIG. 28A depicts multi-spectral imaging of rat brains for IA-TCH with four arrest drug TAT delivery cycles.
Figure 28B:
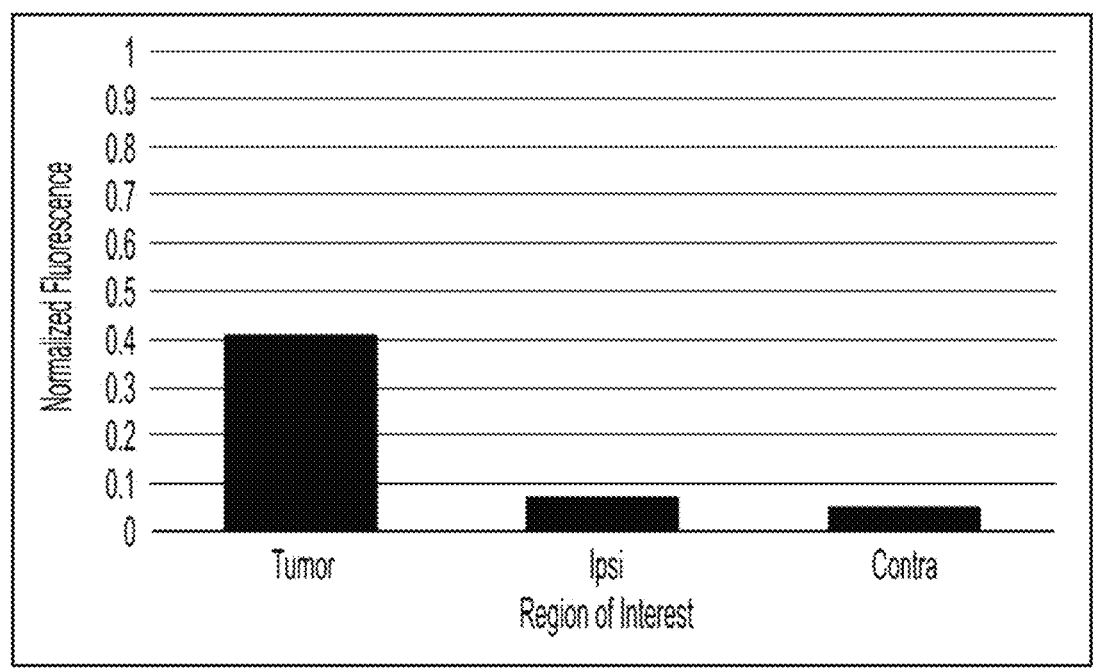
FIG. 28B depicts normalized fluorescence by brain region of the rats shown in FIG. 28A.

FIG. 28A shows multi-spectral imaging of the rat brains for IA-TCH with four arrests. FIG. 28B shows the normalized fluorescence by region of interest for these samples. FIG. 28C compares the normalized fluorescence for single arrest and 4× arrest IA-TCH by brain region. As shown, multiple arrest increases the amount of TAT deposition but also increases non-specific deposition as compared to single-arrest. Thus, smaller doses in multiple arrests may allow for the reduction of total dose.

Example 9: IA-TCH Delivery of Melphalan-Conjugated TAT

Thirteen 9L glioma-implanted anesthetized rats were intubated and ventilated. The carotid artery of each rat was exposed and cannulated but the ICA was not isolated to minimize surgical trauma. The rats were subjected to delivery of melphalan with adenosine, esmolol and cold saline via IA-TCH. Six rats received 0.25 mg of melphalan, three rats received 0.5 mg melphalan and one rat received 1 mg of melphalan. Remaining rats were either treated with saline or left untreated. After the IA-TCH injection, rats were allowed to recover and sacrificed when pre-determined criteria were met.

Figure 29A:
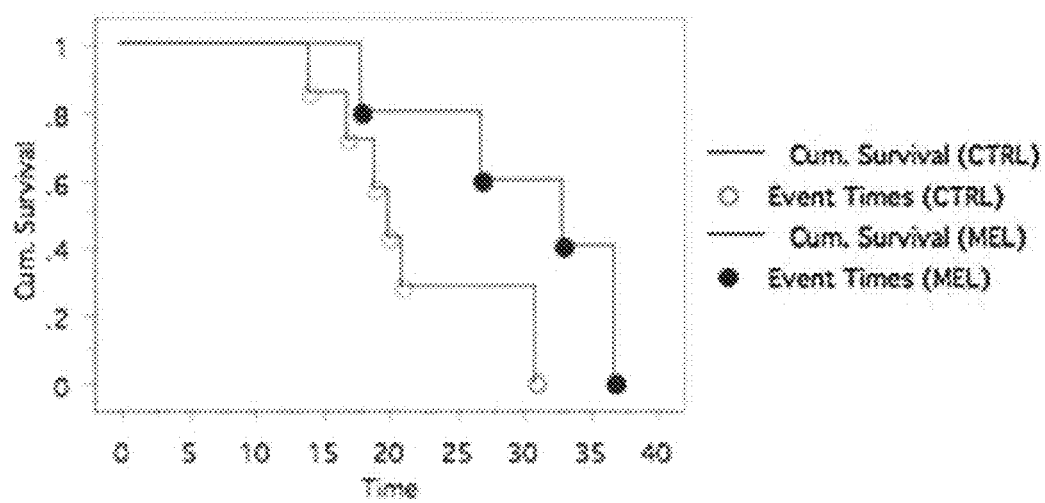
FIG. 29A depicts cumulative survival for control and melphalan treated groups.
Figure 29B:
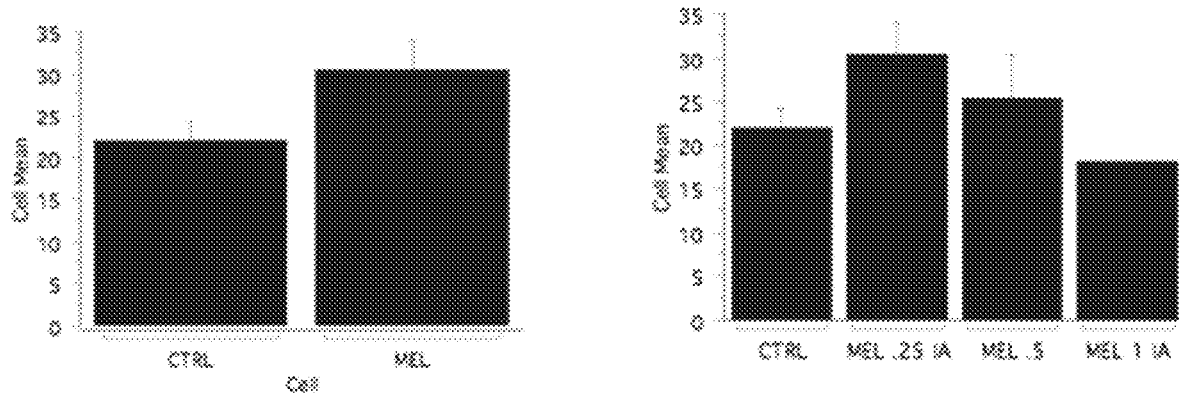
FIG. 29B depicts charts of survival for each treatment group.

During surgery, one rat suffered severe bleeding and was euthanized. Other rats suffered significant bleeding which was controlled with careful surgical hemostasis. As shown in FIG. 29A, peak survival was found in the 0.25 mg melphalan group. In a head-to-head comparison between the melphalan-treated rats and controls, there was a trend toward survival from 22+/−7 to 30+/−8 days (p=0.07) (FIG. 29B).

A similar procedure was performed on seven 9L glioma-implanted rats using melphalan-conjugated TAT monomer at a dose of 1 mg (0.16 mg melphalan content). However, the ICA was isolated with an aneurysm clip. Survival of the rats was monitored and images of the brains of the rats were obtained by MRI. The same procedure was performed using 5 rats with melphalan-conjugated TAT dimer at a dose of 1 mg (0.08 mg melphalan content).

Figure 30A:
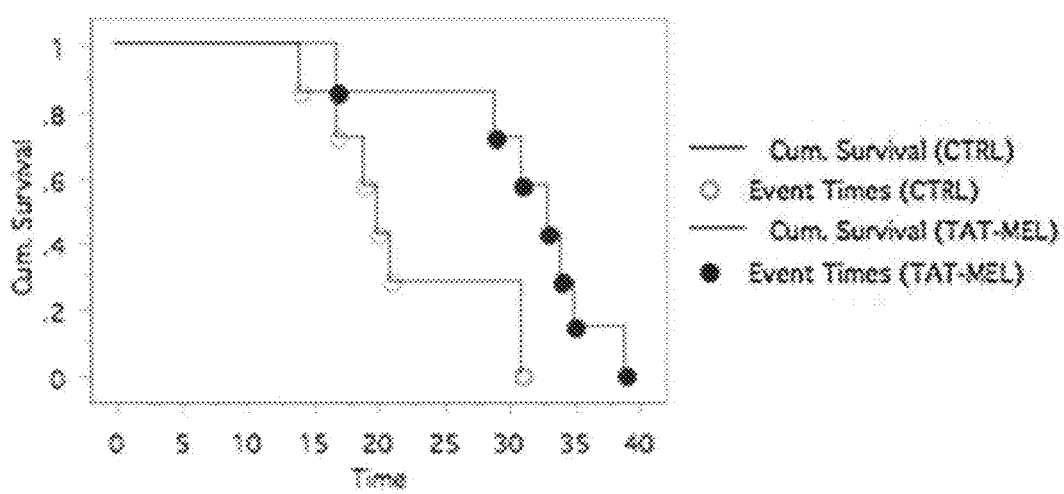
FIG. 30A depicts cumulative survival for control and melphalan-conjugated TAT monomer treated groups.
Figure 30B:
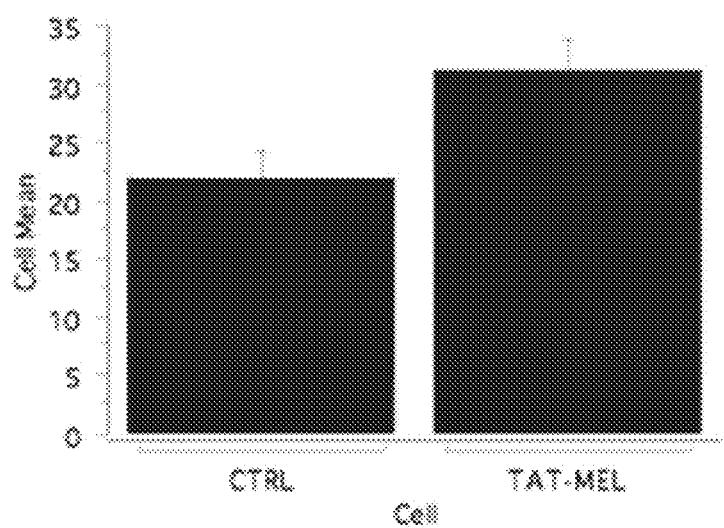
FIG. 30B depicts charts of survival for each treatment group.
Figure 31:
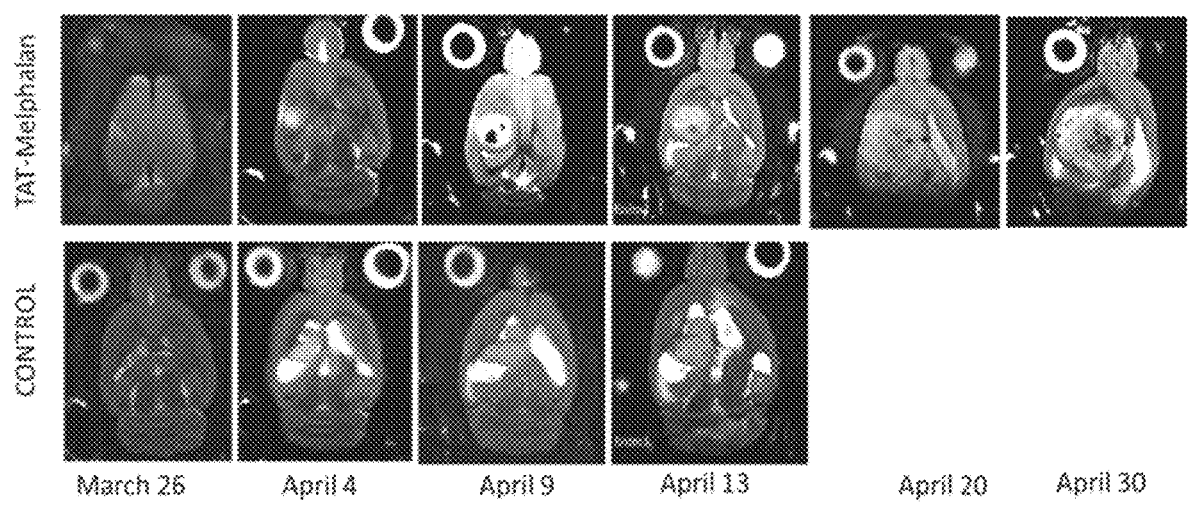
FIG. 31 depicts MRI images of the brain of a rat which survived 50 days post-implantation that was treated with melphalan-conjugated TAT monomer and a control rat brain.

As shown in FIGS. 30A-30B, survival increased for the melphalan-conjugated TAT monomer group as compared to the control group from 22+/−7 days to 31+/−7 days (p=0.025). This result was achieved with a lower dose of melphalan compared to the preceding experiment which resulted in improved survival at 0.25 mg melphalan. These results demonstrate that melphalan-conjugated TAT monomer is well tolerated and can effectively increase survival. Only one of seven animals showed some evidence of a tail bleed when the cannula was removed. FIG. 31 shows the MRI of the brain of the rat which survived 50 days after injection of melphalan-conjugated TAT monomer compared to a control rat brain.

Figure 32A:
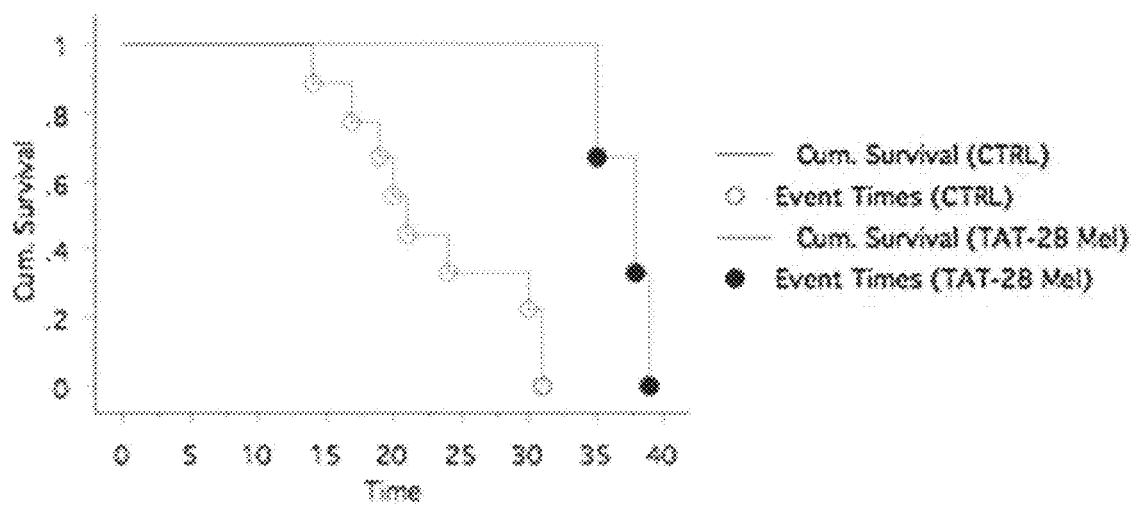
FIG. 32A depicts cumulative survival for control and melphalan-conjugated TAT dimer treated groups.
Figure 32B:
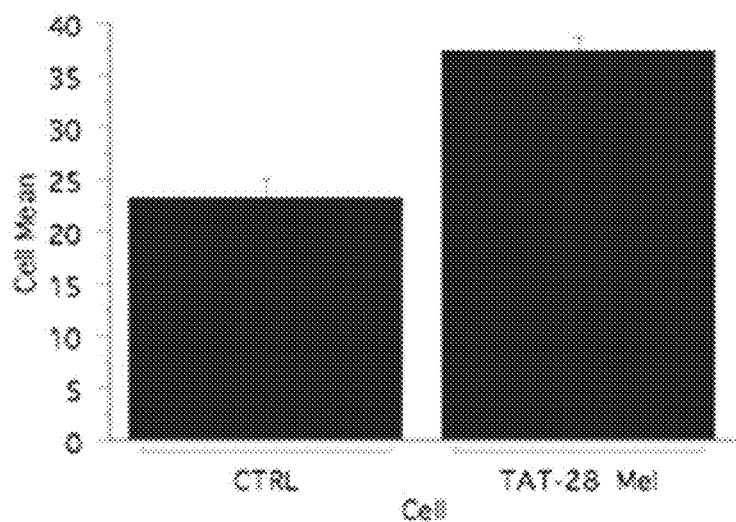
FIG. 32B depicts charts of survival for each treatment group. Control (CTRL) and melphalan-conjugated TAT dimer (TAT-28 Mel).

As shown in FIGS. 32A-32B, survival increased for the melphalan-conjugated TAT dimer group as compared to the control group from 23+/−6 to 37+/−2 days (p<0.004). No significant bleeding events were observed in the melphalan-conjugated TAT dimer group. Supporting MRIs showed cystic areas of necrosis but no evidence of regression of the tumor.

Example 10: Membrane Fluidity Effect on TAT Uptake 9L-gliosarcoma cells were grown to confluence in T-75 in recommended culture media. Membrane fluidity was determined by using commercially available "Gene Marker" kit. Fluorescein tagged TAT was used for determining uptake of the cell penetrating peptide. To alter membrane fluidity TAT uptake was determined at different temperatures of 4° C., 15° C. 25° C., 35° C. and 37° C.

The role of cholesterol in affecting membrane fluidity was then assessed. Cholesterol content of the membrane was measured using the commercially available Fillipin-III assay. Beta-cyclodextrin was used to deplete membrane cholesterol. The effect of cyclodextrin on TAT uptake of 100 μL at 0.1 mg/mL for 10 minutes at different temperatures was then assessed. Fluorescence was assessed by flow cytometry and confocal imaging was performed as needed.

Figure 33A:
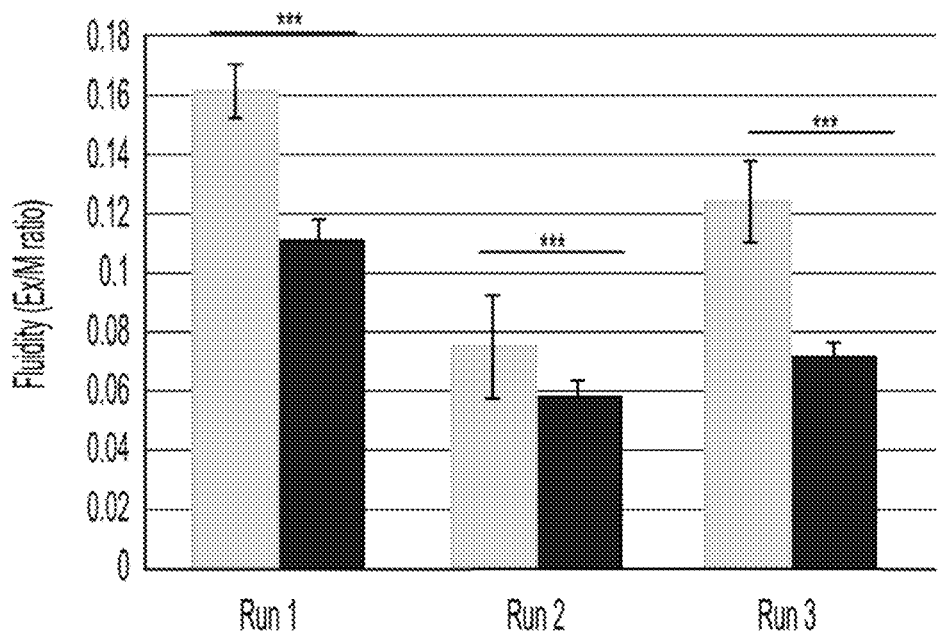
FIG. 33A depicts a chart of membrane fluidity at 4° C. (gray) and 37° C. (black).
Figure 33B:
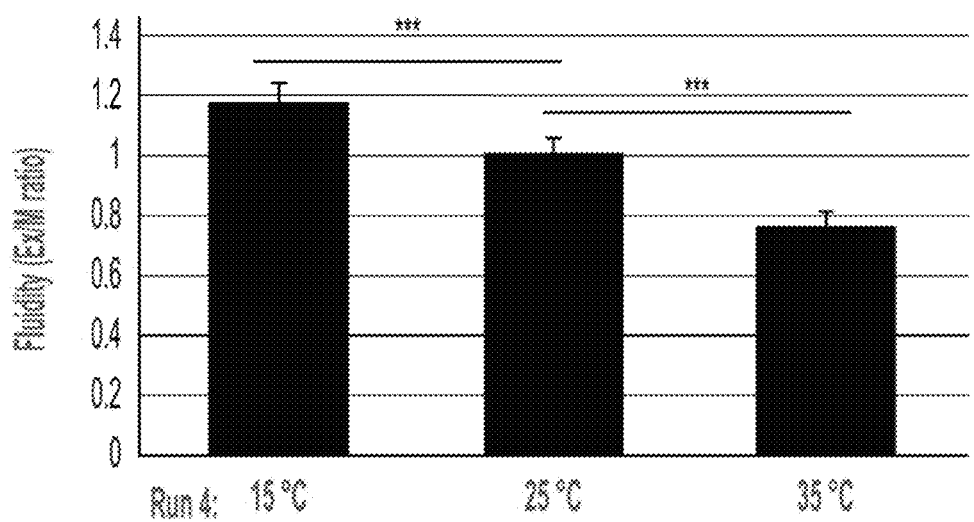
FIG. 33B depicts a chart of membrane fluidity by temperature.

As shown in FIG. 33A, cell membranes showed higher fluidity at 4° C. (light gray) than 37° C. (black). Confirmation of this effect is shown in FIG. 33B.

Figure 33C:
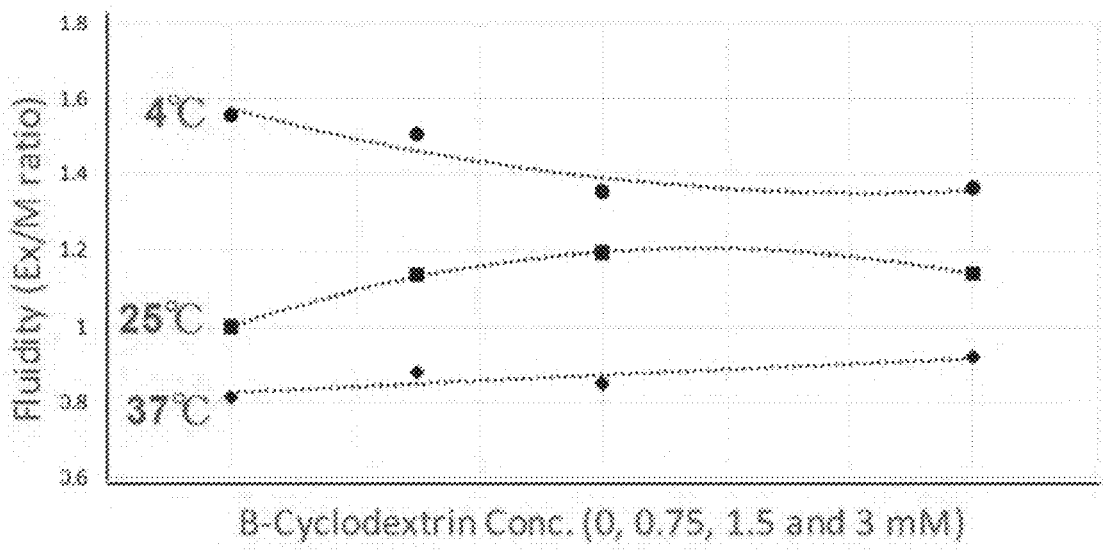
FIG. 33C depicts a chart of membrane fluidity at various temperatures and concentrations of beta-cyclodextrin.

As shown in FIG. 33C, addition of beta-cyclodextrin to remove cholesterol resulted in increased fluidity at higher temperatures (37° C.) than at lower temperature (4° C.) in a dose-dependent manner, indicating that cholesterol is at least partially responsible for the increased fluidity at lower temperatures.

Figure 33D:
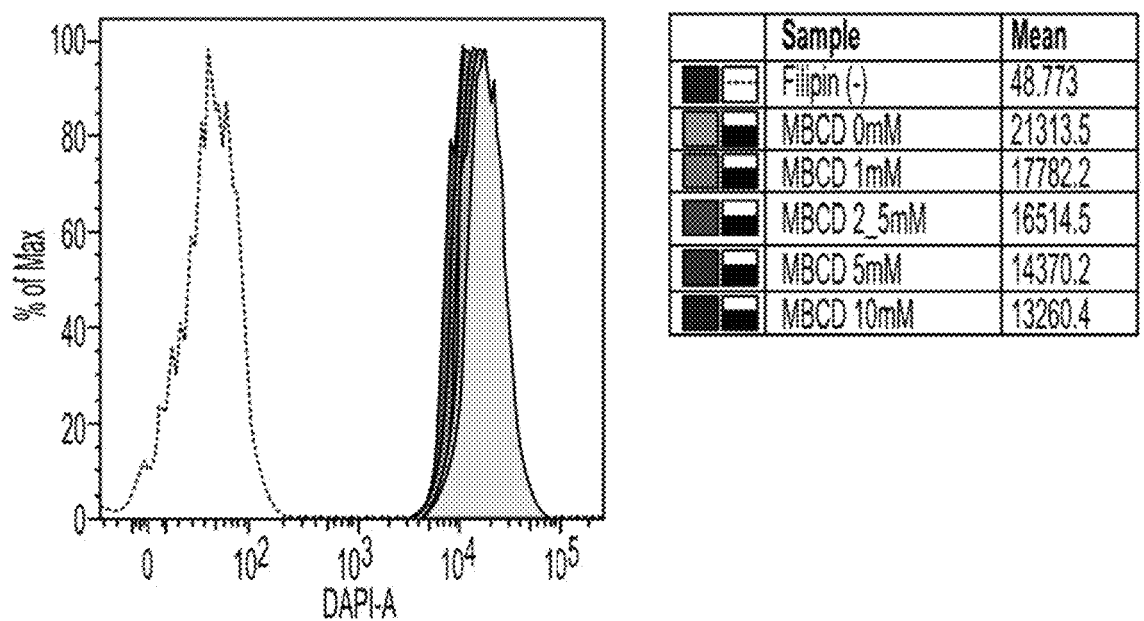
FIG. 33D depicts flow cytometry peaks for Filipin-III versus beta-cyclodextrin concentration.
Figure 33E:
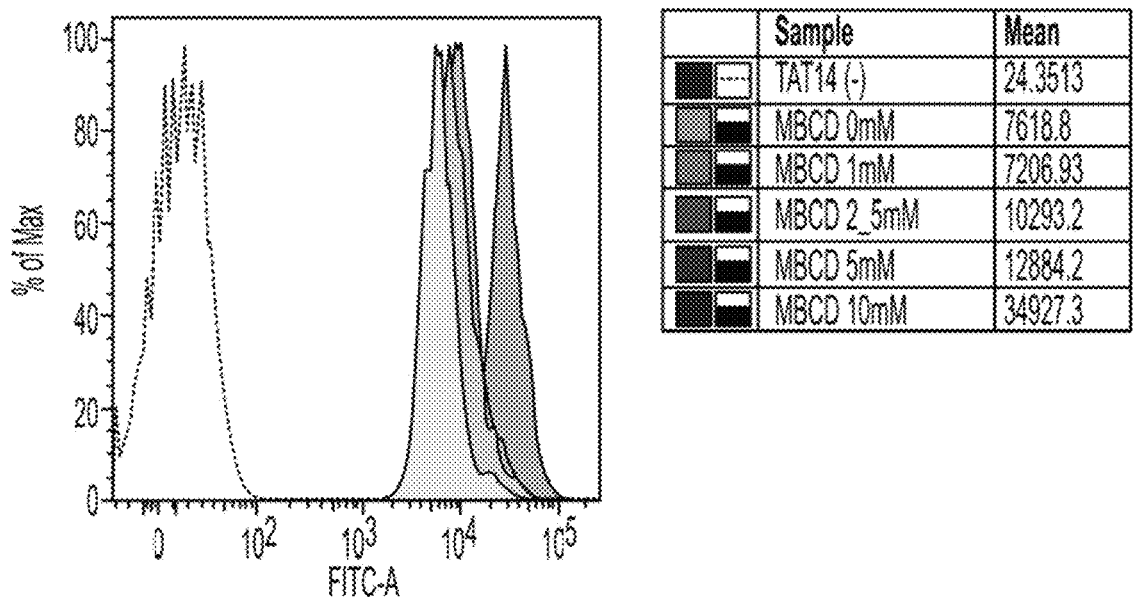
FIG. 33E depicts flow cytometry peaks for FITC versus beta-cyclodextrin concentration.
Figure 33F:
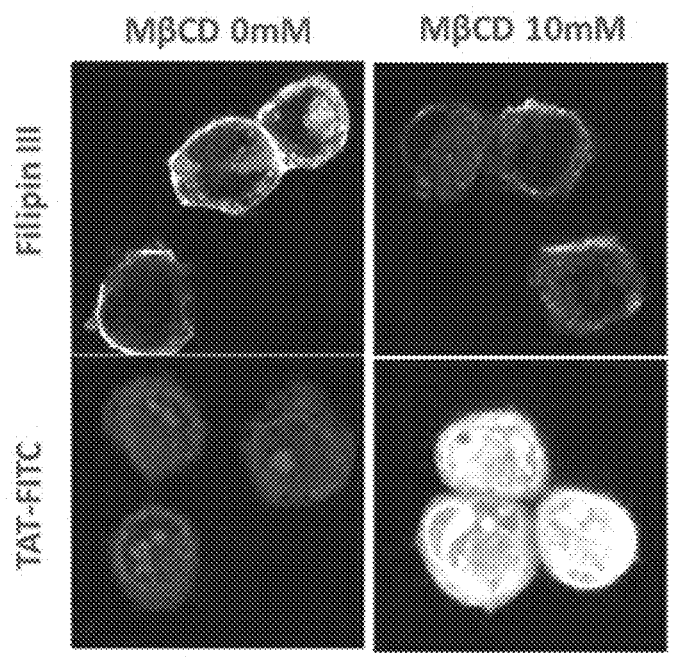
FIG. 33F depicts confocal microscopy images of cells exposed to FITC-labeled TAT monomer with or with beta-cyclodextrin and as measured for both Filipin-III and FITC.
Figure 33G:
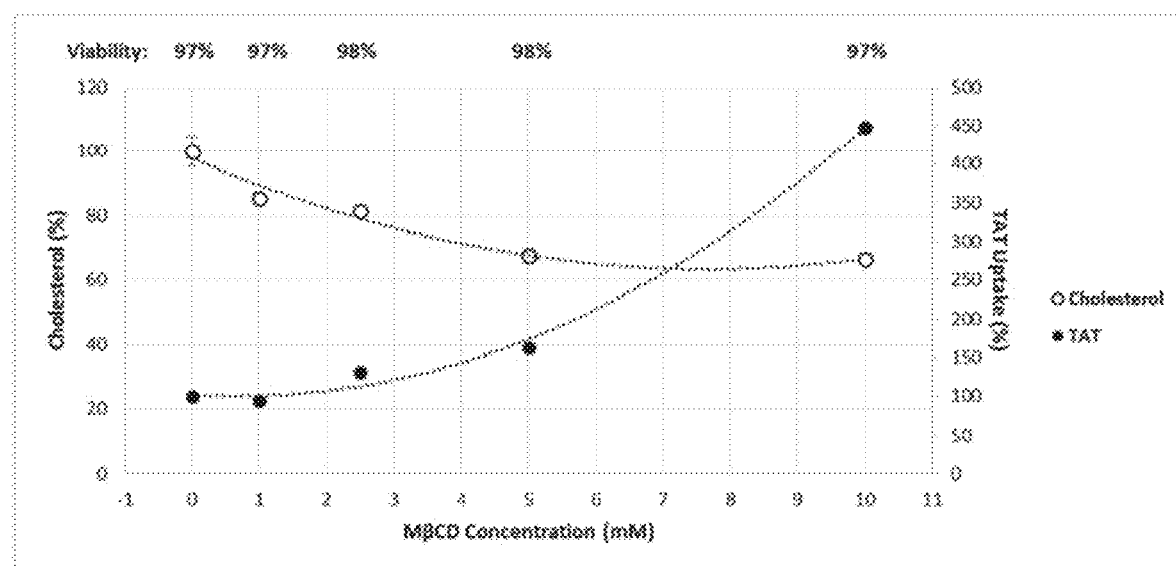
FIG. 33G depicts a chart of cholesterol and TAT uptake versus beta-cyclodextrin concentration.

As shown in FIGS. 33D-33E, increasing beta-cyclodextrin concentration, shifted the Fillipin-III peaks and fluorescein-labeled TAT monomer by flow cytometry. FIG. 33F shows confocal microscopy images of cells exposed to the fluorescein-labeled TAT monomer at beta-cyclodextrin concentrations of 0 mM or 10 mM with detection of Filipin-III or FITC. FIG. 33G shows a chart of TAT uptake versus beta-cyclodextrin concentration and cholesterol content.

These results demonstrate that uptake of TAT oligomers and conjugates thereof could be improved at lower temperatures.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated. Different features and disclosures of the various embodiments within the present disclosure may be combined within the scope of the present disclosure.

What is claimed is:

1. A peptide conjugate or pharmaceutically acceptable salt thereof comprising a peptide coupled to melphalan, said peptide comprising one or more trans-activating transcription factor (TAT) sequences, wherein each TAT sequence comprises the amino acid sequence of SEQ ID NO: 8 (GRKKRRQRRRPQ).

2. The peptide conjugate or pharmaceutically acceptable salt thereof of claim 1, further comprising a linker sequence between said melphalan and said peptide comprising one or more TAT sequences.

3. The peptide conjugate of claim 2, wherein the linker sequence is selected from an amino acid, a peptide, and a covalent linkage.

4. The peptide conjugate or pharmaceutically acceptable salt thereof of claim 2, wherein the linker sequence comprises one or more amino acids.

5. The peptide conjugate or pharmaceutically acceptable salt thereof of claim 2, wherein the linker sequence comprises lysine and is located at a C-terminal end of the peptide comprising one or more TAT sequences.

6. The peptide conjugate or pharmaceutically acceptable salt thereof of claim 1, wherein said melphalan is coupled to an N-terminal end of said peptide comprising one or more TAT sequences.

7. The peptide conjugate or pharmaceutically acceptable salt thereof of claim 1, wherein said at least one or more TAT sequences each further comprise at least one amino acid selected from the group consisting of G, C, P, Q, and combinations thereof.

8. The peptide conjugate or pharmaceutically acceptable salt thereof of claim 1, wherein said peptide comprises two or more TAT sequences.

9. The peptide conjugate or pharmaceutically acceptable salt thereof of claim 1, wherein said peptide comprises two to five TAT sequences.

10. The peptide conjugate or pharmaceutically acceptable salt thereof of claim 1, wherein said peptide comprises three TAT sequences.

11. The peptide conjugate or pharmaceutically acceptable salt thereof of claim 1, wherein said peptide comprises four TAT sequences.

12. The peptide conjugate or pharmaceutically acceptable salt thereof of claim 1, wherein said peptide comprises five TAT sequences.

\* \* \* \* \*